US009943546B2

(12) United States Patent
Weissman et al.

(10) Patent No.: US 9,943,546 B2
(45) Date of Patent: Apr. 17, 2018

(54) VIRAL INACTIVATED PLATELET EXTRACT, USE AND PREPARATION THEREOF

(71) Applicant: Omrix Biopharmaceuticals Ltd., Rehovot (IL)

(72) Inventors: Lior Weissman, Nes-Ziona (IL); Nina Raver-Shapira, Ramot Meir (IL); Israel Nur, Moshav Timmorim (IL); Oleg Belyaev, Petah Tikva (IL)

(73) Assignee: Omrix Biopharmaceuticals Ltd., Rehovot (IL)

(*) Notice: Subject to any disclaimer, the term of this patent is extended or adjusted under 35 U.S.C. 154(b) by 568 days.

(21) Appl. No.: 14/072,071

(22) Filed: Nov. 5, 2013

(65) Prior Publication Data

US 2014/0056989 A1    Feb. 27, 2014

Related U.S. Application Data

(62) Division of application No. 13/331,309, filed on Dec. 20, 2011, now Pat. No. 8,603,541.

(60) Provisional application No. 61/425,474, filed on Dec. 21, 2010.

(30) Foreign Application Priority Data

Dec. 20, 2011   (IL) .......................................... 226786

(51) Int. Cl.
*A61K 35/19*   (2015.01)
*A61K 38/18*   (2006.01)

(52) U.S. Cl.
CPC .............. *A61K 35/19* (2013.01); *A61K 38/18* (2013.01); *A61K 38/1825* (2013.01); *A61K 38/1841* (2013.01); *A61K 38/1858* (2013.01); *A61K 38/1866* (2013.01)

(58) Field of Classification Search
CPC ............ A61K 38/1866; A61K 38/1841; A61K 38/1858; A61K 38/18; A61K 35/19
USPC ....................... 424/532; 514/8.1, 8.2, 8.9, 9.1
See application file for complete search history.

(56) References Cited

U.S. PATENT DOCUMENTS

| | | | |
|---|---|---|---|
| 4,442,655 A * | 4/1984 | Stroetmann | A61K 38/363 106/124.1 |
| 4,789,545 A | 12/1988 | Woods et al. | |
| 5,094,960 A | 3/1992 | Bonomo | |
| 6,117,425 A * | 9/2000 | MacPhee | A61K 38/18 424/198.1 |
| 6,121,232 A | 9/2000 | Nur et al. | |
| 7,125,569 B2 | 10/2006 | Nur et al. | |
| 2003/0194692 A1 | 10/2003 | Purdum | |

FOREIGN PATENT DOCUMENTS

| | | |
|---|---|---|
| CN | 1596910 | 3/2005 |
| JP | 2004-123576 | 4/2004 |
| JP | 2009-524622 | 7/2009 |
| JP | 2009-530411 | 8/2009 |
| WO | WO 98/33533 | 8/1998 |
| WO | WO 02/095019 | 11/2002 |
| WO | WO 2009/087560 | 7/2009 |

OTHER PUBLICATIONS

Gagnon et al. The Secrets of Orthogonal Process Design. Validated Biosystems Inc, (2006), 4 pages.*
S. Ray. Viral Clearance Strategy Using a Three-Tier Orthogonal Technology Platform. BioPharm International (2008), v21(9), 6 page reprint.*
Arnaoutova I, Kleinman HK. In vitro angiogenesis: endothelial cell tube formation on gelled basement membrane extract. Nature Protocols. Nature Publishing Group 2010 vol. 5, No. 4 pp. 628-635.
Bar et al. 'The binding of fibrin sealant to collagen is influenced by the method of purification and the cross-linked fibrinogen-fibronectin (heteronectin) content of the 'fibrinogen' component' Blood Coagulation Fibrinolysis. Lippincott Williams & Wilkins 2005 vol. 16, No. 2 pp. 111-117.
Bertrand-Duchesne et al. Epidermal growth factor released from platelet-rich plasma promotes endothelial cell proliferation in vitro. Journal of Periodontal Research 2010 Blackwell Munksgaard Feb. vol. 45, No. 1 pp. 87-93.
Burnouf et al. 'A chromatographically purified human TGF-[beta]1 fraction from virally inactivated platelet lysates' Vox Sanguinis (2011) vol. 101, No. 3 pp. 215-220.
Burnouf et al. 'A novel virally inactivated human platelet lysate preparation rich in TGF-β, EGF and IGF, and depleted of PDGF and VEGF' Biotechnology and Applied Biochemistry (2010) vol. 56, Issue 4 pp. 151-160.
Circular of Information for the Use of Human Blood and Blood Components. American Red Cross, America's Blood Centers and the Armed Services Blood Program (Dec. 2009) 31 pages.
Cromwell et al 'Protein Aggregation and Bioprocessing' American Association of Pharmaceutical Scientists Sep. 15, 2006 vol. 8, No. 3 pp. E572-579. Review.
Intini 'The use of platelet-rich plasma in bone reconstruction therapy' Biomaterials. Elsevier Ltd. Oct. 2009 vol. 30, No. 28 pp. 4956-4966.
Johansson et al. Platelet lysate: a replacement for fetal bovine serum in animal cell culture? Cytotechnology. Kluwer Academic Publishers 2003 vol. 42, No. 2 pp. 67-74.
Kakudo et al. Proliferation-Promoting Effect of Platelet-Rich Plasma on Human Adipose-Derived Stem Cells and Human Dermal Fibroblasts. Plastic and Reconstructive Surgery. American Society of Plastic Surgeons Nov. 2008 vol. 122, No. 5 pp. 1352-1360.

(Continued)

*Primary Examiner* — Sean C Barron
(74) *Attorney, Agent, or Firm* — David R. Crichton

(57) ABSTRACT

The invention relates to a viral-safe platelet extract, to its preparation and use. The extract comprises a mixture of biologically active platelet derived factors.

Advantageously, the extract comprises a balanced proportion of the factors and is non-clottable.

11 Claims, 10 Drawing Sheets

(56) References Cited

OTHER PUBLICATIONS

Kanno et al. Platelet-Rich Plasma Enhances Human Osteoblast-Like Cell Proliferation and Differentiation. Journal of Oral and Maxillofacial Surgery. Elsevier Mar. 2005 vol. 63, Issue 3 pp. 362-369.
Lacci et al 'Platelet-Rich Plasma: Support for Its Use in Wound Healing' Yale Journal of Biology and Medicine Mar. 2010 vol. 83, No. 1 pp. 1-9.
Lang et al. In vitro scratch assay: a convenient and inexpensive method for analysis of cell migration in vitro. Nature Protocols. Nature Publishing Group 2007 vol. 2, No. 2 pp. 329-333.
Mach et al., 'Chapter 4—Ultraviolet Absorption Spectroscopy' Methods in Molecular Biology vol. 40: Protein Stability and Folding, Humana Press, Totowa, New Jersey 1995 pp. 91-114.
Mazzucco et al. 'Not every PRP-gel is born equal Evaluation of growth factor availability for tissues through four PRP-gel preparations: Fibrinet®, RegenPRP-Kit®, Plateltex® and one manual procedure' Vox Sanguinis. Aug. 2009 vol. 97, No. 2 pp. 110-118.
Mehta et al 'HB-EGF promotes angiogenesis in endothelial cells via PI3-kinase and MAPK signaling pathways' Growth Factors. Aug. 2007 vol. 25, No. 4 pp. 253-263.
Nagano et al. PDGF regulates the actin cytoskeleton through hnRNP-K-mediated activation of the ubiquitin $E_3$-ligase MIR. European Molecular Biology Organization Journal May 3, 2006 vol. 25, No. 9 pp. 1871-1882.
Nurden et al. Platelets and wound healing. Frontiers in Bioscience May 1, 2008; vol. 13 pp. 3532-3548.
Park et al 'Comparative Study on Motility of the Cultured Fetal and Neonatal Dermal Fibroblasts in Extracellular Matrix' Yonsei Medical Journal Dec. 2001 vol. 42, No. 6 pp. 587-594.
Robinson, S. et al 'Development and biochemical characterization of a double-virus-inactivated factor VIII preparation' Blood Coagulation & Fibrinolysis (1995) vol. 6, Suppl 2 pp. S40-S47.
Rozman et al Use of platelet growth factors in treating wounds and soft-tissue injuries. Acta Dermatovenerol Alp Panonica Adriat Dec. 2007 vol. 16, No. 4 pp. 156-165.
Rughetti et al. Platelet gel-released supernatant modulates the angiogenic capability of human endothelial cells. Blood Transfusion Jan. 2008 vol. 6, No. 1 pp. 12-17.
Ruiz-Saez A. et al 'Pharmacokinetics, thrombogenicity and safety of a double viral inactivated factor IX concentrate compared with a prothrombin complex concentrate' (2005) Haemophilia vol. 11 No. 6 pp. 583-588.
Shih, D. et al 'Expansion of adipose tissue mesenchymal stromal progenitors in serum-free medium supplemented with virally inactivated allogeneic human platelet lysate' Transfusion (2011) vol. 51 pp. 770-778.
Strancar, A. et al 'Extraction of Triton X-100 and its determination in virus-inactivated human plasma by the solvent-detergent method' J. of Chromatography (1994) vol. 658, No. 2 pp. 475-481.
Su, C-Y. et al. 'A virally inactivated functional growth factor preparation from human platelet concentrates' Vox Sanguinis (2009) vol. 97, No. 2 pp. 119-128.
Sulpice et al. Cross-talk between the VEGF-A and HGF signalling pathways in endothelial cells. Biology of the Cell Sep. 2009 vol. 101, No. 9 pp. 525-539.
International Preliminary Report on Patentability re: PCT/IL2011/000955 dated Jun. 25, 2013.
International Search Report re: PCT/IL2011/000955 dated May 4, 2012.
Burnouf, T. et al 'Solvent/detergent treatment of platelet concentrates enhances the release of growth factors' Transfusion, American Association of Blood Banks (2008) vol. 48, No. 6 pp. 1090-1098.
Burnouf T. et al 'A virally inactivated platelet-derived growth factor/vascular endothelial growth factor concentrate fractionated from human platelets' Transfusion (2010) vol. 50, No. 8 pp. 1702-1711.
GE Healthcare, Affinity Chromatography Principles and Methods, Oct. 2007 pp. 1-159.
Guerrier L. et al 'Specific sorbent to remove solvent-detergent mixtures from virus-inactivated biologicals fluids' J. Chromatogr B. Biomed Appl. (1995) 664(1) pp. 119-125.
Huang, M. et al Polyelectrolyte Complexes Stabilize and Controllably Release Vascular Endothelial Growth Factor (2007) Biomacromolecules v 8 pp. 1607-1614.
Kajio, T. et al 'Stabilization of basic fibroblast growth factor with dextran sulfate' (1992) FEBS v 306 pp. 243-246.
Salganicoff et al 'Subcellular fractionation of pig platelets.' (1975) Biochem Biophys Acta V 385 pp. 394-411.
Slezak, S. et al Platelet-mediated cytotoxicity. Role of antibody and C3, and localization of the cytotoxic system in membranes. (1987) J. Exp. Med V1666 pp. 489-505 French press.
European Search Report re: 15165721 dated Jul. 1, 2015.

\* cited by examiner

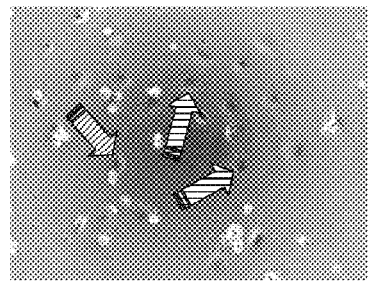 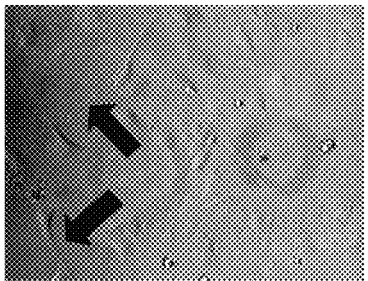
Fig. 3A  Fig. 3B
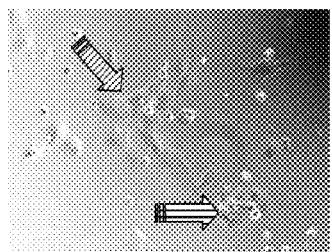 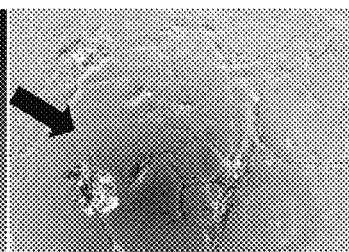 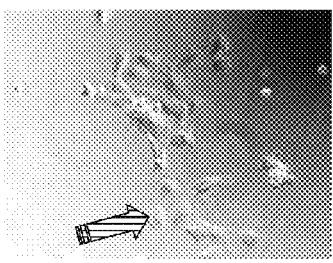
Fig. 4A  Fig. 4B  Fig. 4C
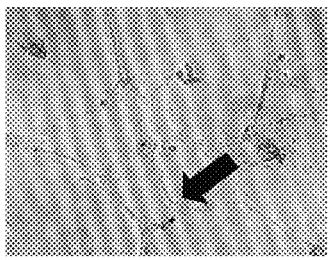 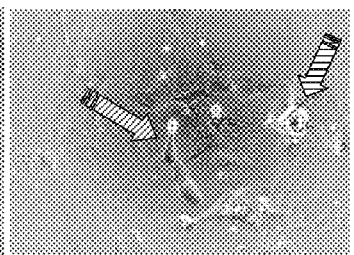 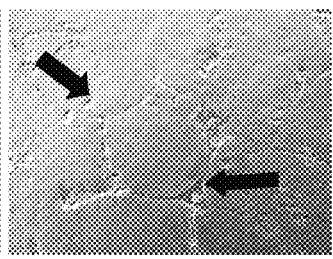
Fig. 4D  Fig. 4E  Fig. 4F

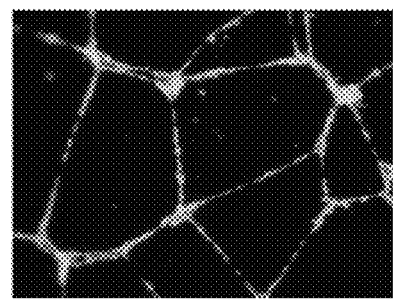
Fig. 7
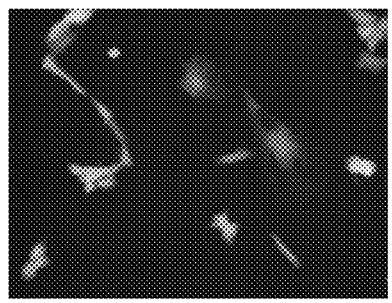 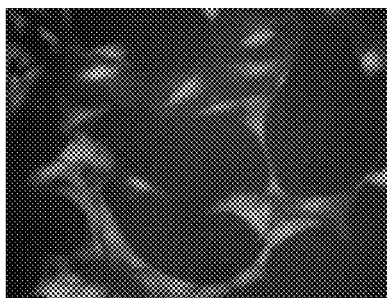
Fig. 8A          Fig. 8B
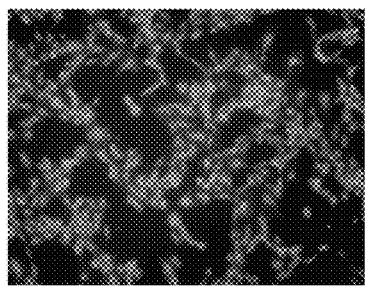 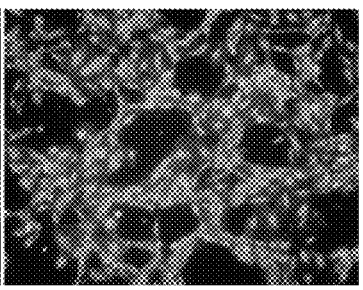 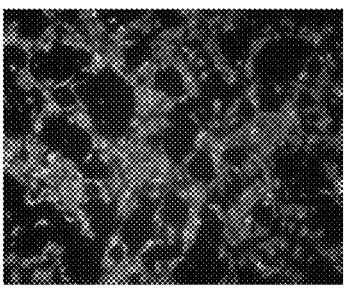
Fig. 9A          Fig. 9B          Fig. 9C
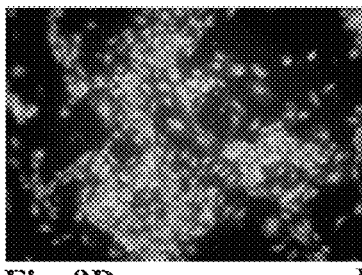 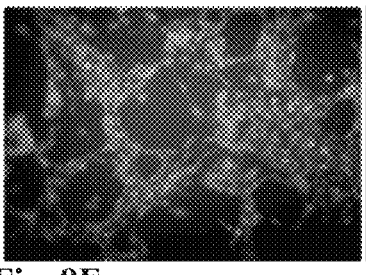 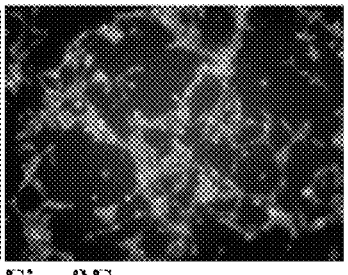
Fig. 9D          Fig. 9E          Fig. 9F

VIRAL INACTIVATED PLATELET EXTRACT, USE AND PREPARATION THEREOF

This application is a Divisional that claims the benefit of U.S. Non-Provisional Ser. No. 13/331,309, filed Dec. 20, 2011, which claims priority of U.S. Provisional Application Ser. No. 61/425,474, filed Dec. 21, 2010, the disclosure of which is hereby incorporated by reference herein. The present application also claims benefit of Israeli Patent Application Number IL210162, filed Dec. 21, 2010.

FIELD OF THE INVENTION

The invention relates to viral-inactivated platelet extract derived from multiple donors; to its preparation and use.

BACKGROUND OF THE INVENTION

Platelets are small, irregularly-shaped a-nuclear cells that play a fundamental role in hemostasis and healing. Platelets contain a complete array of pre-synthesized proteins, among which are signaling proteins, cytoskeletal proteins, membrane proteins and regulatory proteins. They are involved in key stages of tissue regeneration and healing processes at the site of injury, mainly due to the content of platelet granules comprising a multitude of bioactive molecules including growth factors (GFs), cytokines and chemokines. Platelet GFs such as platelet-derived growth factor (PDGF), transforming growth factor (TGF), basic fibroblast growth factor (bFGF), vascular endothelial growth factor (VEGF) and others are key players in all the following phases of the wound healing cascade: inflammatory, proliferative and remodeling phase.

Studies have shown that platelet derived GFs stimulate angiogenesis, mitogenesis, cell proliferation, neutrophils and macrophages, collagen synthesis, wound contraction, extracellular matrix synthesis, epithelialization and chemotaxis.

Platelets are routinely used by transfusion e.g. to improve hemostasis. Recently, platelets are increasingly used in the form of Platelet Rich Plasma (PRP), also referred to as PRP gel, platelet gel, PRP-clot etc. Typically, PRP is an ex vivo preparation consisting of autologous platelets concentrated in a limited volume of plasma (Lacci K M, Dardik A. Platelet-rich plasma: support for its use in wound healing. Yale J Biol Med. 2010 March; 83(1):1-9).

For topical application, PRP is usually activated by the addition of thrombin and/or $CaCl_2$ resulting in the formation of fibrin gel by the interaction between thrombin (endogenous or exogenous) and fibrinogen. Upon activation, the platelets undergo active degranulation and release various mediators including GFs (Lacci K M, Dardik A, 2010). The use of PRP for injection currently comprises a small but rapidly growing segment of the market. The rationale for using PRP in soft and hard tissue augmentation is its potential to enhance tissue regeneration in non-healing injuries, accelerate wound maturity, vascularization and epithelialization, decrease scar formation, and reduce post operative complications and morbidity (Lacci K M, Dardik A, 2010).

Studies using activated PRP together with various cell types have shown that factors e.g. growth factors released from PRP can induce cell proliferation [(e.g. Kanno et al. Platelet-rich plasma enhances human osteoblast-like cell proliferation and differentiation. J Oral Maxillofac Surg. 2005 March; 63(3):362-9; Bertrand-Duchesne et al. Epidermal growth factor released from platelet-rich plasma promotes endothelial cell proliferation in vitro. J Periodontal Res. 2010 February; 45(1):87-93; Kakudo et al. Proliferation-promoting effect of platelet-rich plasma on human adipose-derived stem cells and human dermal fibroblasts. Plast Reconstr Surg. 2008 November; 122(5):1352-60), modulate the angiogenic capability of human endothelial cells (Sulpice et al. Cross-talk between the VEGF-A and HGF signalling pathways in endothelial cells. Biol Cell. 2009 September; 101(9):525-39; Rughetti et al. Platelet gel-released supernatant modulates the angiogenic capability of human endothelial cells. Blood Transfus. 2008 January; 6(1):12-7), and induce osteo-inductive properties (Intini G. The use of platelet-rich plasma in bone reconstruction therapy. Biomaterials. 2009 October; 30(28):4956-66)]. Moreover, activated PRP was found to support in vitro cell growth and maintained viability of a number of target cells including myelomas, hybridomas, hepatocytes, fibroblasts and epithelial cells, at a level comparable or superior to the level supported by fetal bovine serum (Johansson et al. Platelet lysate: a replacement for fetal bovine serum in animal cell culture? Cytotechnology. 2003 July; 42(2):67-74).

PRP and released growth factors are currently used in various surgical tissue regeneration procedures, predominantly in orthopedic and dental surgery (Nurden et al. Platelets and wound healing. Front Biosci. 2008 May 1; 13:3532-48). In orthopedic surgery PRP is used mainly for knee arthroplasty, lumbar spinal fusion, and in intervertebral disc degeneration (reviewed in Nurden et al, 2008). Dentistry and maxillofacial surgery PRP applications include mainly consolidation of titanium implants, maxillary sinus augmentation and bone remodeling (reviewed in Nurden et al, 2008). PRP is also increasingly used for tendon and ligament repair, facial plastic and reconstructive surgery, chronic skin wound healing, ophthalmology, facial nerve regeneration, as well as in cardiac and bariatric surgery (reviewed in Nurden et al, 2008).

However, a major disadvantage of the current use of autologous PRP and released factors resides in the lack of standardization. Of note, different manual, semi-automated and fully-automated systems for preparation of PRP are commercially available that differ in parameters such as preparation time, platelet yield and collection efficiency (Mazzucco et al. Not every PRP-gel is born equal. Evaluation of growth factor availability for tissues through four PRP-gel preparations: Fibrinet, RegenPRP-Kit, Plateltex and one manual procedure. Vox Sang. 2009 August; 97(2): 110-8).

Another important variable is the technique used for platelet activation [autologous, heterologous or recombinant thrombin, calcium chloride or batroxobin (Rozman P, Bolta Z. Use of platelet growth factors in treating wounds and soft-tissue injuries. Acta Dermatovenerol Alp Panonica Adriat. 2007 December; 16(4):156-65)], which can affect the efficiency of granule release and the amount of secreted GFs (Rozman P, Bolta Z, 2007). Moreover, since platelets are very sensitive to mechanical stress and changes in the surrounding environment, they may be activated and GFs may be released during processing, prior to the intended activation step (Mazzucco et al, 2009). This uncontrolled activation may further increase the variability in the composition of the final product when using different PRP preparation systems. Additionally, a major inherent weakness of autologous PRP preparation is that the platelets GFs content varies among individuals, and therefore may lead to sub-optimal results. Finally, the financial burden of dedicated machinery, disposable PRP processing kits, and the need for trained personnel, should be taken into consideration when working with autologous PRP.

A recent publication (Su et al. "A virally inactivated functional growth factor preparation from human platelet concentrates". Vox Sang. 2009 August; 97(2):119-128) discloses the preparation of a clottable functional growth factor extract derived from pooled aphaeresis platelet donations. However, the disclosed clottable preparation has the disadvantage that it includes only one viral inactivation step, i.e. solvent detergent (S/D) viral inactivation which is effective particularly against enveloped viruses, but not against non-enveloped viruses. The publication indicates the possibility of applying nanofiltration as a second viral inactivation step. This preparation also contains plasma and leukocyte protein impurities. The step of S/D removal by hydrophobic interaction chromatography (HIC) largely reduces the PDGF in the preparation. Furthermore, the clotability potential of the preparation may limit its use to local application or prevent its systemic use.

Burnouf et al. ("A novel virally inactivated human platelet lysate preparation rich in TGF-beta, EGF and IGF, and depleted of PDGF and VEGF". Biotechnol Appl Biochem. 2010 Aug. 6; 56(4):151-60) discloses an S/D treated platelet lysate with a standardized content of TGF-beta, EGF and IGF and depleted of PDGF and VEGF. The publication discloses a method for preparation of this lysate evading removal of SD by hydrophobic interaction chromatography.

There is a need of a viral-safe platelet extract preparation obtained from multiple donors comprising a mixture of proteins having growth factor and/or trophic factor activity.

SUMMARY OF THE INVENTION

Platelets contain a complete array of factors involved in key stages of tissue regeneration and healing processes. Currently, whole autologous activated platelets (derived from the patient) are used for facilitating wound healing. However, there are multiple disadvantages of using whole autologous platelets, inter alia, the lack of standardization; the factors needed for healing may be scarce in the patient's own platelets; the special equipment needed; the procedure is time consuming and requires additional steps which are carried out on the patient itself; and the requirement of medically trained personnel. These problems can be solved e.g. by using a platelet extract prepared from multiple donors. However, human blood-derived products may carry a risk of transmitting infectious agents such as viruses. Effective reduction of viral transmission risk can be achieved by including at least two orthogonal viral inactivation steps. Yet, additional steps in the manufacture of a platelet extract may compromise the recovery and activity of the factors contained therein.

The invention solves a long felt need for a viral safe (at least double viral inactivated) platelet protein extract obtained from multiple donors comprising a mixture of proteins having growth factor and/or trophic factor activity.

The invention relates to an active and viral-safe platelet extract derived from multiple donors; to its preparation and use.

The viral-safe platelet extract comprises a mixture of active platelet cell growth factors and/or trophic factors.

In one aspect, the invention relates to a method for preparing a viral-safe platelet extract, the method comprising at least two orthogonal viral inactivation treatments e.g. solvent detergent (S/D) viral inactivation treatment and heat inactivation. The method comprising the following steps:

providing a platelet-enriched fraction from multiple donors e.g. a washed and/or leukocyte-reduced platelet fraction from aphaeresis pooled from multiple donors;
preparing a platelet lysate;
carrying out a solvent detergent (S/D) viral inactivation treatment;
removing the S/D by hydrophobic interaction chromatography (HIC), wherein the HIC comprises the steps of: loading the lysate to HIC, and collecting a material eluted under non isocratic conditions; and
conducting a second orthogonal viral inactivation treatment.

In one embodiment of the invention, preparing the platelet lysate is carried out during the S/D viral inactivation treatment.

In a further embodiment of the invention, during the S/D viral inactivation treatment a sub step of aggregate reduction is carried out e.g. by filtration.

In certain embodiments of the invention, the HIC comprises the steps of: loading the lysate to HIC; washing HIC with an isocratic solution; collecting the unbound material; washing HIC with a non isocratic solution; and collecting the eluted material.

Yet, in a further embodiment of the invention, the isocratic solution consists of acetate glycine buffer and human serum albumin; and wherein the non isocratic solution comprises an organic solvent and/or a molecule capable of binding platelet derived factors.

Yet, in a further embodiment of the invention, the lysate is contacted with a molecule capable of binding platelet-derived factors, e.g. heparin, dextran sulphate and combination thereof, prior to S/D removal.

Yet, in a further embodiment of the invention, the extract is lyophilized.

In another aspect, the invention relates to a viral-safe platelet extract, obtainable according to the method of the invention.

The invention provides a viral-safe platelet extract derived from multiple donors comprising a mixture of biologically active platelet cell growth factors and/or trophic factors.

In one embodiment of the invention the extract comprises PDGF-AB, VEGF and TGFb1, wherein the ratio for PDGF-AB:TGF-b1 is at least 0.2; and/or the ratio for PDGF-AB:VEGF is at least 45.

In one embodiment of the invention, the extract is enriched with PDGF-AB and/or bFGF.

In one embodiment of the invention, the extract is non-clottable.

In one embodiment of the invention, the extract has a low aggregate content.

In one embodiment of the invention, the extract is in solid form.

In one embodiment of the invention, the extract is provided with a delivery agent made of natural and/or synthetic material selected from the group consisting of polymers, hydrogels, polyvinyl alcohol, polyethylene glycol, hyaluronic acid, chondroitin sulphate, gelatin, alginate, collagen matrices, carboxymethylcellulose, dextran, poly(2-hydroxyethylmethacrylate), agar, oxidize regenerated cellulose, self assembled peptides, poly(glycolic) acid, poly(lactic) acid, fibrin and combinations thereof.

In another aspect, the invention relates to the use of the extract in tissue healing; organ reconstruction; tissue regeneration and/or treating inflammation.

In another aspect, the invention relates to a method of tissue healing; organ reconstruction and/or tissue regeneration comprising administering to a subject in need a therapeutically effective amount of an extract according to the invention.

In another aspect, the invention relates to a method of treating inflammation in a subject in need comprising administering to a subject in need a therapeutically effective amount of an extract according to the invention.

In one embodiment of the invention, the extract is administered with a delivery agent.

The invention provides a method for removing solvent-detergent (S/D) from a biological liquid mixture by hydrophobic interaction chromatography (HIC), comprising the steps of:
providing the biological liquid mixture; and
loading the mixture to HIC, collecting the unbound material and a material eluted under non isocratic conditions.

The invention also provides a method for removing solvent-detergent (S/D) from a biological liquid preparation by HIC, comprising the steps of:
providing the preparation;
loading the preparation to HIC; and
collecting a material eluted under non isocratic conditions.

In one embodiment of the invention, the biological preparation is a platelet derived preparation.

In one embodiment of the invention, the method comprises the steps of: loading the preparation to HIC; washing HIC with an isocratic solution; collecting the unbound material; washing HIC with a non isocratic solution; and collecting the eluted material.

In one embodiment of the invention, the method comprises an isocratic solution consisting of acetate glycine buffer and human serum albumin; and a non isocratic solution comprising an organic solvent and/or a molecule capable of binding platelet derived factors.

In another aspect, the invention provides a viral-safe preparation or mixture, obtainable according to the method of the invention.

Yet in another aspect, the invention provides a kit comprising a recipient containing an extract according to the invention, optionally comprising a delivery agent.

In one embodiment, the delivery agent is made of natural and/or synthetic material selected from the group consisting of polymers, hydrogels, polyvinyl alcohol, polyethylene glycol, hyaluronic acid, chondroitin sulphate, gelatin, alginate, collagen matrices, carboxymethylcellulose, dextran, poly(2-hydroxyethylmethacrylate), agar, oxidize regenerated cellulose, self assembled peptides, poly(glycolic) acid, poly(lactic) acid, fibrin and combinations thereof.

BRIEF DESCRIPTION OF THE DRAWINGS

FIG. 3 shows a representative light microscopy image (at magnification of ×200) of 3T3-Swiss albino cell morphology of (A) Untreated control cells (cells grown in starvation medium); or (B) Cells treated with LYO I.

FIG. 4 shows a representative light microscopy image (at magnification of ×200) of HUVEC morphology upon addition of LYO I (B), 2 IU/ml thrombin (C); LYO I+2 IU/ml thrombin (D); BAC component (E); or LYO I+BAC component (F). (A) Untreated control cells.

FIG. 7 shows vessel-like structures acquired by HUVEC seeded on Basement Membrane Extract (BME) coated wells (positive control). The picture was taken at ×100 magnification using fluorescence filter for 530 nm.

FIG. 8 shows vessel-like structures acquired by HUVEC following treatment with LYO II (B). (A) Control cells. The pictures were taken at ×200 magnification using fluorescence filter for 530 nm.

FIG. 9A-9F show the morphological appearance of HUVEC seeded on fibrinogen (A-C) or fibrin coated (D-F) cells and treated with LYO II (B,E) or pooled WAP II (C,F) or untreated (A,D). The pictures were taken at 100-fold magnification using fluorescence filter for 530 nm.

DESCRIPTION OF EMBODIMENTS OF THE INVENTION

Figure 1:
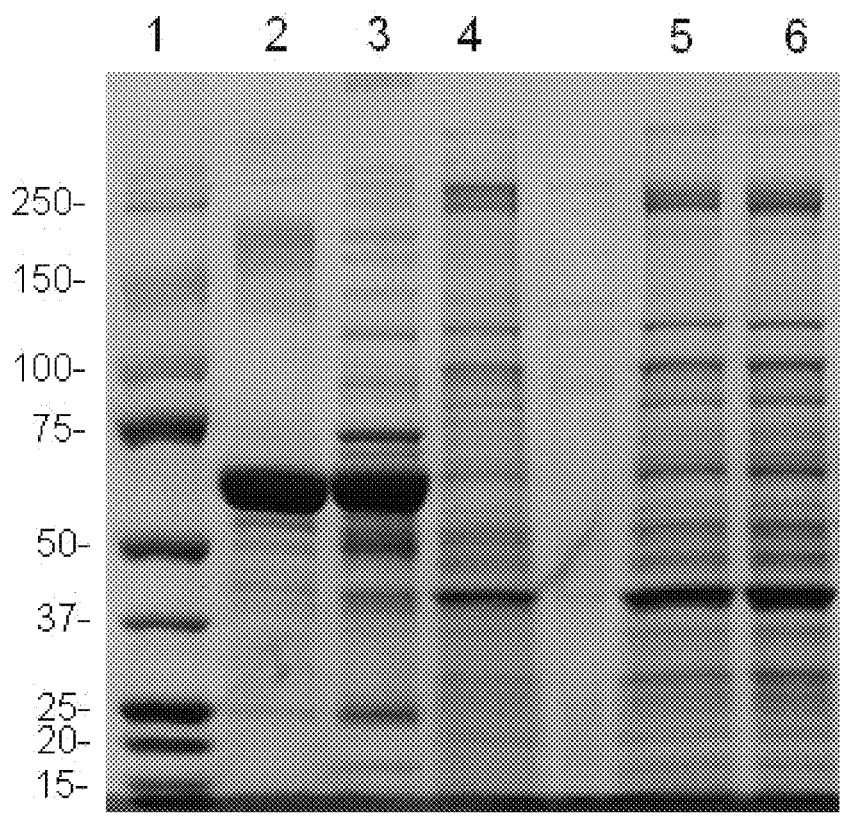
FIG. 1 shows SDS-PAGE protein profile characterization of different platelet extract preparations. Molecular weight markers [Bio-Rad 161-0374 (lane 1)]; Human serum albumin [Plasbumin 25. (lane 2)] 8 µg; Washed platelets from whole blood (lane 3) 11 µg; WAP (lane 4) 8 µg; WAP after S/D treatment (lane 5) 14 µg; WAP after S/D treatment and SD removal by SDR HyperD chromatography resin purification (lane 6) 10 µg.

The invention relates to an active and viral-safe (at least double viral inactivated) platelet extract derived from multiple donors; to its preparation and use. The viral-safe platelet extract comprises a mixture of biologically active platelet cell growth factors and/or trophic factors.

It was found according to the present invention that washed leukocyte-reduced aphaeresis platelets (WAP) contain very small amounts of albumin and, possibly, small amounts of other plasma impurities relative to washed platelets obtained from whole blood donation. It was also found that WAP subjected to S/D treatment (lysis and viral inactivation), S/D removal, lyophilization and reconstitution (e.g. LYO I extract) was biologically active and capable of inducing proliferation and/or changes in morphology e.g. vessel-like structure formation (associated with angiogenesis) or formation of spindle-like structures (an attribute of increased motility) in cell lines e.g. Human Umbilical Vein Endothelial Cells (HUVEC) or 3T3 fibroblasts cells. It was observed that the activity of the extract could be increased by addition of thrombin, biologically active component (BAC; a fibrinogen component as in EVICEL™ fibrin sealant, Omrix Biopharmaceuticals Ltd.) or thrombin+BAC (Fibrin).

Human blood-derived products may carry a risk of transmitting infectious agents such as viruses. Several measures are usually taken in order to minimize the risk of viral and/or unknown pathogens transmission including routine testing of donated samples for the presence of certain viruses, and viral inactivation/removal steps during the manufacture process. Effective reduction of viral transmission risk can be achieved by including at least two orthogonal viral inactivation steps that do not alter the beneficial properties of the product. Lipid-enveloped viruses such as HIV, hepatitis B, hepatitis C and West Nile Virus are quickly and efficiently inactivated by the S/D treatment which destroys the lipid membrane of the viruses.

Next, the extract was subjected to a second viral inactivation treatment e.g. a heat treatment (pasteurization) step or nanofiltration. It was found according to the invention that the extract could not easily pass through a nanofiltration system.

Surprisingly, it was found according to the invention that a heat treatment (pasteurization) viral inactivation step is feasible and yields a biologically active extract (e.g. LYO II) as tested by a cell proliferation assay and induction of morphological changes (e.g. induction of angiogenesis or induction of spindle like shapes) assay. It was found that thrombin, fibrinogen or fibrin addition pronounced the extract activity (fibrinogen or fibrin addition by promoting tubular structure formation and thrombin by increasing proliferation).

In one embodiment of the invention, for heat treatment, the S/D treated material is subjected to a step of stabilization. Sucrose and glycine can be added into the solution to serve as stabilizers during the pasteurization step. The solution can then be pasteurized e.g. by heat treatment at 60±0.5° C. for 9-10.5 hours with constant mixing. Then the solution can be diluted e.g. with acetate-glycine buffer and the stabilizers can be removed from the solution e.g. by diafiltration against acetate-glycine buffer. If aggregated material is present, it can be removed by filtration through one or more sequential filtrations e.g. using 20, 5 and 1.2 µm filters, followed by 0.45 µm filter. Sterile filtrations can be carried out under aseptic conditions using a 0.2 µm filter. The solution can be lyophilized in autoclaved vials and sealed with autoclaved rubber stoppers under nitrogen atmosphere and in partial vacuum (0.6 Bar).

It was found according to the invention that the double viral-inactivated extract could be concentrated (e.g. as in LYO III) e.g. four-fold or 32-fold compared to the concentration of the starting material. Concentration can be achieved e.g. by diafiltration of the solution and/or reconstitution of the lyophilized extract in a lower volume compared to the volume of the extract prior to lyophylization.

If aggregated material is present, it can be removed by sequential filtration as above. It was found that the concentrated extract (e.g. LYO III) comprises very low amounts of plasma proteins. It was found that the concentrated extracts (e.g. LYO VI and LYO VII) were non-clottable. The extracts exhibited marginal levels or complete absence of clotting proteins. The concentrated extract is depleted of physiologically active fibrinogen since the levels of physiologically active fibrinogen are undetectable by a sensitive method currently used in the art. The extracts lacked pro-coagulant activity as assessed by the non-activated partial thromboplastin time measurement test (NAPTT). The NAPTT can be carried out essentially as described in the European Pharmacopoeia 7.0; 2.6.22: Activated coagulation factors monograph (01/2008:20622); in European Pharmacopoeia Strasburg (France), Council of Europe, 2009. The absence of coagulation factors was also determined by the Activated Partial Thromboplastin Time (APTT) test. It was shown by this test that the platelet extract according to the invention is deficient in one or more of the coagulation factors XII, XI, IX, VIII, X, V, II, and I, rendering the extract non-clottable.

It was found according to the invention that increasing the concentrations of the extract affected the proliferation level of 3T3-Swiss albino mouse fibroblast cells with the effect of the concentrated extract being more pronounced than a lysate of the starting material while normalized to the amounts of PDGF-AB present in the samples. Notably, the effect of the concentrated extracts was more pronounced than the positive control (MasterMix, a custom mixture of recombinant human growth factors prepared with TGF-β1 200 ng/ml, b-FGF 0.5 ng/ml, VEGF 5 ng/ml and PDGF-AB 300 ng/ml). It was also found that addition of the concentrated extract to Human Umbilical Vein Endothelial Cells (HUVEC) monolayer promoted tubulogenesis. A synergistic effect in tubulogenesis of HUVEC monolayer was shown by the addition of the concentrated extract in combination with fibrin sealant.

For optimal S/D viral inactivation a sub step of aggregate removal can be added during the S/D treatment (e.g. as carried out in LYO IV). Aggregate removal can be carried out e.g. by centrifugation; filtration; preparative size exclusion chromatography (SEC); ultrafiltration e.g. using 100 KD polyethersulfone (PES) membrane, 100 KD polyvinylidene fluoride (PVDF) membrane, 300 KD PES membranes, polypropylene membranes, cellulose acetate membranes and/or by any other method known in the art.

Optionally, an additional step of aggregate removal by addition of calcium chloride, or other calcium salts, and clarification filtration is included. E.g. calcium chloride at a final concentration of 40 mM can be added (to facilitate the precipitation of aggregates) followed by clarification filtration e.g. using 20, 5, 1.2 and 0.45 µm filters. In one embodiment, this step is added after the S/D treatment.

It was found according to the invention that these additional steps of aggregate removal are feasible and yield a biologically active extract. A platelet extract having a low aggregate content can be advantageously used for intravenous administration. Also, a platelet extract having a low aggregate content can be used together with a component comprising a relatively high concentration of calcium.

It was found in uncoated cell culture wells, and in collagen or fibrinogen coated wells containing fibroblast, that treatment of the cells with extracts which were subjected to aggregate removal, promoted fibroblasts motility and closure of wound (in scratch assay) in a similar manner as the lysate of the starting material and as PRP-R [(PRP-releasate, activated with calcium and thrombin (from EVI-CEL™)]. PRP-R has been reported to be beneficial in wound healing in in-vivo settings (Lacci K M, Dardik A, 2010).

In addition, it was found according to the invention that extracts subjected to aggregate removal induced in HUVEC strong morphological changes which are associated with angiogenesis.

It was found according to the invention that certain platelet factors can be recovered during the S/D removal step by adding at least one elution step in the HIC column used for the S/D removal and by collecting also the eluted material. One such factor is PDGF-AB. It was found that by washing HIC with a non isocratic solution, in accordance to the invention, at least 3-fold recovery or enrichment of PDGF-AB can be obtained (as in LYO V, VI, and VII). The concentration of PDGF-AB was measured in the final lyophilized material following reconstitution with 4 ml double distilled water (DDW). The concentration of PDGF-AB was found to be 4,578 pg/ml in LYO VI, 15,028 pg/ml in LYO V, and 194,353 pg/ml in LYO VII which corresponds to about $7\times10^{-7}$ pg in LYO VI, $2.26\times10^{-6}$ pg in LYO V, and $3.12\times10^{-5}$ pg in LYO VII PDGF-AB per platelet used as the starting material. Notably, the effect of the extract enriched with PDGF-AB on proliferation of cells was more pronounced than recombinant PDGF-AB alone, pointing to the fact that other platelets' extracted components may synergistically enhance fibroblasts proliferation. Another factor enriched/increased using the method of the invention is bFGF (also named FGF-2 or β-FGF). It was also found that by washing HIC with a non isocratic solution, in accordance to the invention, at least 1.8 fold recovery or enrichment of bFGF can be obtained (as in LYO VI). The concentration of bFGF was found to be 36-127 pg/ml which corresponds to about $5.4\times10^{-9}$-$1.95\times10^{-8}$ pg bFGF per platelet used as the starting material.

These findings paved the way to prepare an extract according to the invention. The extract of the invention comprises one or more of the following features: comprises proteins having growth and/or trophic factors e.g. TGF-b1, b-FGF, VEGF, and PDGF-AB with a more balanced composition as compared to other platelet factor mixtures known in the art; is double viral inactivated e.g. S/D treated and pasteurized; has reduced aggregate content; comprises a proportion of factors that is similar to the physiological proportion of the same factors; comprises a physiological balanced proportion between TGF-b1, VEGF, and PDGF-AB; and exhibits reduced plasma impurities (e.g. reduced IgG and fibrinogen levels).

The term "physiologically balanced proportion" refers, for example, to a proportion between PDGF-AB:TGF-b1 and/or between PDGF-AB:VEGF that is similar to the proportion of these factors in a physiological composition of platelets, concentrated platelets, pooled platelets, platelets leukocyte reduced, pooled platelets leukocyte reduced, washed platelets, washed aphaeresis platelets leukocyte-reduced (WAP) preparation, platelet extract, Platelet Rich Plasma releasate (PRP-R), serum, and/or platelet releasate. "Serum" typically refers to blood plasma without fibrinogen or other clotting factors that contain growth/trophic factors released by activated platelets. In the case of serum, the physiological ratio can be calculated according to growth/trophic factor values present in the serum (according to package inserts of commercial ELISA kits). In such an example, the physiological ratio between PDGF-AB:TGF-b1 and PDGF-AB:VEGF was found to be 0.5 and 90.9, respectively.

In one embodiment, the physiological ratio between PDGF-AB:TGF-b1 in WAP (starting material) is at least 0.2 or in the range of about 0.2 to about 0.5, such as about 0.2, 0.3, 0.36, 0.4, 0.44 and 0.47.

In another embodiment, the physiological ratio between PDGF-AB:VEGF in WAP (starting material) is at least 45 or in the range of about 45 to about 103, such as about 45, 64, 73, 76, and 103.

In one embodiment of the invention, the extract according to the invention comprises a ratio for PDGF-AB:TGF-b1 that is at least 0.2; and/or for PDGF-AB:VEGF that is at least 45.

In one embodiment of the invention, the extract according to the invention comprises a ratio for PDGF-AB:TGF-b1 that is at least about 0.56; and/or for PDGF-AB:VEGF that is at least about 74 (as in LYO VII).

The extract according to the invention has one or more of the following advantages: is standardized and allows robust (consistent) biological performance; exhibits biological activity e.g. induction of proliferation and/or morphological changes in cells; exhibits increased activity with low concentrations of PDGF-AB as compared to the concentration of recombinant PDGF-AB alone therefore the likelihood of transformational changes in non proliferative tissue is decreased; has optimal viral safety; has improved immunological safety e.g. since it comprises low levels of plasma impurities relative to an extract prepared from platelet-enriched fractions which were not subjected to a step of plasma proteins removal e.g. a washing step; and is non clottable.

The term "viral-safe platelet extract" refers to an extract which was subjected to at least two orthogonal viral inactivation treatments.

"At least two orthogonal viral inactivation treatments" involves carrying out at least two different and independent treatments for inactivating viruses. A combination of two or more of the following non limiting treatment examples can be used: pasteurization, Solvent/Detergent (S/D), nanofiltration, Low pH treatment, UV irradiation and Sodium thiocyanate treatment.

The term "inactivating viruses or viral inactivation" refers to a situation wherein viruses are maintained in the solution but are rendered non-viable e.g. by dissolving their lipid coat; and/or to the situation wherein viruses are physically removed from the solution e.g. by size exclusion techniques.

The term "platelet extract" refers to a mixture comprising platelet-derived factors. Typically, extracts are cell free.

The term "lysate" refers to a solution produced when cells are destroyed by disrupting their cell membranes.

The term "active platelet extract" refers to a platelet extract which comprises biologically active substances such as growth factors and/or trophic factors and exhibits biological activity including, but not limited to, induction of cell proliferation cell motility, cell-cell interactions, and/or cellular morphological changes.

The term "platelet extract derived from multiple donors" refers to a platelet extract which is prepared from at least two individuals. The individuals can be human or other mammalians.

The term "growth factor" typically refers to an agent that promotes cellular growth, proliferation and/or differentiation. Examples of growth factors include, but are not limited to, transforming growth factor (TGF) e.g. TGF-b1, fibroblast growth factor (FGF) e.g. bFGF, vascular endothelial growth factors (VEGF), platelet-derived growth factor (PDGF) e.g. PDGF-AB, and the like.

The term "trophic factors" typically refers to an agent that stimulates differentiation and/or survival of cells. Examples of trophic factor include, but are not limited to, adhesion molecules, bone morphogenetic proteins, cytokines, eph receptor tyrosine kinase, epidermal growth factors, fibroblast growth factors (FGF), GDNF, heparin-binding growth factors, insulin-like growth factors, neurotrophins, semaphorins, transforming growth factors (TGF) β, tyrosine kinase receptor ligands, and the like.

A platelet factor may have growth activity and trophic activity.

The term "aggregates" refers to a chunk of material which contains solids such as protein aggregates. Protein aggregation can be encountered during manufacture of biotherapeutics (Protein aggregation and bioprocessing. Cromwell M E, Hilario E, Jacobson F. AAPS J. 2006 Sep. 15; 8(3):E572-9. Review). Aggregates of proteins may be in the form of soluble/insoluble, covalent/noncovalent, reversible/irreversible, and/or native/denatured proteins. If desired, e.g. for intravenous administration, aggregates may be removed from the extract by different techniques known in the art e.g. by centrifugation; filtration; preparative size exclusion chromatography (SEC); ultrafiltration e.g. using 100 KD polyethersulfone (PES) membrane, 100 KD polyvinylidene fluoride (PVDF) membrane, 300 KD PES membranes, polypropylene membranes, cellulose acetate membranes and/or by any other method known in the art.

Advantageously, in one embodiment of the invention the extract exhibits low aggregate content and can be used for intravenous administration. In one embodiment of the invention, the aggregate level (turbidity) can be calculated according to the following equation:

$$\frac{OD320 \text{ platelets extract}}{\text{mg protein/ml}} - \frac{OD320 \text{ human serum albumin}}{\text{mg protein/ml}} =$$
$$OD320 \text{ platelet extract per mg protein}$$

A level in an extract which is lower than ≤0.03 $OD_{320}$ per mg protein measured as above can be considered as an extract with low aggregate content. In one embodiment of the invention, the aggregate content is in the range of from about 0.01 (limit of detection) to equal to 0.03 $OD_{320}$ per mg protein.

The term "plasma impurities" refers, for example, to thrombin; fibrinogen; fibronectin; von Willebrand factor; factor II; factor VII; factor VIII; factor IX; factor X; factor XI and IgG.

Low levels of plasma impurities refers, for example, to undetectable levels of physiological active thrombin (by clotting time); undetectable levels of physiological active fibrinogen (by clotting time); less than about 0.13 or less than about 0.034 mg/ml fibrinogen (by ELISA); less than about 0.004 or 0.001 mg/ml fibronectin; undetectable levels of physiological active von Willebrand factor; less than about 0.0013 or 0.0014 IU/ml factor II; less than about 0.008 or 0.009 IU/ml factor VII; undetectable levels of physiological active factor VIII; undetectable levels of physiological active factor IX; less than about 0.003 IU/ml factor X; undetectable levels of physiological active factor XI and factor II; and less than about 0.076 or 0.011 mg/ml IgG. In one embodiment of the invention, fibrinogen concentration (by ELISA) is in the range of 0.01 to 0.1 mg/ml; fibronectin concentration is in the range of 0.002 to 0.02 mg/ml; factor VII concentration is in the range of 0.001 to 0.01 IU/ml; factor X concentration is in the range of 0.001 to 0.01 IU/ml; and IgG concentration is in the range of 0.01 to 0.1 mg/ml. An extract exhibiting undetectable levels of clotting factors and/or protein plasma impurities is considered to be depleted of these factors/proteins.

"Solvent detergent (S/D) viral inactivation treatment" typically refers to a process that inactivates enveloped or lipid-coated viruses by destroying their lipid envelope. The treatment can be carried out by the addition of detergents (such as Triton X-45, Triton X-100 or Tween 80) and solvents [such as tri(n-butyl)phosphate (TnBP), di- or tri-alkylphosphates].The solvent-detergent combination used to deactivate lipid coated viruses may be any solvent-detergent combination known in the art such as TnBP and Triton X-100; Tween 80 and Sodium cholate and other combinations.

The concentration of the solvent(s) detergent(s) used can be those commonly used in the art, for example as carried out in U.S. Pat. No. 5,094,960A, U.S. Pat. No. 4,789,545A. In one embodiment of the invention, a combination of >0.1% TnBP and >0.1% Triton X-100 is used. In another embodiment of the invention a combination of 1% Triton X-100 and 0.3% TnBP is used. Typically, the conditions under which the solvent-detergent inactivates the viruses consist of 10-100 mg/ml of solvent detergent at a pH level ranging from 5-8, and a temperature ranging from 2-37° C. for 30 minutes to 24 hours. However, other solvent detergent combinations and suitable conditions will be apparent to any person versed in the art.

"Pasteurization" typically refers to a process by which heat destroys both lipid-enveloped and non-enveloped viruses. "Pasteurization" is interchangeable with the term "heat inactivation". The heat inactivation can be carried out at a temperature in the range of 59.5 to 60.5° C. for a period of 9 to 10.5 hours e.g. the inactivation can be carried out at 60° C. for 10 hours. Stabilizers such as sucrose and glycine can be added into the platelet lysate during the pasteurization step.

"Nanofiltration" typically refers to a process by which lipid-enveloped and non-enveloped viruses are excluded from the sample by using nanometer-scale filters such as Planova™ 20N, 35N and 75N; Viresolve/70™, Viresolve/ 180™. The filters can have a pore size of less than 70 nm, preferably between 15 and 50 nm. However, any membrane having a pore size sufficient to reduce or eliminate viruses from the sample can be employed in nanofiltration. Viruses removed by nanofiltration can be enveloped [e.g. HIV, hepatitis B virus, hepatitis C virus, West Nile Virus, cytomegalovirus (CMV), Epstein-Barr virus (EBV), herpes simplex virus], and non enveloped (e.g. hepatitis A virus, paravirus B19, Polio virus).

Low pH treatment is typically effective against enveloped viruses. In one embodiment of the invention, the platelet lysate is subjected to a low pH, typically to a pH of 4, and lasts anywhere between 6 hours and 21 days. "Low pH treatment" is interchangeable with the term "acidic pH inactivation".

The term "mixture of active platelet cell growth factors and/or trophic factors" refers to a composition comprising at least 4 different platelet derived factors e.g. growth and/or trophic factors. In one embodiment of the invention the factors are TGF-b1, b-FGF, VEGF, and PDGF-AB.

Typically, the extract of the invention is non clottable and exhibits low levels of plasma impurities e.g. low IgG and/or low fibrinogen levels. Such as less than 3 mg/ml IgG and less than 0.98 mg/ml fibrinogen, such as e.g. equal or less than about 0.076 mg/ml IgG and equal or less than about 0.034 mg/ml fibrinogen.

The term "non clottable" refers to a platelet extract which is not capable of generating a clot solely upon mixing of the extract with an activating agent, such as thrombin. "An activating agent" refers to an agent that is capable of forming fibrin from fibrinogen such as thrombin and/or a solution obtainable from snake venom.

The invention provides viral safe platelet extracts that comprise proteins having growth and/or trophic factors (e.g. TGF-b1, b-FGF, VEGF, and PDGF-AB) with more balanced composition as compared to other platelet factor mixtures.

A "more balanced composition" refers to a composition that is obtained from multiple donors and comprises at least four different proteins having growth factor activity and/or trophic factor activity such as TGF-b1, b-FGF, VEGF, and PDGF-AB and in which one or more platelet factors e.g. PDGF-AB and/or bFGF are enriched. An extract enriched with PDGF-AB may e.g. comprise at least 3 fold higher PDGF-AB amounts, e.g. about 3, 3.5, 4, 4.5, 5, 5.5, 6, 6.5, 7, 7.5, 8 or more, than the extract subjected to S/D and S/D removal by HIC in the absence of a wash with a non isocratic solution. An extract enriched with PDGF also relates e.g. to an extract which comprises amounts/levels of PDGF-AB that are similar to the amounts of PDGF-AB of the equivalent material prior to the S/D treatment or after the S/D treatment and prior to S/D removal e.g. by HIC or comprises amounts of PDGF-AB similar to the amounts in the lysate of the staring material. PDGF-AB enrichment can be obtained by increasing the recovery of PDGF-AB in a purification and/or chromatography step. In one embodiment, the enrichment of PDGF-AB is obtained by increasing the recovery of PDGF-AB during the S/D removal in the HIC step by adding a wash with a non isocratic solution. Thus, the method according to the invention allows obtaining a platelet extract with high yields of PDGF-AB.

An extract enriched with bFGF may e.g. comprise at least 1.8 fold higher bFGF amounts, e.g. about 2, 2.5, 3, 3.5, 4, 4.5, 5, 5.5, 6, 6.5, 7, 7.5, 8 or more, than the same extract subjected to S/D and S/D removal by HIC, in the absence of a wash with a non isocratic solution. An extract enriched with bFGF also relates e.g. to an extract which comprises amounts of bFGF that are similar to the amounts of bFGF of the equivalent material prior to the S/D treatment or after the S/D treatment and prior to S/D removal e.g. by HIC or comprises amounts of bFGF similar to the amounts in the lysate of the staring material. bFGF enrichment can be obtained by increasing the recovery of bFGF in a purification and/or chromatography step. In one embodiment, the enrichment of bFGF is obtained by increasing the recovery of bFGF during the S/D removal in the HIC step by adding a wash with a non isocratic solution. Thus, the method according to the invention allows obtaining a platelet extract with high yields of bFGF.

The platelet extract according to the invention can be used for any therapeutic purpose.

The extract of the invention is suitable e.g. for promoting healing of injured tissue in a subject. The platelet extract can be used as is for injection into a target area or for intravenous administration; applied onto/administered into bandages, foams, pads and matrices and/or can be used in combination with fibrin sealant for topical applications. The extract can be released into/onto a desired location from different delivery agents such as bandages, pads, foams and matrices. The agents can be made of natural and/or synthetic materials. Examples of such materials include, but are not limited to, polymers, hydrogels, Polyvinyl alcohol (PVA), polyethylene glycol (PEG), hyaluronic acid, chondroitin sulphate, gelatin, alginate, collagen matrices, carboxymethylcellulose, dextran, poly(2-hydroxyethylmethacrylate) [PHEMA], agar, oxidize regenerated cellulose (ORC), self assembled peptides [SAPs], poly(glycolic) acid, poly(lactic) acid, fibrin and combinations thereof.

It was found according to the invention that using the extract according to the invention in combination with fibrin sealant in the Subcutaneous Implantation Model in Rats [commonly used to assess tissue response, angiogenesis and overall healing in the implanted tissue-International Organization for Standardization (ISO) 10993-6, Biological Evaluation of Medical Devices—Part 6: Tests for Local Effects After Implantation (2007)] resulted in more angiogenesis and better overall healing 7 days post-implantation as compared to using fibrin sealant alone or saline. The extract was used in two different doses and the following are the amounts of several growth factors actually administered: TGF-b1 5.27 or 52.7; PDGF-AB 0.1 or 1.05; bFGF 0.0024 or 0.024; and VEGF 0.023 or 0.23, ng (administered with 200 µl fibrin sealant). It was shown that the beneficial effect of the extract was dose dependent.

It was also found that the extract according to the invention had no deleterious effect as microscopically determined by the presence of low numbers of macrophages and lymphocytes in the implant site.

The term "subject", as used herein, includes animals of mammalian origin, including humans. In one embodiment, the subject is a patient.

The term "any therapeutic purpose" refers to any curative or preventive treatment; for cosmetic use; and/or for any disease, disorder or condition in a subject. Exemplary therapeutic purposes include, but are not limited to, accelerating internal or external wound healing, i.e., causing the wound to heal rapidly as compared to an untreated wound or to other known wound treatments; treating any injury or condition that requires stimulating angiogenesis, mitogenesis, cell proliferation, neutrophils and macrophages, collagen synthesis, migration, wound contraction, extracellular matrix synthesis, epithelialization and chemotaxis; injury or condition that requires tissue generation, regeneration or reorganization, epithelialization, formation of new blood vessels, or angiogenesis; for decreasing scar formation; reducing post operative complications and morbidity; for healing skin wounds e.g. cuts or ulcers.

The platelet extract can be used in various surgical fields such as, but not limited to, orthopedic surgery (e.g. bone repair, articular cartilage repair, knee arthroplasty, lumbar spinal fusion, and in intervertebral disc degeneration); dental surgery; dentistry and maxillofacial surgery (e.g. consolidation of titanium implants, maxillary sinus augmentation and bone remodeling); for muscle, tendon and ligament repair; facial plastic and reconstructive surgery; chronic skin wound healing, skin burn healing, ophthalmology; facial nerve regeneration, peripheral nerve repair, central nervous system (CNS) repair (spine and/or brain surgery), optic nerve repair, nerve compression syndrome repair, cranial nerve repair, sciatic nerve repair; cardiac and bariatric surgery.

The extract can be administered onto a surface of a body part of a patient. The term "surface" refers to an external surface that can be seen by unaided vision and to a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; and the cardiac muscle. The surface can be a bleeding or a non-bleeding site. Alternatively, the extract can be administered by injection e.g. intradermally, intraperitonealy, subcutaneously, intrathecally, intrasternally, intracranialy, intramuscularly, and/or intravenously. The extract can also be administered by infusion.

The term "a therapeutically effective amount" refers to the dose required to prevent or treat (relieve a symptom or all of the symptoms) a disease, disorder or condition. The effective amount can be measured based on any change in the course of the disease in response to the administration of the composition. The effective dose can be changed depending on the age and weight of the subject, the disease and its severity (e.g. early or advanced stage) and other factors which can be recognized by the skilled in the art.

The extract can also comprise a pharmaceutically acceptable excipient. As used herein the term "excipient" refers to an inert substance which is added into the extract. The excipients can be added, for example, in order to ensure that the active substances retain their chemical stability and/or biological activity upon storage, to aid the manufacturing process and/or for aesthetic reasons e.g. color. The added excipient is generally safe and non-toxic.

The platelet extract according to the invention can be used in combination with a surgical sealant. Different types of surgical sealants can be used in combination with the platelet extract, including, but not limited to, a biological sealant (such as a fibrin sealant prepared with fibrinogen and thrombin components); a synthetic sealant such as acrylates, cyanoacrylates, and polyethylene glycol (PEG) polymers; and a semisynthetic sealant e.g. made from a combination of biological and synthetic materials such as gelatin-formaldehyde-resorcinol (GFR) glue. In one embodiment of the invention, the platelet extract is used in combination with fibrin sealant components. In another embodiment of the invention, the platelet extract is used with a synthetic sealant.

The invention provides a kit. The kit may comprise a recipient comprising the extract according to the invention. The extract can be in a solid form, as a solution or in frozen form. In the case that the extract is provided in solid form, the kit can further comprise a recipient with a pharmaceutically acceptable carrier for reconstituting the solid extract. The kit may further comprise one or more syringes and/or syringe needles for injection the extract to the patient. The kit can comprise instructions for use. The instructions may describe how to administer the extract to a patient. The invention also relates to a kit comprising recipients containing the components of the fibrin sealant or the synthetic sealant, a recipient containing the extract of the invention and instructions for use. Optionally, the extract of the invention can be in the recipient of one component of the fibrin sealant. Also, the invention relates to a kit comprising a recipient containing the lyophilized extract, a recipient containing a reconstitution solution or carrier and instructions for use.

The fibrin sealant components can be prepared from blood compositions. The blood composition can be whole blood or blood fractions, i.e. a product of whole blood such as plasma.

In one embodiment of the invention, the fibrinogen component is comprised from a biologically active component (BAC) which is a solution of proteins derived from blood plasma which can further comprise tranexamic acid and arginine or lysine or mixtures or arginine and lysine, or their pharmaceutically acceptable salts. BAC can be derived from cryoprecipitate, in particular concentrated cryoprecipitate. The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitated supernatant that contains fibrinogen and factor XIII. The precipitate can be collected, for example by centrifugation. The solution of BAC comprises further Factor VIII, fibronectin, von Willebrand factor (vWF), vitronectin, etc. for example as described in U.S. Pat. No. 6,121,232 and WO9833533.

The composition of BAC can comprise stabilizers such as arginine hydrochloride. Typically, the amount of fibrinogen in BAC is in the range of from about 40 to about 60 mg/ml. The amount of tranexamic acid in the solution of BAC can be from about 80 to about 110 mg/ml. The amount of arginine hydrochloride can be from about 15 to about 25 mg/ml.

Optionally, the solution is buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml.

In another embodiment, the concentration of plasminogen and plasmin in the BAC composition is lowered to equal or less than 15 µg/ml like for example 5 mg/ml or less plasminogen e.g. using a method as described in U.S. Pat. No. 7,125,569 and WO02095019. In this case addition of tranexamic acid, aprotinine or any other fibrinolytic inhibitors into the BAC is not needed.

It is also possible that the fibrin sealant comprises components which encourage the formation of the clot, such as $Ca^{2+}$, Factor VIII, fibronectin, vitronectin, von Willebrand factor (vWF) which can be provided as a separate component or formulated with the fibrin sealant components.

Fibrin sealant components derived from blood compositions are typically purified from infective particles. The purification procedure can be carried out by nanofiltration; solvent/detergent treatment and/or by any other method known in the art.

The term "infective particle" refers to a microscopic particle, such as micro-organism or a prion, which can infect or propagate in cells of a biological organism. The infective particles can be viral particles.

The platelet extract prepared according to the invention can be used in combination with various cell types e.g. fibroblast and stem cells e.g. endothelial stem cells e.g. HUVEC. The cell type can be determined according to the intended therapeutic use. For example, for regeneration of intervertebral disc, a cell composition comprising notochordal-derived cells can be used. For induction of angiogenesis, endothelial stem cells can be used.

The platelet extract of the invention can be prepared by a method including at least two different viral inactivation treatments and comprises the following steps: obtaining platelet-enriched fractions from multiple donors; lysing the platelets; carrying out a Solvent-Detergent (S/D) viral inactivation treatment; removing the S/D by hydrophobic interaction chromatography (HIC); and conducting a second orthogonal viral inactivation treatment e.g. pasteurization. The HIC comprises the steps of: loading the lysate to HIC, and collecting a fraction eluted under non isocratic conditions.

Loading the lysate to HIC can be carried out by contacting the lysate with the HIC resin that is packed within a column.

The term "contact between the lysate and the HIC resin" is used in its broadest sense and refers, for example, to any type of combining action which brings the lysate into sufficiently close proximity with the resin such that a binding interaction will occur between the S/D material present within the lysate and the resin.

The invention provides a method for the preparation of a viral-safe platelet extract which comprises at least two orthogonal viral inactivation treatments, the method comprising the steps of: providing platelet-enriched fractions from multiple donors; preparing a platelet lysate; carrying out a solvent detergent (S/D) viral inactivation treatment e.g. in an aggregate-reduced lysate; removing the S/D by HIC comprising the steps of loading the lysate to HIC, and collecting unbound materials and a fraction eluted under non isocratic conditions; and conducting a second orthogonal virus inactivation treatment.

Fractions from which the platelet-enriched material can be obtained include, but are not limited to, blood fractions, plasma fractions, washed and leukocyte-reduced platelets from aphaeresis, and platelets from aphaeresis. In one embodiment, washed and/or leukocyte-reduced platelets pooled from multiple donors is used as the starting material for preparation of the platelet extract.

Advantageously, using washed platelets as the starting material enables obtaining a non-clottable platelet extract with reduced plasma impurities as defined above.

Typically, the term "platelet starting material" relates to platelet-enriched fractions obtained from multiple donors for use in the method of the invention. The platelet-enriched fractions can be, for example, separated from units of whole blood, from blood fractions and/or from plasma fractions. The platelet-enriched fractions can be obtained from aphaeresis donations. The starting material can be washed and/or leukocyte-reduced. In one embodiment of the invention, the platelet-enriched fractions are washed and leukocyte-reduced and are obtained from aphaeresis donations. In one embodiment, the minimal number of platelets in an aphaeresis leukocyte-reduced collected unit is about or more than $3.0 \times 10^{11}$ as specified in the "Circular of Information for the Use of Human Blood and Blood Components".

The term "washed platelets" refers to platelets which were subjected to a washing step. During the washing procedure there can also be losses of platelets. The washing can be carried out using 0.9% Sodium Chloride with or without small amounts of dextrose. The washing procedure can be carried out as elaborated in the "Circular of Information for the Use of Human Blood and Blood Components". In one embodiment of the invention, the washing is carried out as follows: a platelet material unit is centrifuged under gentle conditions. Then, the supernatant is discarded and the platelet pellet is washed at least twice (with centrifugation between the washes) with saline under gentle conditions. The washed and re-suspended platelets can be frozen until used in the method of the invention.

The term "leukocyte-reduced" refers to a content of leukocyte which is lower than the content of leukocyte in whole blood (content in whole blood is about 1 to $10 \times 10^9$ white cells per blood unit). Any leukocytes reduction methods, e.g. by filtration, can be used to obtain a leukocyte-reduced unit. The reduction in leukocytes can be carried out during aphaeresis. In one embodiment of the invention, a unit of platelets which contains less than about $8.3 \times 10^5$ leukocytes is used as the starting material for the preparation of the platelet extract. In another embodiment, a leukocyte-reduced unit of platelets which contains less than about $5 \times 10^6$ leukocytes is used as the starting material for the preparation of the platelet extract.

The term "aphaeresis" typically refers to the withdrawal of blood from a single donor, with a portion (e.g. platelets) being separated and retained and the remainder retransfused into the donor. One unit of aphaeresis platelets obtained from a single donor can contain about or higher than $3.0 \times 10^{11}$ platelets. In one embodiment of the invention, one unit of aphaeresis platelets obtained from a single donor contains up to $6.0 \times 10^{11}$ platelets.

Lysis of the platelets and release of the factors (e.g. various platelet growth factors and/or trophic factors) entrapped in the platelets, can be carried out by freezing and thawing the platelets enriched fractions, by S/D treatment, by sonication [Slezak et al., (1987) J. Exp. Med. V166 p 489-505], by French press [Salganicoff et al., (1975) Biochem. Biophys. Acta v385 p 394-411] and/or by any other method known in the art. In one embodiment of the invention, lysis of the platelets is carried out by freezing and thawing the platelets enriched fractions followed by carrying out an S/D treatment. Typically, lysis of the platelets produces a cell free platelet lysate.

In one embodiment of the invention, the first viral inactivation step of the extract preparation comprises solvent-detergent (S/D) treatment of the platelets for eliminating enveloped viruses. The S/D treatment also promotes lysis of the platelets and release of their content into the solution. For optimal envelope viral inactivation, a sub-step including aggregates removal (e.g. by filtration) is carried out during the S/D treatment step.

The term "S/D removal (solvent-detergent removal)" refers to the removal of the bulk of the solvent-detergent used in the S/D treatment. The removal of solvent-detergent comprises using hydrophobic interaction chromatography column (HIC) e.g. C-18 silica packing material and SDR (Solvent-Detergent removal) HyperD. The S/D removal can further comprise a step of oil extraction. In one embodiment of the invention, SDR HyperD, which is a chromatographic packing made of silica beads in which the pore volume is filled with a three-dimensional cross-linked hydrophobic acrylic polymer, is used to remove the solvent-detergent. The SDR HyperD advantageously involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125]. It was found according to the invention that better results were obtained using SDR+ elution conditions as compared to C-18+ elution conditions. In one embodiment, increased PDGF-AB recoveries were obtained using SDR+elution conditions.

HIC refers e.g. to a column packed with a hydrophobic polymer resin matrix.

The hydrophobic interaction chromatography can be carried out by loading to the HIC column the S/D treated lysate in a binding buffer. The column can be equilibrated prior to loading the S/D treated lysate e.g. by washing the column with the binding buffer. The term "equilibrate" refers to allowing and/or adjusting the column to reach a specific buffer condition such as a specific pH level and ionic strength. In one embodiment, the adjustment of the column is carried out by washing the column with an equilibration buffer having a predetermined pH level and ionic strength prior to loading the S/D treated lysate onto the column. In one embodiment of the invention, the equilibration buffer comprises 20 mM sodium acetate and 10 mM glycine at pH 6.8-7.4 and 5% (v/v from the total volume) human serum albumin (HSA). In another embodiment of the invention, the equilibration buffer comprises 20 mM sodium acetate and 10 mM glycine at pH 6.8-7.4 and 1% human serum albumin (v/v from the total volume). In another embodiment of the invention, the equilibration buffer comprises 20 mM sodium acetate and 10 mM glycine at pH 6.8-7.4 and 0.2% human serum albumin (v/v from the total volume). Yet in another embodiment of the invention, the equilibration buffer comprises 20 mM sodium acetate and 10 mM glycine at pH 6.8-7.4, 0.2% human serum albumin (v/v from the total volume) and 1% dextran sulfate (w/w from the total weight). The equilibration buffer can comprise HSA in a concentration range from about 0.2 to about 5% (v/v from the total volume).

The term "binding buffer" refers to the buffer used during loading of the S/D treated lysate onto the chromatography column. Oftentimes, the equilibration buffer used to adjust the column prior and/or during loading the lysate is termed binding buffer. In one embodiment of the invention, the binding buffer comprises 20 mM sodium acetate and 10 mM glycine at pH 6.8-7.4 and 5% (v/v from the total volume) human serum albumin. In another embodiment, the binding buffer comprises 20 mM sodium acetate and 10 mM glycine at pH 6.8-7.4 and 1% human serum albumin (v/v from the total volume). In another embodiment, the binding buffer comprises 20 mM sodium acetate and 10 mM glycine at pH 6.8-7.4 and 0.2% human serum albumin (v/v from the total volume). Yet in another embodiment, the binding buffer comprises 20 mM sodium acetate and 10 mM glycine at pH 6.8-7.4, 0.2% human serum albumin (v/v from the total volume) and 1% dextran sulfate (w/w from the total weight). The binding buffer can comprise HSA in a concentration range from about 0.2 to about 5% (v/v from the total volume).

The term "unbound material" typically refers to the fraction collected following washing of the loaded column with the same buffer used for equilibration and/or the buffer used for loading the S/D treated extract onto the column ("binding buffer"). Advantageously, in the S/D removal step, using HIC, after washing the column and collecting unbound material, a non-isocratic solution is used to increase the recovery of certain growth factors, e.g. PDGF-AB and bFGF; to obtain a more balanced composition and/or an extract having a physiologically balanced proportion. In this regard, S/D removal in the S/D treated lysate is carried out by loading the S/D treated lysate onto HIC in a binding solution, washing with an isocratic solution, collecting the unbound material containing the lysate substantially without the S/D and next collecting PDGF-AB, and perhaps other factors e.g. bFGF, bound to the HIC resin by using elution conditions. The most common elution conditions employ a shift in the composition of the mobile phase or a non-isocratic solution so the factors e.g. PDGF-AB binding environment created by the binding solution is lost.

In one embodiment of the invention, PDGF-AB is 3-fold enriched, during S/D removal employing HIC, by eluting PDGF-AB bound to the HIC resin using non isocratic elution conditions.

The term "elution conditions" refers to using a non-isocratic condition e.g. a solution or condition different from the solution or condition used to load and/or equilibrate the column, and/or different from the solution used in a previous step. The elution conditions are such that S/D substantially remains bound to the column whereas the factors are eluted. The method according to the invention comprises at least one elution step with a non isocratic solution.

Elution conditions, typically involves an increase in salt concentration. It was found that when using a C-18 resin, a positive correlation exists between NaCl concentration in the elution buffer and PDGF-AB recovery following HIC using a concentration ranging from 0.3 M up to 1M NaCl. Improved results were obtained at a concentration of 1 M (about 30% PDGF-AB recovery). When using SDR resin, similar PDGF-AB recoveries were obtained in all NaCl tested concentrations of 0.7 and 1.5 M.

A further improvement in the elution conditions for PDGF-AB was obtained by adding an organic solvent to the buffer in combination with an increase in salt concentrations. Optimal elution conditions are such that S/D substantially remains bound to the column whereas most of the factors are eluted.

It was found according to the invention that a high PDGF-AB recovery was obtained with lower than 1 M NaCl and/or lower than 20% ethanol in both C-18 and SDR resins without substantially affecting SD removal.

It was found according to the invention that increased elution for b-FGF was obtained by adding in the buffer, in addition to ethanol and NaCl, a molecule capable of binding b-FGF e.g. heparin. Optimal results were obtained for PDGF-AB and b-FGF recovery when incubating the lysate with a molecule capable of binding growth/trophic factors (e.g. dextran sulfate) prior to the S/D removal step and carrying out the S/D removal step in the presence of such molecule.

In one embodiment of the invention, the elution solution employed is different from the binding buffer e.g. different from a solution containing 20 mM sodium acetate, 10 mM glycine and 0.2% human serum albumin; different from a solution containing 20 mM sodium acetate, 10 mM glycine and 1% human serum albumin and/or different from a solution containing 20 mM sodium acetate, 10 mM glycine and 5% human serum albumin. In another embodiment of the invention, the elution solution comprises components other than sodium acetate, glycine and human serum albumin. In another embodiment of the invention, the elution solution comprises components other than 20 mM sodium acetate, 10 mM glycine and 0.2% human serum albumin. In another embodiment, the elution buffer comprises an organic solvent, a salt, and/or a molecule that binds growth/throphic factor(s). In another embodiment, the elution buffer comprises ethanol e.g. at a concentration from 10-12.5%, NaCl e.g. at a concentration of 0.5M-1M, heparin e.g. at a concentration of 5 IU/ml and/or dextran sulphate e.g. at a concentration of 0.1-1%. In another embodiment, the elution solution comprises 20 mM sodium acetate, 10 mM glycine, 10% ethanol, 1M NaCl, and 0.2% human serum albumin. In another embodiment, the elution solution comprises 20 mM sodium acetate, 10 mM glycine, 12.5% ethanol, 0.5M NaCl, and 0.2% human serum albumin. In another embodiment, the elution solution comprises 20 mM sodium acetate, 10 mM glycine, 12.5% ethanol, 0.5M NaCl, 5 IU/ml Heparin and 0.2% human serum albumin. In another embodiment, the elution solution comprises 20 mM sodium acetate, 10 mM glycine, 1% dextran sulfate and 0.2% human serum albumin. In another embodiment, the elution solution comprises 20 mM sodium acetate, 10 mM glycine, 12.5% ethanol, 0.5M NaCl, 0.1% dextran sulfate and 0.2% human serum albumin. Yet in another embodiment, the solution comprises 20 mM sodium acetate, 10 mM glycine, 1% dextran sulfate and 0.2% HSA. In one embodiment of the invention, the method comprises more than one elution step. In such case the elution solution is different from the solution used in a previous step and can be the same as the binding buffer.

In one embodiment of the invention, the non isocratic solution is acetate glycine buffer (e.g. 20 mM sodium acetate and 10 mM glycine at pH 6.8-7.4) containing from 5% to 15% ethanol, from 0.2M to 1.2M NaCl, and from 0.1% to 1.0% HSA e.g. 0.2% HSA. Other possible salts are, but not limited to, KCl, $MgCl_2$, $CaCl_2$. Other possible solvents are, but not limited to, isopropanol, glycerol, ethylene glycol.

It was found according to the invention that by carrying out two elution steps I—with acetate glycine buffer (20 mM sodium acetate and 10 mM glycine at pH 6.8-7.4) containing 12.5% ethanol, 0.5M NaCl, 5 IU/ml Heparin [a molecule that binds growth/trophic factor(s)], and 0.2% HSA; and II—with acetate glycine buffer (20 mM sodium acetate and 10 mM glycine at pH 6.8-7.4) containing 10% ethanol, 1M NaCl and 0.2% HSA, at least 3-fold recovery or enrichment of PDGF-AB can be obtained and about 1.8-fold recovery or enrichment of bFGF can be obtained (as in LYO VI) as compared to a preparation obtain in the absence of such elutions steps.

In one embodiment of the invention, a two step elution with a non isocratic condition is carried out. In another embodiment of the invention the non isocratic solution used in at least one of the steps, e.g. the first step, comprises a molecule that binds growth factors such as heparin at a concentration range of 2 to 30 IU/ml, 2-25 IU/ml, 2-20 IU/ml, 2-15 IU/ml, 2-10 IU/ml, or 2-5 IU/ml. In one embodiment of the invention, the non isocratic solution comprises heparin at a concentration of 5 IU/ml.

It was also found according to the invention that by adding a step of incubation with dextran sulphate at a final concentration of 1% (w/w) [a molecule that binds growth/trophic factor(s)] after S/D treatment and prior to S/D removal step, and by carrying out two elution steps, one with acetate glycine buffer (20 mM sodium acetate and 10 mM glycine at pH 6.8-7.4) containing 12.5% ethanol, 0.5M NaCl, 0.1% dextran sulfate and 0.2% HSA, and another with 1% dextran sulfate and 0.2% HSA in acetate glycine buffer during S/D removal step, about 6.6-fold recovery or enrichment of PDGF-AB, and about 2.8-fold recovery or enrichment of bFGF can be obtained (as in LYO VII) as compared to preparations obtained without such elutions. By these elution steps, the recovery of bFGF can be increased to 85% and the recovery of PDGF-AB can be increased to 88% as compared to concentrations of the factors prior to S/D removal by HIC.

Surprisingly, the overall recovery of PDGF-AB (from the starting material, WAP) in LYO VII was 51% compared with the overall recovery of PDGF-AB of 1.5% in LYO VI. The overall recovery of VEGF in LYO VII was 73% compared to 37% in LYO VI.

In one embodiment of the invention, the method of the invention further comprises the step of contacting the lysate with a molecule that binds factors e.g. growth factors prior to the S/D removal step. The molecule that binds factors can be e.g. dextran sulphate at a final concentration range of 0.01 to 1% e.g. at a concentration of 1% (w/w). In such an embodiment, the binding buffer comprises dextran sulphate in addition to sodium acetate, glycine, and human serum albumin. In another embodiment of the invention, the non isocratic solution comprises dextran sulphate at a final concentration of 0.1% (w/w).

It was found according to the invention that the sequence of elution solutions plays a role in the recovery level of PDGF-AB and b-FGF. Namely, factor recoveries can vary when different non isocratic solutions are used and/or when the elution order is changed or reversed.

The molecule can be heparin, dextran sulphate, heparan sulfate, and other sulfated polysaccharides, glycosaminoglycans, or polyanions, and the like to which growth/trophic factors can bind upon contact.

The term "contact between the molecule and the factor" is used in its broadest sense and refers to any type of combining action which brings the molecule into sufficiently close proximity with the factors of interest present in the lysate such that a binding interaction will occur between the chemical compound and the factors. Contacting can be carried out in a different ways, including, but not limited to, introducing the compound into the lysate.

Advantageously, contacting the lysate with a molecule that binds growth factors and/or trophic factors prior to S/D removal step results in an increase/enrichment in the amounts of several factors e.g. PDGF-AB, bFGF.

In another aspect, the invention relates to a method for removing solvent-detergent (S/D) from a biological liquid substance by hydrophobic interaction chromatography (HIC). The method comprises the steps of loading the liquid comprising S/D to HIC, collecting the unbound fraction and a fraction eluted under non isocratic conditions. Yet, in another aspect, the invention relates to a method for removing solvent-detergent (S/D) from a biological liquid substance by hydrophobic interaction chromatography (HIC). The method comprises the steps of loading the liquid comprising S/D to HIC, and collecting a fraction eluted under non isocratic conditions.

The term "biological liquid substance" or "biological liquid mixture" refer to any type of liquid substance obtained from a biological source. This typically includes, but is not limited to, preparations obtained from body fluids such as whole blood plasma or blood fractions e.g. cryodepleted plasma, cryoprecipitate, plasma or serum; semen; sputum; feces; sweat; saliva; nasal mucus; cerebrospinal fluid; a platelet derived fraction such as PRP-R; and urine, as well as liquids obtained from cell cultures, containing biological substances secreted by the cells into the preparation, or containing substances which originally were present inside the cells, and were released to the liquid preparation due to various manipulations such as the lysing of the cells.

In one embodiment, the method for removing S/D can be used during a process for viral inactivation of a biological liquid preparation. Biologically derived liquid preparations such as blood and plasma preparations are used as raw materials from which a plurality of biologically useful compounds can be purified. Examples of such compounds include immunoglobulin, factor VIII, albumin, a 1 anti trypsine, Factor IX, factor XI, PPSB, fibrinogen, and thrombin (prothrombin). In addition, various biological products such as hormones, growth factors, enzymes and ligands are isolated from biological preparations obtained from cell cultures. For example, the process of viral inactivation of a biological liquid preparation comprises the steps of:
(a) treating the biological liquid preparation with a solvent-detergent combination, at concentrations and under conditions which are sufficient to inactivate lipid-coated viruses;
(b) removing the solvent-detergent combination from the liquid preparation by passing the liquid preparation obtained in (a) on HIC; and
(c) collecting the unbound fraction and a fraction eluted under non isocratic conditions.

In another embodiment, in step (c) only the fraction eluted under non isocratic conditions can be collected.

Use of an isocratic solution typically relates to the use of a constant-composition mobile phase in liquid chromatography. A "non-isocratic solution" typically refers e.g. to a solution and/or a condition that is different from the solution and/or condition used to load and/or wash the column and/or to a solution that is different from a solution used in the previous step.

In order to remove non-enveloped viruses, at least a second viral inactivation step e.g. a heat treatment (pasteurization) can be carried out.

In certain embodiments, additional reduction in aggregate content is obtained by including in the methods of the invention a step of calcium supplementation followed by clarification filtration.

The term "calcium supplementation" refers to the addition of calcium e.g. a calcium salt into the extract/biological liquid substance. Examples of calcium salts include, but are not limited to, calcium carbonate, calcium hydroxide, calcium citrate, calcium chlorophosphate, calcium phosphate including dicalcium phosphate and tricalcium phosphate, calcium chloride or a combination thereof. Calcium can be supplemented in a final concentration range of 1 to 100 mM. In one embodiment, $CaCl_2$ is added into the extract at a final concentration of 40 mM. The extract can be incubated for 30 minutes e.g. at 25° C. while mixing at 50 RPM following the calcium supplementation.

The term "clarification filtration" refers to the removal of particles such as aggregates from the extract/biological liquid substance by filtration. A multi-filtration step can be carried out. For example, the extract can be sequentially filtered through 20, 3 and 0.45 µm filters. Sterile filtration can be carried out e.g. by 0.2 µm filter.

If desired, the platelet extract obtained by the method of the invention can be formulated with a cryoprotectant and lyophilized.

The term "cryoprotectant" refers to a substance which is added to solutions in order to retain the chemical stability and/or biological activity of the active components (e.g. growth factors and/or trophic factors) during freezing. Non limiting examples of cryoprotectant include, but are not limited to, carbohydrates such as Monosaccharides: include glucose (dextrose), fructose (levulose), galactose, and ribosedisaccharides Disaccharides: sucrose, lactose, maltose and trehalose and Disaccharides oligosaccharides another group are the poliols Sugar alcohols: Maltitol, Mannitol, sorbitol, xylitol and isomalt. Apart of carbohydrates other polymers such as Polyethylene glycol (PEG) can also be used as cryoprotectants such as polyethylene oxide (PEO) or polyoxyethylene (POE) Polyvinylpyrrolidone (PVP). Other amino acids and polyamines.

The term "lyophilization" typically refers to the process of freezing a substance and then reducing the concentration of water e.g. by sublimation to levels which do not support biological or chemical reactions. The resulting lyophilized biological material may be stored for a relatively long period of time. Following storage, the lyophilized material can be used as a powder or can be reconstituted by the addition of various volumes of an aqueous solution. The volume added during reconstitution can be similar to the volume of the solution before lyophilization, lower (resulting in a concentration of the extract compared to the volume of the starting material) or higher (resulting in a dilution of the extract compared to the volume of the starting material).

If desired, the platelet extract can be kept frozen or as solid e.g. lyophilized for prolonged storage or for use as a powder.

For example, the platelet extract obtained by the method of the invention can be kept frozen e.g. at −18° C. or at lower temperature, or as solid (e.g. lyophilized) for prolonged storage. The platelet extract can also be refrigerated e.g. at a temperature of 2° C. to 8° C.

The lyophilized extract can be used as solid or can be reconstituted in a pharmaceutically acceptable carrier prior to use. The term a "pharmaceutically acceptable carrier" refers to any diluent and/or a vehicle which is suitable for human administration or for animal administration. The carrier can be selected from any of the carriers known in the art such as, but not limited to, saline, sodium chloride solution, lactated ringers (LR), 5% dextrose in normal saline, and water for injection.

If administered with fibrin sealant, the extract can be reconstituted in one of the sealant components (thrombin or fibrinogen) or can be reconstituted separately in another diluent or vehicle.

Of advantage, the lyophilization cycle and the formulation can allow for a very fast reconstitution of the extract e.g. within fibrin sealant e.g. to facilitate hemostasis and healing which calls for an emergency use, thus in this case the reconstitution is beneficially done within seconds. In one embodiment of the invention, albumin is used in the formulation to allow fast reconstitution.

The invention is based on the following experiments and findings which exemplify the preparation of the platelet extract according to the invention, and show its activity (in in-vitro and in-vivo settings). The disclosure of applications, patents and publications, cited above or below, is hereby incorporated by reference.

The following examples are illustrative but not limiting.

EXAMPLES

Materials and Methods.

Washed aphaeresis platelets leukocyte-reduced (WAP) preparation.

Platelet material units (platelets aphaeresis leukocyte-reduced units) were collected and processed according to the "Circular of Information for the Use of Human Blood and Blood Components" (December 2009) and conformed to applicable federal statuses and regulations of the FDA and US Department of Health.

Each unit had a volume of approximately 200 ml. Each unit was drawn from a single donor who was screened and found acceptable for donation of a transfusable blood component based on FDA regulations, requirements and guidelines. Included were only units which were found non-reactive for red blood cell antibodies and negative for the following viruses by using FDA-approved kits and methods: Hepatitis B virus surface antigen; Antibody to hepatitis B virus core antigen; Hepatitis C virus antibody; Human T-cell lymphotrophic virus type 1 and 2 antibody; Human immunodeficiency virus types 1 and 2 antibody; HIV-1 by nucleic acid technology testing (NAT); HCV RNA by NAT; West Nile Virus RNA by NAT; and Serological test for syphilis. The minimal number of platelets in an aphaeresis leukocyte-reduced collected unit was as specified in the Circular of Information: $\geq 3.0 \times 10^{11}$ (the number of platelets in a single whole blood unit is $\geq 5.5 \times 10^{10}$).

All units were maintained under the recommended conditions for transfusion (see the direction for use for the blood collection, processing, and storage system approved by the FDA) until the washing step.

Washing Procedure.

Each unit was washed under aseptic conditions as follows:
1. Each unit was centrifuged at 4658×g for 6 minutes (break rotor was not used) at room temperature. Under these gentle conditions breakage of the cells was avoided.
2. The supernatant was discarded and the platelet pellet was re-constituted in 200 ml sterile docked saline (a way of transferring liquids between containers in a closed system to maintain aseptic conditions).
3. A second centrifugation was carried out in the same conditions specified in step 1.
4. The saline was discarded and the pelleted platelets were re-suspended in 200 ml sterile docked saline.
5. The washed and re-suspended platelets were frozen at −20 to −30° C. The freezing step was carried out within 4 hours from the previous step.

The above elaborated collection and washing procedures of the leukocyte-reduced platelets aphaeresis unit were carried out in a blood collection center (Rock River Valley Blood Center, Rockford, Ill./FDA License #249). The final WAP bags were supplied for the experiments within two months from the date of preparation. The units were received frozen on dry ice.

Example 1: Lyophilized Platelet Extract Prepared from Pooled WAP and Treated with Solvent Detergent (S/D)

Nine WAP bags (each bag containing approximately 200 ml) were thawed by placing the bags at 37° C. water bath for 30 min. In the next step, the WAP bags were wiped with 70% ethanol, cut open, and their content was poured into a stainless steel beaker at room temperature (about 22° C.). The beaker was placed on a stirring device and the pooled WAP material (~1800 ml) was mixed slowly for 5 minutes at room temperature (about 22° C.). During stirring, 200 ml acetate-glycine buffer [200 mM sodium acetate (Sigma-Aldrich, St. Louis, Mo., USA; Cat. Number 32318); and 100 mM glycine (Sigma-Aldrich, St. Louis, Mo., USA; Cat. Number 15527) at pH 6.8-7.4)] and human serum albumin (HSA; at a final concentration of 5% v/v from the total volume) (Plasbumin 25, Talecris Biotherapuetics, NC, USA; Cat. number Plasbumin 25) were added into the pooled WAP. A sample of 500 ml (out of 2000 ml) was removed and treated with solvent and detergent (S/D) to inactivate lipid-enveloped viruses (see procedure below). The rest (1500 ml) was frozen at −80° C. for later analysis ("pooled WAP"). The 500 ml sample was transferred to a chilled (4° C.) stainless steel beaker and placed at 4° C. water bath. The sample was subjected to S/D treatment as follows: 1% Triton X-100 (Sigma-Aldrich, St. Louis, Mo., USA; Cat. number 20180501) and 0.3% tri(n-butyl)phosphate (TnBP; Merck Cat. number 100002) (v/v) were mixed together and then added slowly into the sample while stirring at 60 RPM by using a 3-bladed stainless steel propeller connected to an RW20 overhead stirrer (IKA-Werke GmbH & Co., Staufen, Germany). The sample was then continuously stirred for 4 hours at 4° C. After the S/D treatment, the sample was filtered sequentially through 20, 10 and 5 μm polypropylene capsule filters (DOL Type, MDI Advanced Microdevices Pvt. Ltd., Ambala, India; Cat. number DOLX5111DDXX101, DOLX5108DDXX101, DOLX5107DDXX101, respectively) in order to remove gross particulate debris prior to the S/D removal step.

Removal of the S/D was carried out by using XK26/40 liquid chromatography column (Amersham Pharmacia Biotech, GE Healthcare; Cat. number 18-8768-01) packed with 80 ml of SDR HyperD solvent-detergent removal chromatography resin (Pall Corp, Port Washington, N.Y., USA; Cat. number 20033-015) in conjunction with ÄKTAprime automated liquid chromatography system (GE Healthcare). The column length was 15 cm. The flow rate throughout the run was 10 ml/min. The column was prepared with 320 ml of double distilled water (ddH$_2$O) and equilibrated by 240 ml of acetate-glycine buffer (20 mM sodium acetate, 10 mM glycine at pH 6.8-7.4) and HSA (5% v/v from the total volume). After loading the sample (500 ml), the column was washed with 144 ml of acetate-glycine buffer (as above) containing 5% HSA v/v followed by 144 ml of ddH$_2$O. The total flow through volume collected which included unbound sample and washing buffer was 720 ml. D-mannitol (Sigma-Aldrich, St. Louis, Mo., USA; Cat number M9546) in acetate-glycine buffer (as above) was added into the flow through collected material (at a final concentration of 2% v/v) and served as a cryoprotectant of proteins during the next freeze-drying process. Freezing and thawing of the WAP and subjecting the WAP to S/D treatment and S/D removal resulted in a preparation of platelet extract/lysate.

The flow through collected material was aliquoted into autoclaved glass vials (Fiolax Clear 40×22×1 mm, Schott, Müllheim, Germany) (2 ml in each vial) and lyophilized (Freeze Dryer Epsilon 2-8D, Martin Christ Gefriertrocknungsanlagen GmbH, Osterode am Harz, Germany) according to the cycle elaborated in Table 1 below.

TABLE 1

Lyophilization cycle.

| Step no. | Process phase | Time (h:m) | Temp (° C.) | Vacuum (mBar) |
|---|---|---|---|---|
| 01 | Start Values | 00:00 | 4 | OFF |
| 02 | Freezing | 01:00 | −30 | OFF |
| 03 | Freezing | 01:00 | −50 | OFF |
| 04 | Freezing | 05:40 | −50 | OFF |
| 05 | Preparation | 00:20 | −45 | Off |
| 06 | Sublimation | 00:15 | −40 | 0.200 |
| 07 | Sublimation | 00:15 | −25 | 0.200 |
| 08 | Sublimation | 25:00 | −25 | 0.200 |
| 09 | Sublimation | 01:00 | −15 | 0.200 |
| 10 | Sublimation | 12:00 | −15 | 0.200 |
| 11 | Sublimation | 02:00 | 20 | 0.200 |
| 12 | Sublimation | 05:00 | 20 | 0.200 |
| 13 | Secondary Drying | 00:30 | 25 | 0.012 |
| 14 | Secondary Drying | 18:00 | 25 | 0.012 |

The lyophilized material was sealed with autoclaved rubber stoppers (Silicone 20 mm, West Pharmaceutical Services, Lionville, Pa., USA; Cat. number 7001-2742) under nitrogen atmosphere and in partial vacuum (0.6 Bar). The lyophilized platelet extract prepared from pooled WAP, treated with S/D and SDR HyperD chromatography resin is referred herein as "LYO I".

The purification step in LYO I included a single viral inactivation step of S/D treatment.

Example 2: Protein Profile Characterization of Different Platelet Extract Preparations The following experiment was aimed to characterize the protein profile of washed leukocyte-reduced aphaeresis platelets [WAP material without any treatment (obtained from the US Blood Collection Center mentioned above) as compared to washed platelets from whole blood (obtained from MDA Blood Bank)]; and to examine whether S/D treatment or S/D treatment+SDR HyperD chromatography resin purification affects the protein profile of WAP. S/D treatment and SDR HyperD chromatography resin purification were carried out as elaborated above. In all cases extracts were obtained by freezing and thawing the platelets and, if indicated, by S/D treatment. Protein profile analysis was carried out by sodium dodecyl sulfate polyacrylamide gel electrophoresis (SDS-PAGE). The protein amount of each tested preparation is specified below. The total protein amount was determined using Pierce BCA Protein Assay (Thermo Fisher Scientific Inc., Rockford, Ill., USA; Cat. number 23235) according to the manufacturer instructions. The SDS-PAGE procedure was carried out in the following manner: the preparations were loaded onto a 4-12% tris-glycine gel 1.5 mm×10 wells (Invitrogen, Carlsbad, Calif., USA; Cat. number EC6038BOX) with tris-glycine running buffer (Bio-Rad Laboratories, Hercules, Calif., USA; Cat number 161-0772). The running conditions used were 25 mA constant current for 1.5 hours using PowerPack 300 power supply (Bio-Rad Laboratories, Hercules, Calif., USA). After the running step, the gel was stained overnight at 2-8° C. using InstantBlue Coomassie based staining solution according to the manufacturer instructions (Expedeon Inc., San Diego, Calif., USA; Cat number ISB01L). FIG. 1 shows the protein profile of the different preparations.

The results show that washed leukocyte-reduced aphaeresis platelets (WAP; lane 4) contain very small amounts of albumin relative to washed platelets obtained from whole blood donation (lane 3). The banding patterns of WAP after S/D treatment (lane 5) and after S/D treatment+SDR HyperD chromatography resin purification (lane 6) were similar to that of the starting material (i.e. WAP; lane 4).

These results indicate that the composition of proteins is not significantly affected during the above mentioned processing steps.

Example 3: The Effect of LYO I on Cell Proliferation and on the Morphology of the Cells The following experiment was carried out to examine the biological effect of LYO I (a lyophilized platelet extract prepared from pooled WAP, treated with S/D, subjected to SDR HyperD chromatography resin and lyophilized—prepared as elaborated in Example 1) on fibroblast cell proliferation. The effect of LYO I on cell proliferation was compared to the effect of WAP.

Cell Proliferation Assay.

For this purpose, 3T3-Swiss albino fibroblast cells (ATCC, Cat number CCL92) were plated at a concentration of $25 \times 10^3$ cells/ml (2500 cells/well) in tissue culture treated Costar 96-wells plates (Corning Life Science, MA USA) in 100 µl full growth medium [DMEM (Biological Industries, Israel; Cat. number 01-055-1A) containing 4.5 gr/l glucose and supplemented with 4 mM glutamine (Biological Industries, Israel; Cat. number 03-020-1B), 10% fetal calf serum (FCS; HyClone, USA; Cat. number SH30070.03), penicillin (100 U/ml)/streptomycin (0.1 mg/ml)/amphotericine (0.25 µg/ml) solution (P/S/A; Biological Industries, Israel; Cat. number 03-033-1B)]. The seeded cells were incubated at 37° C. in a humidified atmosphere of 5% $CO_2$. 24 hours after cell seeding, the full growth medium was discarded, the wells were washed twice with 100 µl starvation medium and 100 µl fresh starvation medium was added into each well [starvation medium: DMEM containing 4.5 gr/l glucose supplemented with 4 mM glutamine, 1% MEM-EAGLE non-essential amino acids (Biological Industries, Israel; Cat. number 01-340-1B, 1% human serum albumin (Plasbumin 25, Talecris Biotherapeutics, Germany) and P/S/A (in the concentrations listed above)].

The proliferation was induced 24 hours after replacement of the medium by adding "pooled WAP" (see preparation above) or reconstituted "LYO I". LYO I was reconstituted in 0.4 ml starvation medium (0.4-fold concentrated as compared to the material before lyophilization). Total protein amounts were determined by using Pierce BCA Protein Assay (see Example 2). Concentrations of several growth factors in both WAP I and LYO I were detected by ELISA (Quantikine by R&D Systems, MN USA: Human TGF-131 cat DB100B, Human FGF basic cat HSFB00D, Human PDGF-AB cat DHD00B, Human EGF cat DEG00) and the amounts present in the wells during the proliferation assay are as follows: TGF-β1—205 and 350 ng/ml; bFGF—260 and 265 pg/ml; PDGF-AB—75 and 7 ng/ml; and EGF—3 and 3 ng/ml in wells treated with WAP I and LYO I, respectively.

Proliferation was evaluated 48 hours after addition of addition of WAP or LYO I by using WST-1 Cell Proliferation Reagent according to the manufacturer instructions (Roche Diagnostics, Mannheim, Germany; Cat. number 11-644-807) which quantifies cell proliferation and cell viability based on mitochondria activity. The plate was incubated for 2 hours at 37° C. in a humidified atmosphere of 5% $CO_2$ and then shaken for 1 min. The absorbance of the samples was measured at 450 nm against a background control (starvation medium without cells) as a blank using an ELISA reader. Reference values obtained at 650 nm were subtracted from each value.

Figure 2:
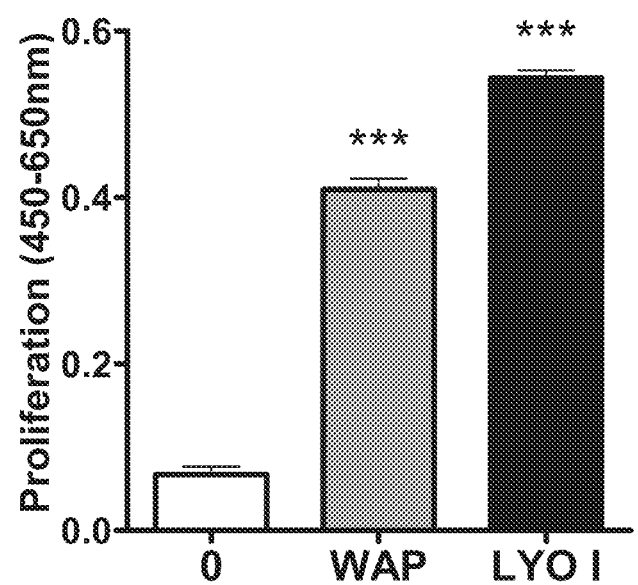
FIG. 2 shows proliferation of 3T3 cells treated with "pooled WAP", "LYO I" or untreated (0). The experiments were carried out in triplicates. Cells grown in starvation medium (marked as "0") were used as the control; ***-p<0.001 (t-test analysis, comparing to "0").

The proliferation rate of 3T3 cells treated with "pooled WAP" or "LYO are shown in FIG. 2. The experiments were carried out in triplicates. Cells grown in starvation medium (marked as "0") were used as the control [***-p<0.001 (t-test analysis, comparing to "0"].

The results show that cell proliferation rate was significantly enhanced by the addition of WAP and LYO I compared to control (marked as 0).

Cell Morphology.

The effect of LYO I on the morphology of cells was monitored with two different cell line types: Human Umbilical Vein Endothelial Cells (HUVEC; Lonza Switzerland; Cat. number C2519A) which are endothelial stem cells from newborn origin; and 3T3-Swiss albino fibroblast cells. Under certain conditions, for example during the wound healing process, fibroblast cells acquire spindle-like shapes. These shapes are an attribute of the increased motility of the fibroblasts (Park et al. Comparative study on motility of the cultured fetal and neonatal dermal fibroblasts in extracellular matrix. Yonsei Med J. 2001 December; 42(6):587-94; Nagano et al. PDGF regulates the actin cytoskeleton through hnRNP-K-mediated activation of the ubiquitin E3-ligase MIR. EMBO J. 2006 May 3; 25(9):1871-82). HUVEC, which are often used to assess induction of angiogenesis by different substances form vessel-like structures (Arnaoutova I, Kleinman H K. In vitro angiogenesis: endothelial cell tube formation on gelled basement membrane extract. Nat. Protoc. 2010; 5(4):628-35). These morphological changes are associated with angiogenesis.

To monitor the effect of LYO I on the morphology of cells, HUVEC or 3T3-Swiss albino cells were seeded at a concentration of $25 \times 10^3$ cells/ml (2500 cells/well) in a 96-wells plate in 100 µl full growth medium [for HUVEC: medium 200 (Gibco Invitrogen, CA USA; Cat. number M200500) supplemented with Low Serum Growth Supplement (LSGS; Gibco Invitrogen, CA USA; Cat. number 500310) and P/S/A solution (in the concentration mentioned above); for 3T3-Swiss albino cells: as listed in the preceding experiment]. 24 hours after cell seeding, the full growth medium was discarded, each well was washed twice with 100 µl starvation medium, and 100 µl fresh starvation medium was added [for HUVEC: medium 200 supplemented with 2% FCS and P/S/A (same concentration as above); for 3T3: as listed in the preceding experiment]. 24 hours after the change to starvation medium, reconstituted LYO I (20 mg/ml total protein in well; reconstitution was carried out in 0.4 ml appropriate starvation medium for each cell) was added into the wells. Concentrations of TGF-β, bFGF, PDGF-AB, and EGF in the wells are the same as in the proliferation assay.

In some HUVEC samples additional treatments were carried out: in some samples addition of 2 IU/ml thrombin (final concentration in the well) (a solution as in the thrombin component of EVICEL™ fibrin sealant, Omrix Biopharmaceuticals Ltd.); in some samples addition of fibrinogen component diluted 1:16 (final dilution in well; the fibrinogen component used was the BAC component of EVICEL™ fibrin sealant); in other samples LYO I+2 IU/ml thrombin (final concentration in the well); and LYO I+diluted fibrinogen component (1:16). All dilutions were carried out in starvation medium. Untreated cells grown in starvation medium were used as control.

The morphology of the cells was microscopically evaluated 48 hours (3T3; FIG. 3) or 72 hours (HUVEC, FIG. 4) after the different treatments. Each experiment was carried out in triplicates.

The results show that untreated 3T3-Swiss albino cells (FIG. 3A) possessed diamond, kite-like shapes (see striped arrows). Addition of LYO I (FIG. 3B) resulted in formation of spindle-like structures (continuous arrows).

HUVEC untreated cells and thrombin treated cells (FIGS. 4A and C, respectively) possessed diamond-like shapes (striped arrows) whereas addition of LYO I (FIG. 4B) induced vessel-like structures formation (continuous arrows). In addition, treatment of HUVEC cells with LYO I and thrombin (FIG. 4D) or LYO I and BAC (FIG. 4F) resulted in an increased vessel-like structures formation as compared to the other treatment groups. Treatment with BAC alone (FIG. 4E) resulted in a minor effect (a few vessel-like structures were formed).

Example 4: Lyophilized Platelet Extract Prepared from Pooled WAP, Treated with S/D, Pasteurized, and Sterile Filtrated Human blood-derived products may carry a risk of transmitting infectious agents such as viruses. Several measures are usually taken in order to minimize the risk of viral and/or unknown pathogens transmission including routine testing donated samples for the presence of certain viruses, and viral inactivation/removal steps during the manufacture process. Effective reduction of viral transmission risk can be achieved by including at least two orthogonal viral inactivation steps that do not alter the beneficial properties of the product. Lipid-enveloped viruses such as HIV, hepatitis B, hepatitis C and West Nile virus are quickly and efficiently inactivated by the S/D treatment which destroys the lipid membrane of the viruses.

Pasteurization is a process by which heat destroys both lipid-enveloped and non-enveloped viruses. Nanofiltration is a process by which lipid-enveloped and non-enveloped viruses are excluded from the sample by using special nanometer-scale filters.

In the following examples the ability of using pasteurization as the second viral inactivation step was assessed.

A pool of WAP material was prepared and S/D treated as elaborated in Example 1 except that: 1) Three WAP bags were used (a total volume of 600 ml). 2) A sample of 430 ml was removed and treated with S/D and the rest 170 ml were frozen at −80° C. for later analysis ("pooled WAP II"). 3) HSA was added into the sample at a final concentration of 1% v/v (and not 5% HSA as in LYO I). 4) The 500 ml [430 ml sample+70 ml acetate-glycine buffer (200 mM sodium acetate; and 100 mM glycine)] sample was transferred to a stainless steel beaker and placed in a water bath set to 25° C. (not 4° C. as in Example 1). 5) Following addition of Triton X-100 and TnBP the sample was continuously stirred for 2 hours at 25° C. (Triton X-100 and TnBP were added for a shorter period of time in this experiment, 2 hours vs. 4 hours in Example 1 since S/D treatment was carried out at a higher temperature 25° C. vs. 4° C. in Example 1). 6) S/D removal was performed using XK26/40 liquid chromatography column packed with 80 ml of SDR HyperD solvent-detergent removal chromatography resin in conjunction with a BT300-2J peristaltic pump (MRC, Israel) and a UA-6 UV/VIS detector+Type 11 recorder (ISCO, NE, USA) at a constant flow rate of 10 ml/min. The column was prepared with 320 ml of ddH$_2$O followed by equilibration with 240 ml of acetate-glycine buffer (20 mM sodium acetate, 10 mM glycine at pH 6.8-7.4) containing 1% HSA v/v (not 5%). 7) After loading the sample (450 ml), the column was washed with 144 ml acetate-glycine buffer (20 mM sodium acetate, 10 mM glycine, pH 6.8-7.4+1% HSA v/v, followed by 144 ml ddH$_2$O. 8) D-mannitol was not added into the flow through material. Next, the flow through S/D treated material (i.e. unbound fraction and washing buffer) (610 ml) was subjected to a step of stabilization and pasteurization as follows: one gram sucrose per gram of flow through sample was slowly added into the flow through material while mixing (at about 22° C.) until the sucrose was completely dissolved. Then, the solution was warmed to 37±1° C. and 0.11 g glycine per g of flow through material was slowly added into the solution while mixing and adjusting the pH to 6.8-7.4 using 0.5N NaOH. pH adjustment was carried out until the glycine was completely dissolved. This was followed by a gradual addition of 0.8 g sucrose per g flow through material while mixing at 37° C. until completely dissolved. Sucrose and glycine were added into the solution to serve as stabilizers during the pasteurization step. The solution was then pasteurized by heat treatment at 60° C. for 10 hours with constant mixing (50 RPM). In order to transfer the resulting viscous solution (which was formed as a result of the stabilizers addition) into a clean vessel, it was diluted with acetate-glycine buffer (20 mM sodium acetate, and 10 mM glycine at pH 6.8-7.4) up to a total volume of 1830 ml. The stabilizers were removed from the solution by diafiltration against acetate-glycine buffer (20 mM sodium acetate, 10 mM glycine, pH 6.8-7.4) using Filtron Ultrafiltration System with 2 Omega Minisette 10 kDa cassettes (Pall Corp, Port Washington, N.Y., USA). The diafiltration step was carried out as follows: the sample was first concentrated to a volume of 900 ml, and dialysis was carried out against a total volume of 5,400 ml acetate-glycine buffer (20 mM sodium acetate, 10 mM glycine, pH 6.8-7.4) by a gradual addition of the buffer and keeping the solution volume at 900±100 ml. The dialyzed solution was then concentrated to 400 ml.

In order to remove aggregated material, the solution was sequentially filtered through 5 and 1.2 µm Sartopure PP2 filters (Cat. Numbers 5591342P5, 5591303P5), followed by 0.45 µm Sartopore 2 filter (Sartorius Stedim Biotech S.A., Aubagne, France; Cat. Number 5441306G5). Sterile filtration was carried out under aseptic conditions (inside a biological sterile cabinet) using a 0.2 µm Sartopore 2 filter (Sartorius Stedim Biotech S.A., Aubagne, France; Cat. Number 5441307H5). The solution was then aliquoted (4 ml) into autoclaved glass vials, lyophilized and sealed with autoclaved rubber stoppers under nitrogen atmosphere and in partial vacuum (0.6 Bar) as indicated in Example 1. The lyophilized platelet extract prepared above is referred herein as "LYO II".

The preparation of LYO II included S/D treatment, a pasteurization step, and final sterile filtration through 0.2 µm.

Example 5: The Effect of LYO II on Cell Proliferation and on Cell Morphology

The following experiment was aimed to determine the effect of LYO II (a lyophilized platelet extract prepared from pooled WAP, treated with S/D, subjected to SDR HyperD chromatography resin, pasteurized, sterile filtrated and lyophilized) on cell proliferation. Cell seeding concentrations and full growth medium replacement were carried out as in Example 3 in two different cell lines: HUVEC and 3T3-Swiss albino (the compatible full growth medium and starvation medium was used for each cell type; see components of medium above; 2500 cells per well in 100 µl medium).

In 3T3-Swiss albino cells, the proliferation was induced 24 hours after replacement of the medium by the addition of pooled WAP II or reconstituted LYO II (the LYO II, which was lyophilized from a 4 ml solution, was reconstituted in 0.5 ml sterile purified water-8-times concentrated as compared to pooled WAP II). Following reconstitution of LYO II, both LYO II and pooled WAP II were serially diluted 5-fold in the compatible starvation medium (the starting concentration of pooled WAP II was designated as 1 accordingly relative concentrations of 1, 0.2, 0.04, 0.008, 0.0016, 0.00032 were used; the starting concentration of LYO II was designated as 8 (this concentration was not tested in this experiment) and accordingly relative concentrations of 1.6, 0.32, 0.064, 0.0128, 0.00256 were used). 10 µl were added from each dilution into the well (initial plating concentration of 2500 cells; and 100 µl medium). Concentrations of several growth factors in both WAP II and LYO II were detected by ELISA (Quantikine by R&D Systems, MN USA: Human PDGF-AB cat DHD00B, Human VEGF cat DVE00) and the actual concentrations that were present in the wells (in the highest concentration) during the proliferation assay are as follows: bFGF—120 and 280 pg/ml; VEGF—0.75 and 2.7 ng/ml; and PDGF-AB—80 and 36 ng/ml in wells treated with WAP II and LYO II, respectively.

Figure 5:
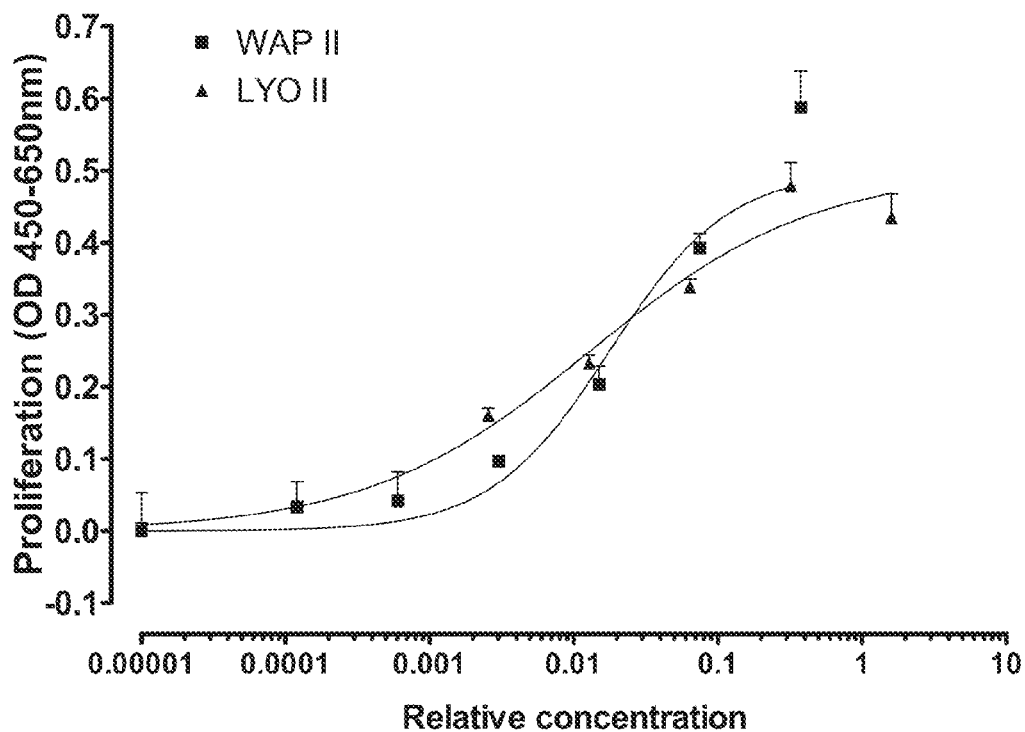
FIG. 5 shows the proliferative effect of LYO II (▲) or pooled WAP II (■) on 3T3-Swiss albino fibroblast cells. The experiment was carried out in triplicates.

The proliferation level of 3T3-Swiss albino cells was evaluated 48 hours later by using the WST-1 Cell Proliferation Reagent. The plate was incubated for 4 hours at 37° C. in a humidified atmosphere of 5% $CO_2$. At the end of the incubation period, the plate was shaken for 1 min and the absorbance of the samples was measured as elaborated in Example 3. The OD values obtained for un-treated cells were subtracted from the obtained OD results and the calculated values were plotted as a sigmoidal dose-response curve. $R^2$ fit and median effective concentration (EC50) values were calculated using GraphPad Prism software. The proliferative effect of LYO II or pooled WAP II on 3T3-Swiss albino fibroblast cells are shown in FIG. 5. The experiment was carried out in triplicates.

The results show that the proliferative effect of LYO II on 3T3-Swiss albino is similar to that of the starting material (pooled WAP II). These results demonstrate that the production process of LYO II, which included double-step viral inactivation, does not affect its potency compared to the WAP starting material e.g. EC50 values were 0.018 and 0.013 for pooled WAP II and LYO II, respectively.

For HUVEC, the proliferation was induced 24 hours after medium replacement by different treatments: addition of thrombin (T; 1 IU/ml final concentration in the well; a thrombin component from EVICEL™ fibrin sealant, Omrix Biopharmaceuticals Ltd.) with or without reconstituted LYO II; and addition of reconstituted LYO II. Untreated cells were used as reference (marked as 0). 10 µl of each solution treatment was added into each well.

Reconstitution of LYO II, which was lyophilized from a 4 ml solution, was carried out in 0.5 ml sterile purified water-8-times concentrated.

Concentrations of bFGF, VEGF, and PDGF-AB were as in the proliferation assay carried out in the 3T3-cells.

Measurements of the proliferation level were carried out 72 hours after the initiation of the treatment by the WST-1 Cell Proliferation Reagent. At the end of the incubation period (4 hours), the plates were shaken for 1 min and the absorbance of the samples was measured as indicated above. The measurements were carried out in duplicates. A third replicate was stained with Calcein-AM in order to explore the angiogenic potency of LYO II (see the results below "Vessel-like structures formation in HUVEC").

Figure 6:
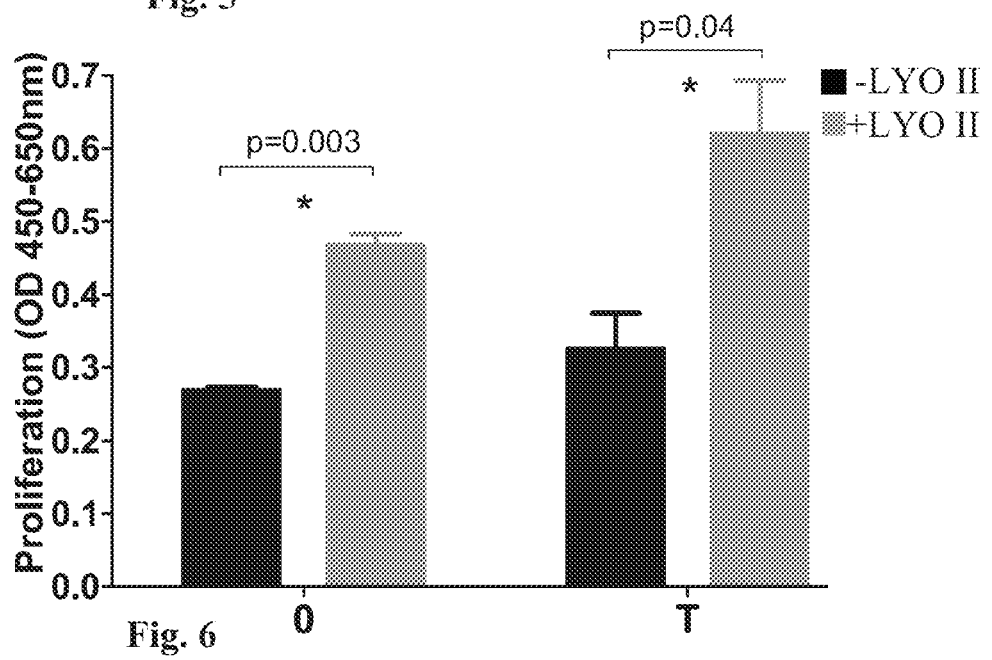
FIG. 6 shows HUVEC proliferation following induction with LYO II, thrombin (T, 1 IU/ml final concentration in the well) and 1 IU/ml thrombin+LYO II. Asterisk denotes significantly different results compared to the related treatment without LYO II as evaluated by t-test analysis (p values are represented).

HUVEC proliferation rate following induction with LYO II, thrombin, and thrombin+LYO II are shown in FIG. 6.

The results show that the addition of LYO II to HUVEC resulted in a significantly higher proliferation as compared to the control cells ("0" without LYO II) or to the cells treated with thrombin alone. Addition of LYO II+thrombin (T) resulted in a more pronounced proliferative activity as compared to the addition of LYO II alone. Vessel-like structure formation in HUVEC.

The following experiment was carried out as a positive control to observe the vessel-like structures acquired by HUVEC when grown on a Basement Membrane Extract (BME) coating in HUVEC starvation medium. BME has an essential role in tissue organization that affects cell adhesion, migration, proliferation, and differentiation and growing of cells (Mehta V B, Besner G E. HB-EGF promotes angiogenesis in endothelial cells via PI3-kinase and MAPK signaling pathways. Growth Factors. 2007 August; 25(4): 253-63; Arnaoutova I, Kleinman H K. 2010). Cells grown on collagen coated wells in HUVEC starvation medium were used as a negative control.

To obtain positive control images, HUVEC cells were plated at a concentration of $1 \times 10^5$ cells/ml (10000 cells/well) in a 96-well plate in 100 µl HUVEC full growth medium (as listed above). The seeded cells were incubated at 37° C. in a humidified atmosphere of 5% $CO_2$. 24 hours later the full growth medium was discarded and 100 µl fresh starvation medium was added into each well (see components of the medium Example 3 above). Prior to cell seeding, the wells were coated with 50 µl/well Basement Membrane Extract reduced growth factors (BME; Cultrex, Trevigen Inc., MD, USA; Cat. Number 3433-005-001) according to the manufacturer's protocol or with 50 µl/well bovine collagen I in a concentration of 3 mg/ml (Invitrogen, CA, USA, Cat. Number A10644-01 prepared according to the manufacturer's protocol for gelling procedures).

After an incubation period of 24 hours, the cells were stained by adding 5 µM for 30 min at 37° C. and a representative picture was taken using Axiovert 200 microscope (at a magnification of ×100) and a fluorescence filter for 530 nm (Carl Zeiss MicroImaging, NY, USA). Calcein-AM is a fluorescent dye which is used in biology for testing cell viability and for short-term labeling of cells—after transport into the cells, intracellular esterases (present in viable cells) remove the acetomethoxy group, the molecule gets trapped inside and gives a strong green fluorescence. As dead cells lack active esterases, only live cells are labeled. The results are presented in FIG. 7.

The results show that pronounced tubular structures which reflect potential of angiogenesis were detected on the BME coated surfaces. No tubulogenesis were observed on collagen coatings (data not shown).

In order to explore the capability of LYO II to induce angiogenesis, the third replicate from the previous experiment (cell proliferation experiment in Example 5) was stained with 5 µM Calcein-AM as above and representative pictures were taken using Axiovert 200 microscope (×200 magnification) and a fluorescence filter for 530 nm. The vessel-like structures acquired by HUVEC following treatment with LYO II are shown in FIG. 8.

It can be seen that addition of reconstituted LYO II (8B) resulted in initiation of formation of tubular structures similar to the positive control treatment (HUVEC seeded on BME coating; FIG. 7).

To explore the ability of LYO II to induce cell morphology changes which might be correlated with induced cell motility, an experiment was carried out in 3T3-Swiss albino cells in similar conditions as in Example 5 cell proliferation assay (compatible full growth and starvation media were used). It was observed that LYO II and pooled WAP II induced morphological changes (form diamond like to spindle-like shapes) as compared to untreated cells (data not shown).

In another experiment, the ability of LYO II to induce vessel-like structures in the presence of fibrin sealant or fibrinogen was evaluated. Fibrin sealant comprises components of the extracellular matrix e.g. fibronectin and fibrinogen (Bar et al. "The binding of fibrin sealant to collagen is influenced by the method of purification and the cross-linked fibrinogen-fibronectin (heteronectin) content of the 'fibrinogen' component". Blood Coagul Fibrinolysis. 2005; 16:111-117). Addition of the fibrin sealant was carried out in order to create environmental conditions which resemble an in-vivo setting. For this purpose, HUVEC were seeded at a concentration of $1 \times 10^5$ cells/ml (10000 cells/well) in tissue pre-coated (with fibrinogen or fibrin—see procedure below) culture treated Costar 96-well plates in 100 µl full medium. 24 hours later the medium was discarded and 100 µl starvation medium was added (the medium comprises the components listed above). Fibrinogen or fibrin pre-coatings were formed as follows:

a. 50 µl fibrinogen component (of EVICEL™ fibrin sealant; Omrix biopharmaceuticals Ltd. diluted to 4 mg/ml with HUVEC starvation medium) was added into each well. The plate was incubated for 1 hour at 37° C., the solution was aspirated and the wells were washed twice with PBS.

b. 50 µl/well fibrin formed from 25 µl fibrinogen component (EVICEL™ fibrin sealant diluted to 8 mg/ml with HUVEC starvation medium), and 25 µl thrombin component (of EVICEL™ fibrin sealant diluted to 2 IU/ml with HUVEC starvation medium).

After the coating solution was applied into the wells, the plate was incubated for 1 hour at 37° C. Then, the solution was aspirated and the wells were washed twice with PBS. Then, the cells were seeded in the conditions listed above (10000 cells/well in 100 µl full growth medium). 24 hours after cell seeding the medium was replaced with 100 µl starvation medium. 24 hours after changing the medium, 10 µl of pooled WAP II or reconstituted LYO II (in 2 ml sterile water i.e. concentrated 2-fold relative to the volume of the WAP starting material) were added into the well. Concentrations of several growth factors in both WAP II and LYO II were as follows: bFGF—480 and 1120 pg/ml; VEGF—3 and 10.8 ng/ml; and PDGF-AB—320 and 144 ng/ml in wells treated with WAP II and LYO II, respectively.

The cells were stained with Calcein-AM as above and representative pictures were taken at 100-fold magnification. The results are presented in FIG. 9.

It is apparent that fibrinogen or fibrin coated surfaces were insufficient to induce pronounced morphological changes that would result in tubulogenesis. However, addition of either LYO II or pooled WAP II together with the fibrinogen or fibrin coatings promoted tubular structure formation.

Example 6: Lyophilized Platelet Extract Prepared from Pooled Washed Aphaeresis Platelets Leukocyte Reduced (WAP) Treated with S/D, Pasteurized, Sterile Filtrated and Concentrated A pool of WAP material S/D and heat treated was prepared as in Example 4 except that: 1) Ten WAP bags were used (a total volume of 2000 ml); 2) A sample of 1720 ml was removed to be treated with S/D and the rest 280 ml was frozen at −80° C. for later analysis ("pooled WAP III"); 3) HSA was added to a final concentration of 1% HSA v/v in the sample; 4) S/D removal was performed using XK50 liquid chromatography column packed with 295 ml of SDR HyperD solvent-detergent removal chromatography resin in conjunction with a peristaltic pump and a UA-6 UV/VIS detector+Type 11 recorder at a constant flow rate of 40 ml/min; 5) The volume of the flow through collected material was 2700 ml; 6) In order to transfer the viscous solution following stabilization and pasteurization, the solution was diluted with acetate-glycine buffer (20 mM sodium acetate; and 100 mM glycine) up to a total volume of 8600 ml; 7) Diafiltration was carried out using Centramate PE tangential flow filtration membrane cassette holder+4 Omega Centramate 10 kDa ultrafiltration cassettes (Pall Corp, Port Washington, N.Y., USA) by first concentrating the sample to a volume of 3500 ml (from a volume of 8600 ml) and then dialyzing against a total volume of 10,320 ml acetate-glycine buffer (as above) by a gradual addition of buffer and keeping the volume at 3500 ml±200 ml. The dialyzed sample was then concentrated to 450 ml—approximately 25% of the staring volume; see point 2 above wherein a sample of 1720 ml was removed to be treated with S/D; 8) the concentrated-dialyzed solution was sequentially filtered through 20, 5 and 1.2 µm Sartopure PP2 filters, followed by 0.45 µm Sartopore 2 filter to remove aggregated material (and not only through 5 and 1.2 µm, followed by 0.45 µm). A sterile filtration was carried out through 0.2 µm. The filtered sample was then aliquoted (4 ml) and lyophilized as described above. The lyophilized platelet extract prepared above is referred herein as "LYO III".

As in LYO II, the viral purification step of LYO III included S/D treatment, an additional pasteurization step, and a final sterile filtration. During the dialysis step the volume of the dialyzed solution was concentrated 4 times as compared to the starting volume.

Example 7: Concentration of Plasma Proteins in Lyophilized Platelet Extract Prepared from Pooled Washed Aphaeresis Platelets Leukocyte Reduced (WAP) Treated with S/D, Pasteurized and Concentrated ("LYO III")

The concentration of various plasma proteins, including proteins involved in blood coagulation, was measured in pooled WAP III and in LYO III.

Reconstitution of LYO III was carried out in ddH$_2$O in the volume prior to lyophilization (4 ml).

The concentration of the different proteins was evaluated as follows:

Thrombin clotting activity was measured by a modification of the European Pharmacopeia Assay (0903/1997) procedure. A calibration curve of log clotting times vs. log thrombin concentration was plotted by mixing thrombin standard (Omrix, Israel) with a fibrinogen solution of 0.1% (Enzyme Research Laboratories, 1N, USA) using STart4 Coagulation Instrument (Diagnostica Stago, Asnières sur Seine, France). Thrombin activity in the different samples was calculated by the clotting time obtained (calculated automatically by a clotting machine, interpolated from the calibration curve and later multiplied by the dilution factor.

Quantitation of active fibrinogen was assessed according to the modified European Pharmacopeia Assay 0903/1997, which is based on the Clauss method. Clotting time was measured using STart4 Coagulation Instrument (Diagnostica Stago, Asnières sur Seine, France). In this method, a calibration curve is prepared with fibrinogen (Enzyme Research Laboratories, Ind., USA) in the presence of excess of thrombin and then the fibrinogen concentration of the samples is calculated from the calibration curve.

Total fibrinogen was measured using a commercial ELISA kit (by MD Biosciences, Zurich, Switzerland; Cat. Number HFIBKT) according to the manufacturer instructions.

Quantification of fibronectin was carried out using a commercial ELISA kit (Technoclone Cat. Number TC12030).

Quantitation of Von Willebrand factor (vWF) was carried out by an ELISA assay. The following antibodies were used for the assay polyclonal rabbit anti human vWF antibody (DAKO; Cat. Number A0082), and polyclonal rabbit anti-human vWF HRP conjugate antibody. A standard curve was prepared using Unicalibrator (Diagnostica Stago; Cat. Number 00625).

Quantities of factors II, VII, VIII, IX, X and XI were determined using STart4 Coagulation Instrument with the following reagents purchased from Diagnostica Stago, Asnières sur Seine, France: STA-Deficient II (Cat. Number 00745), STA-Deficient VII (Cat. Number 00743), STA-Deficient VIII (Cat. Number 0725), STA-Deficient IX (Cat. Number 00724), STA-Deficient X (Cat. Number 00738) and STA-Deficient XI (Cat. Number 00723). All reagents were used according to the manufacturer instructions.

IgG concentration was measured using western blot, a semi-quantitative analysis, with alkaline phosphatase-conjugated AffiniPure Goat Anti-Human IgG (H+L) (Jackson ImmunoResearch Laboratories Inc., PA, USA; Cat. Number 109-055-088). The IgG concentration in the samples was calculated from a calibration curve made with Human IgG BRP Ph. Eur. Reference Standard.

TABLE 2

Concentrations of various plasma proteins in platelet starting material (pooled WAP III) and LYO III.

| Proteins | pooled WAP III | LYO III |
| --- | --- | --- |
| Thrombin (clotting time) IU/ml | <0.25* | <0.25* |
| Fibrinogen (clotting time) mg/ml | <0.08* | <0.08* |
| Fibrinogen (mg/ml) | 0.13 | 0.034 |
| Fibronectin (mg/ml) | 0.001 | 0.004 |
| von Willebrand factor (IU/ml) | <0.0625* | <0.0625* |
| Factor II (IU/ml) | <0.003* | <0.003* |
| Factor VII (IU/ml) | 0.008 | 0.009 |
| Factor VIII (IU/ml) | <0.2* | <0.2* |
| Factor IX (IU/ml) | <0.0038* | <0.0038* |
| Factor X (IU/ml) | 0.003 | 0.003 |
| Factor XI (IU/ml) | 0.0045 | <0.0028* |
| IgG (mg/ml) | 0.011 | 0.076 |

*Value refers to the limit of detection, therefore the sample is considered to be depleted of these proteins.

The results presented in Table 2 show that both pooled WAP III and LYO III comprise very low amounts of plasma proteins. The marginal levels or complete absence of clotting proteins in LYO III renders the platelet extract non-clottable. In comparison, a platelet extract prepared according to Burnouf (WO 2009/087560) contains a high concentration of coagulation factors. LYO III and pooled WAP III comprise less than 0.08 mg/ml active fibrinogen.

Example 8: The Effect of LYO III on Cell Proliferation in Fibroblast Cells and on Morphological Changes in HUVEC The effect of LYO III on cell proliferation was carried out as elaborated in Example 5 using 3T3-Swiss albino cells.

LYO III, which was lyophilized from a 4 ml solution and that was concentrated 4-fold compared to the starting WAP volume, was reconstituted in 0.5 ml of sterile purified water-8-times concentrated (32-fold concentrated compared to starting volume of pooled WAP III). Following reconstitution, pooled WAP III or reconstituted LYO III were serially diluted 5-fold in the appropriate starvation medium and 10 μl of each dilution was added into a well containing 100 μl starvation medium. The starting concentration of pooled WAP III was designated as 1 and the serial dilutions were calculated accordingly. The starting concentration of LYO III was designated as 32 and the serial dilutions were calculated accordingly. Concentrations of several growth factors in both WAP III and LYO III were detected by ELISA (Quantikine by R&D Systems, MN USA: Human TGF-β1 cat DB100B, Human FGF basic cat HSFB00D, Human VEGF cat DVE00, Human PDGF-AB cat DHD00B) and the actual concentrations that were present in the well (in the highest concentration) during the proliferation assay are as follows: TGF-β1—170 and 4250 ng/ml; bFGF—85 and 540 pg/ml; VEGF—1 and 13 ng/ml; and PDGF-AB—73 and 33 ng/ml in wells treated with WAP III and LYO III, respectively.

As a standard control, a custom mixture of recombinant human growth factors (referred herein as MasterMix; MM) was prepared with the following components: TGF-β1 200 ng/ml, b-FGF 0.5 ng/ml, VEGF 5 ng/ml and PDGF-AB 300 ng/ml (the growth factors were purchased from R&D Systems; Cat. Number Cat. Number 240-B-010/CF, 233-FB-025/CF, 293-VE-010/CF and 222-AB-010, respectively). The MM mixture was also serially diluted 5-fold in starvation medium and added into the wells (10 μl). The proliferation was evaluated 72 hours after treatment initiation by using the WST-1 Cell Proliferation Reagent (cells without any additives were used as background and subtracted from OD values). At the end of the incubation period (4 hours), the plates were shaken for 1 min and the absorbance of the samples was measured as indicated above. The tests were carried out in triplicates. In order to compare the different materials based on a common factor, the obtained results were normalized (see below) to the concentration of PDGF-AB, a growth factor which triggers 3T3 cell proliferation, present in all tested materials. Normalizing to PDGF-AB was carried out by measuring the PDGF-AB concentration [a commercial ELISA kit (Quantikine, R&D Systems, MN, USA; Cat. Number DHDOOB] in the reconstituted LYO III and calculating the PDGF-AB concentration in the relative dilutions. The OD results obtained by the WST-1 Cell Proliferation Reagent were plotted against the calculated PDGF-AB concentration values. MasterMix (MM) was used as positive control. Normalization was done to the PDGF-AB concentration as evaluated by specific ELISA.

Figure 10:
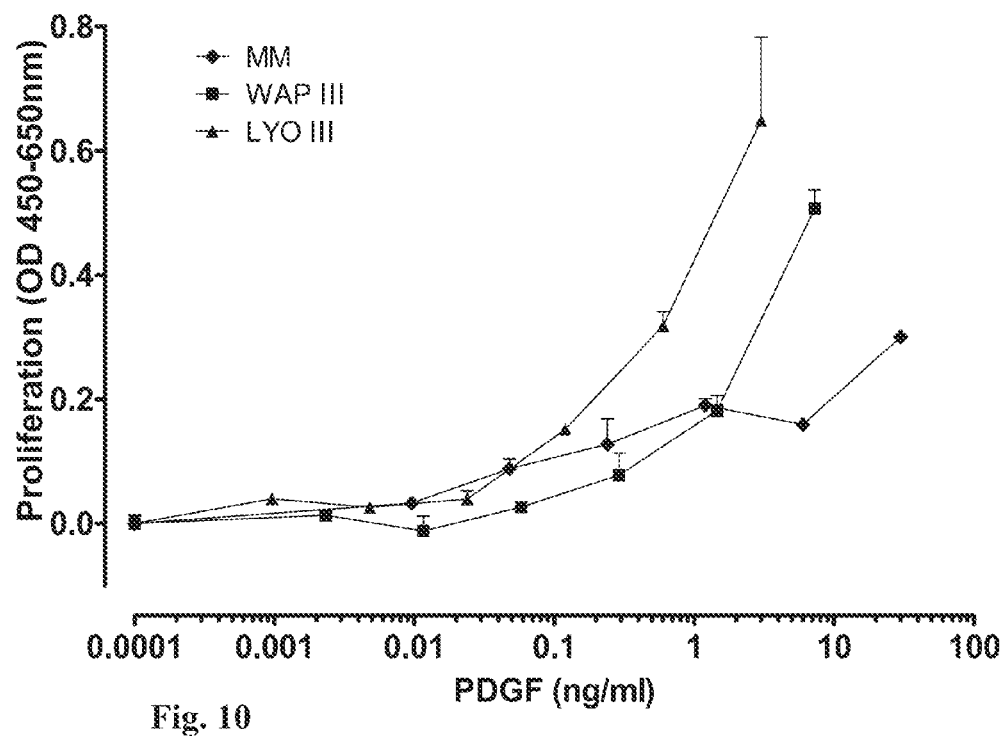
FIG. 10 shows the proliferative effect of LYO III or pooled WAP III on 3T3-Swiss albino fibroblasts. MasterMix (MM) was used as positive control. Normalization was done to the PDGF-AB concentration as evaluated by specific ELISA.

Results of the proliferative effect of LYO III or pooled WAP III on 3T3-Swiss albino cells are shown in FIG. 10.

The results show that increasing concentrations of LYO III or pooled WAP III affected the proliferation level of 3T3-Swiss albino fibroblast cells with the effect of LYO III being more pronounced while normalized to the amount of PDGF-AB present in the samples. Notably, the effect of both treatments was even more pronounced than the positive control (MM).

A tube-formation assay was carried out to assess the angiogenic effect of LYO III and to explore for a possible synergistic effect of LYO III and fibrin sealant or its components. In order to eliminate any possible effects of the additives on attachment of the cells to the plate surface, the cells were first seeded and only then treated with the different additives.

For this purpose, HUVEC were plated at a concentration of $50 \times 10^3$ cells/ml (5000 cells/well) in tissue culture treated Costar 96-wells plates in 100 μl full growth medium (same components as above). 24 h after cell seeding, the full medium was discarded, the wells were washed twice with 100 μl starvation medium, and 100 μl starvation medium was added into each well (same components as above).

24 hours after the medium was changed, the assay was initiated by the addition of 10 μl of either LYO III (reconstituted in 0.5 ml sterile water—concentrated 32-fold relatively to pooled WAP III volume) or a combination of LYO III and fibrin [formed with 1 IU/ml thrombin (final concentration in well) and 11.3 mg/ml (total protein) fibrinogen [both thrombin and fibrinogen are components of EVICEL™ fibrin sealant (Omrix Biopharmaceuticals Ltd.) diluted in starvation medium]. Concentrations of TGF-β, bFGF, VEGF, and PDGF-AB in the wells were as in the proliferation above.

Cells treated with thrombin and/or fibrinogen in the same concentrations listed above were used as reference. 48 hours after the different treatments, the cells were stained with 5 uM Calcein-AM for 30 min at 37° C. and representative pictures were taken using Axiovert 200 microscope at 100-fold magnification and fluorescence filter for 530 nm (Zeiss). The results are presented in FIG. 11.

Figures 11A, 11B, 11C:
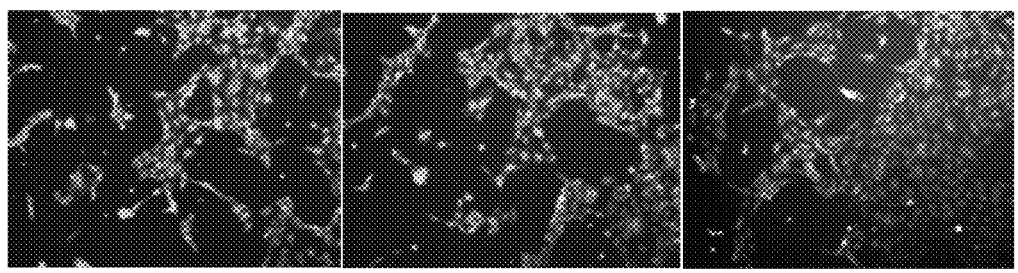
FIG. 11 shows morphological appearance of HUVEC treated with thrombin (B; 1 IU/ml final concentration), fibrinogen (C, 11.3 mg/ml total protein), LYO III (D), fibrin (thrombin and fibrinogen) (E), and fibrin and LYO III (F). A-Control cells without treatment. The pictures were taken at 100-fold magnification using fluorescence filter for 530 nm.
Figures 11D, 11E, 11F:
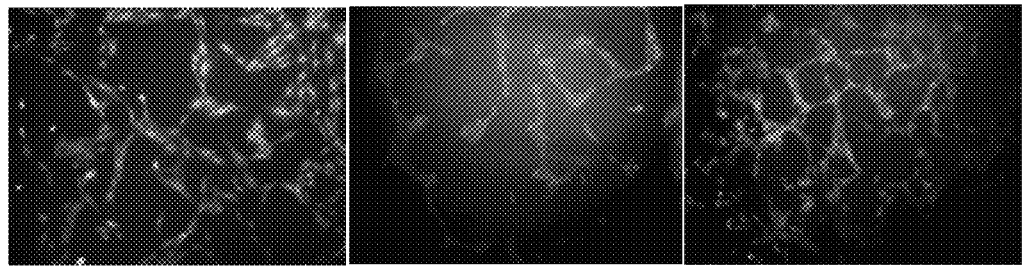

As depicted in the FIG. 11, no tubulogenesis were observed in the control cells (A). Also, it is apparent that thrombin or fibrinogen alone had only marginal ability to induce morphological changes in HUVEC as can be evaluated from the very low number of prolonged cells and vessel-like shapes (B and C, respectively). Treatment with fibrin (thrombin and fibrinogen; E) resulted in re-arrangement of the cells toward tubulogenesis however no pronounced vessel structures were detected. Addition of LYO III (D) to the HUVEC monolayer promoted tubulogenesis which was further augmented by addition of fibrin (F).

Example 9: Lyophilized Platelet Extract Prepared from Pooled Washed Aphaeresis Platelets Leukocyte Reduced (WAP), Treated with S/D Under Low Aggregate Conditions, Pasteurized and Concentrated In this experiment a lyophilized platelet extract was prepared from a frozen material, before thawing as follows: Ten WAP bags were individually weighed, wiped with 70% ethanol, cut open and the frozen material was placed in a large beaker that was immersed in a water bath adjusted to 25° C. The empty bag was weighed and the weight difference between the empty bags and the full bags was used to calculate the net WAP weight (the net WAP weight of each bag was about 200 g). The pooled material was mixed slowly at 25° C. until completely thawed using a stainless steel propeller connected to an RW20 overhead stirrer (IKA-Werke GmbH & Co., Staufen, Germany) at 20 RPM. The osmolarity of the pooled WAP was 275 mOs [measured by using The Advanced™ Micro Osmometer Model 3300 (Advanced Instruments Inc, Norwood, Mass., USA)]. 10% acetate-glycine buffer (200 mM sodium acetate, 100 mM glycine; at pH 6.8-7.4) and 1% HSA (v/v from the final volume solution) were added into the pooled WAP. In order to keep the osmolarity level as constant as possible throughout the process, buffer osmolarity was adjusted to that of the WAP starting material using NaCl (Sigma-Aldrich, St. Louis, Mo., USA). In the next step, S/D treatment was carried out by slowly adding 1% Triton X-100 and 0.3% TnBP (v/v) into the pooled sample while mixing at 50 RPM. In order to avoid sub-optimal viral inactivation due to the possible presence of particulate matter, the S/D treatment was split into two parts. First, the sample was continuously stirred for 30 minutes and then filtered through 20, 5 and 1.2 μm Sartopure PP2 filters and 0.45 μm Sartopore 2 (Sartorius Stedim Biotech S.A., Aubagne, France). Then, the filtered material was returned to a beaker immersed in a water bath adjusted to 25° C. and mixed at 50 RPM for additional 2 hours for continuing the viral inactivation process. S/D removal was carried out using XK50 liquid chromatography column packed with 295 ml SDR HyperD solvent-detergent removal chromatography resin (Pall Corp) in conjunction with a peristaltic pump and a UA-6 UV/VIS detector+Type 11 recorder (ISCO, NE, USA). 1800 ml of S/D-treated platelet extract were loaded onto the column followed by washing with 540 ml acetate glycine buffer (200 mM sodium acetate, 100 mM glycine; at pH 6.8-7.4)+1% HSA v/v. A total volume of 2700 ml was collected from the column (flow through). It was found that water-insoluble aggregates, which may interfere with later stages of the production, are formed during the manufacturing process. It was also found that the aggregation is intensified in the presence of calcium. Thus, it was decided to use calcium to facilitate the precipitation of aggregates at an early stage, followed by removal of these aggregates by clarification filtration. Accordingly, $CaCl_2$ was slowly added (to 40 mM final concentration) to the extract following S/D removal procedure and the extract was incubated for 30 minutes at 25° C. while mixing at 50 RPM. The product was then filtered using 20, 5 and 1.2 μm Sartopure PP2 filters and 0.45 μm Sartopore 2 (Sartorius Stedim Biotech S.A., Aubagne, France). In the next step, the extract was subjected to stabilization and pasteurization as in Example 4. In order to transfer the obtained viscous solution into a clean vessel, it was diluted with acetate-glycine buffer (at a final concentration of 20 mM sodium acetate, 10 mM glycine in the viscous solution; at pH 6.8-7.4) and 1% HSA v/v up to a total weight of 11,320 ml. Removal of the stabilizers was carried out by diafiltration against acetate-glycine buffer (as above) using Centramate PE tangential flow filtration membrane cassette holder+4 Omega Centramate 10 kDa ultrafiltration cassettes (Pall). The diafiltration was carried out as follows: the extract was first concentrated to a volume of 3600 ml and then dialysis was carried out against a total volume of 10,800 ml acetate-glycine buffer (as above) by a gradual addition of the buffer and keeping the solution volume at 3600±200 ml. The dialyzed solution was then concentrated to a volume of 473 ml, which is approximately 25% of the starting volume.

For stabilization, Mannitol was added into the solution at a final concentration of 2% w/w. In order to remove aggregated material, the sample was sequentially filtered through 20, 5 and 1.2 μm Sartopure PP2 filters, and 0.45 μm Sartopore 2 filter. Sterile filtration was carried out under aseptic conditions using a 0.2 μm Sartopore 2 filter. The product was then aliquot into 4 ml portions under aseptic conditions and lyophilized as elaborated above. The lyophilized material was sealed in nitrogen atmosphere in partial vacuum (0.6 Bar). The lyophilized platelet extract prepared above is referred herein as "LYO IV".

The viral purification step of LYO IV included S/D treatment which included a filtration sub step within the SD treatment. Filtration at this step was carried out through 20, 5, 1.2 and 0.45 μm filters. In addition, a pasteurization step was carried out, and a final sterile filtration. During the dialysis step the volume of the dialyzed solution was concentrated 4 times as compared to the starting volume.

Example 10: The Effect of LYO IV on Cell Proliferation and Morphological Changes in Fibroblast Cells and on Morphological Changes in HUVEC The effect of LYO IV on cell proliferation was carried out as elaborated in Example 5. 3T3-Swiss albino cells were plated at a concentration of $25\times10^3$ cells/ml (2500 cells/well) in tissue culture treated Costar 96-wells plates in full growth medium (components as elaborated above). 24 h after cell seeding, the full growth medium was replaced with fresh starvation medium (as above). The proliferation was induced 24 hours after the medium was replaced by the addition of pooled WAP IV or reconstituted LYO IV. Reconstitution was carried out as follows: LYO IV, which was lyophilized from a 4 ml solution (concentrated 4-fold comparing to starting pooled WAP), was reconstituted in 0.5 ml sterile purified water-8-times concentrated (32-fold concentrated compared to the starting volume pooled WAP IV). Following reconstitution, reconstituted LYO IV or pooled WAP IV were serially diluted 5-fold in the appropriate starvation medium and 10 μl of each dilution was added into a well containing 100 μl starvation medium. The starting concentration of pooled WAP IV was designated as 1 and the serial dilutions were calculated accordingly (relative concentration). The starting concentration of LYO IV was designated as 32 and the serial dilutions were calculated accordingly. Concentrations of several growth factors in both WAP IV and LYO IV were detected by ELISA (same kits as above) and the actual concentrations present in the well (in the highest concentration) during the proliferation assay are as follows: TGF-β—230 and 2000 ng/ml; bFGF—100 and 170 pg/ml; VEGF—1.25 and 8.1 ng/ml; PDGF-AB—57 and 27 ng/ml; and Thrombospondin-1—60 and 330 ng/ml in wells treated with WAP IV and LYO IV, respectively.

MasterMix (MM) prepared as in Example 8 was used as positive control. This mixture was serially diluted 5-fold in starvation medium and 10 μl was added into the wells. The maximal concentration of MM was designated as 30 (since the concentration of PDGF-AB in MM was 30 ng/ml) and the serial dilutions were calculated accordingly.

Figure 12:
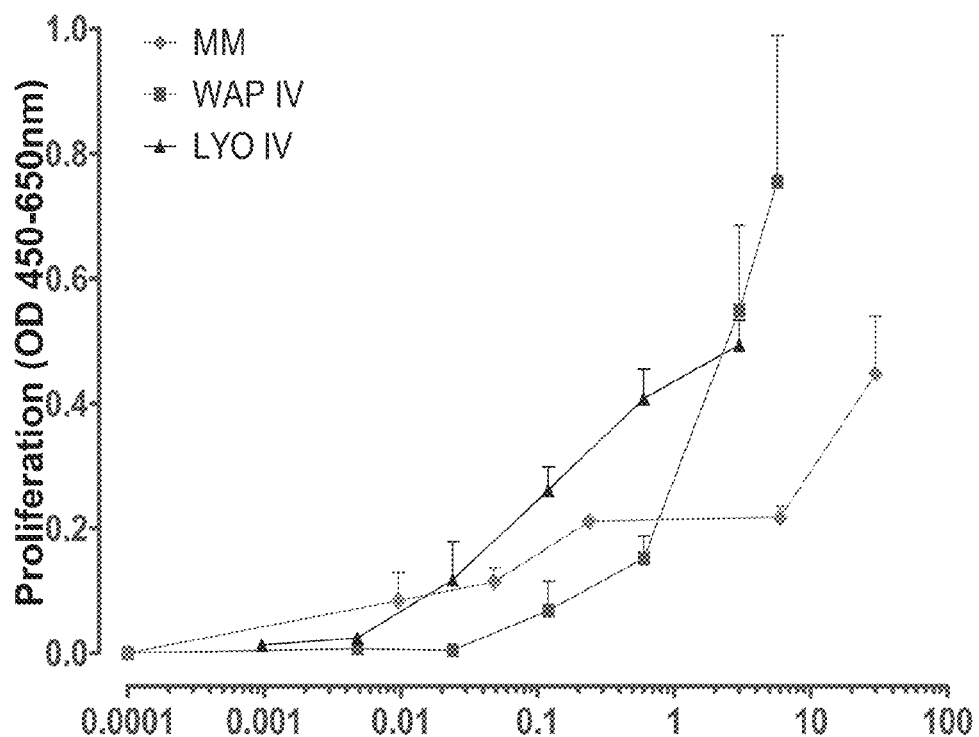
FIG. 12 shows proliferation level of 3T3-Swiss albino fibroblast cells following different treatments. MasterMix (MM; ♦) was used as reference. Normalization was done to the PDGF-AB concentration as evaluated by specific ELISA. All the tests were done in triplicates.

The proliferation of the cells was evaluated 48 hours after beginning of the treatment as elaborated above. After 4 hours incubation with WST-1, the absorbance of the samples was measured as indicated above. The obtained results were normalized to the PDGF-AB (as explained above). All the tests were done in triplicates. The results are presents in FIG. 12.

The results show that LYO IV and pooled WAP IV had a similar effect on 3T3-Swiss albino fibroblasts proliferation level. The obtained effect was even more pronounced than the positive control (MM).

To evaluate the effect of LYO IV on morphological changes of 3T3-Swiss albino cells, phase-contrast microscope images were taken following the treatments (the cells were seeded as in the proliferation assay in Example 10, treated with 10 μl of reconstituted LYO IV (in 0.5 ml sterile water), pooled WAP IV and maximal concentration of MM (as in Example 8) added to 100 μl of starvation medium and the images were taken 2 days following the treatment). Concentrations of TGF-β, bFGF, VEGF, PDGF-AB, and Thrombospondin-1 in the wells were as in the proliferation assay. Representative images are shown in FIG. 13.

Figure 13A:
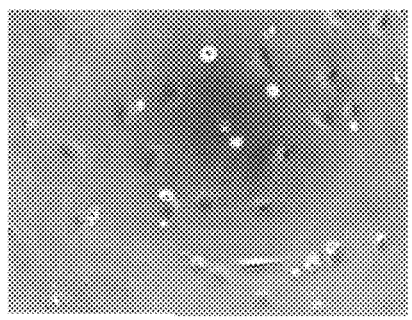
FIG. 13 shows 3T3-Swiss albino morphological appearance following induction by LYO IV (B), pooled WAP IV (C), and MasterMix (MM; D). (A) Untreated cells. The pictures were taken at 200-fold magnification using phase-contrast microscope.
Figure 13B:
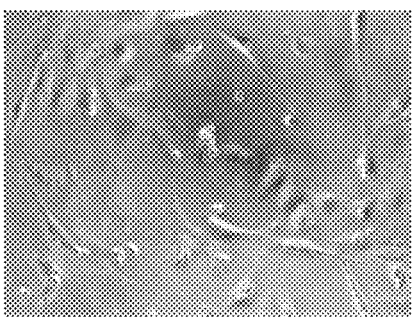
Figure 13C:
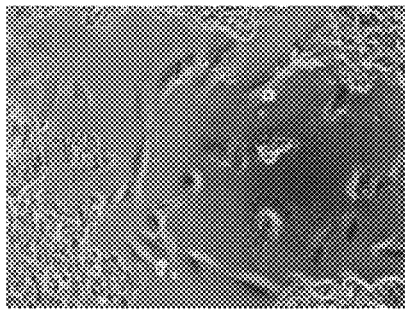
Figure 13D:
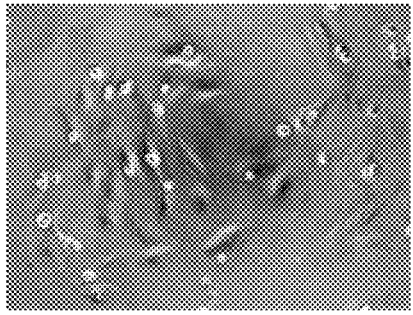
Figure 14A:
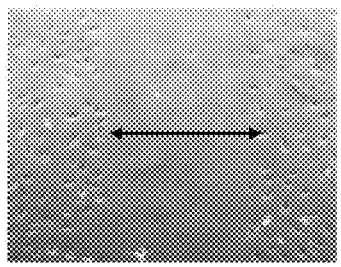
FIG. 14A-O show representative phase-contrast images (×100 magnification) of the in-vitro wound scratch assay performed with 3T3-Swiss albino fibroblasts. The cells were plated on different surfaces—uncoated (A,D,G,J,M), collagen (B,E,H,K,N)—or fibrinogen (C,F,I,L,O)-coated wells and wounded with a p200 pipette tip. The wounds were captured at time point "0" (A,B,C) and 24 hours (D-O) after treatment with LYO IV (G,H,I), pooled WAP IV (J,K,L), or PRP-R (M,N,O).
Figure 14B:
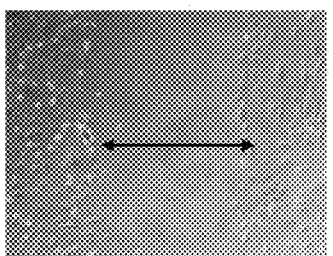
Figure 14C:
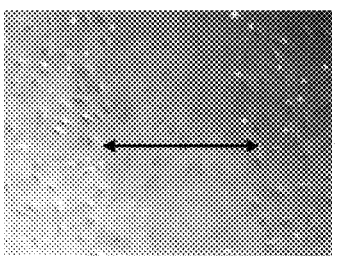
Figure 14D:
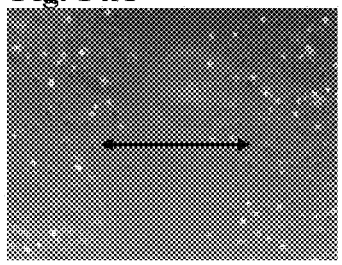
Figure 14E:
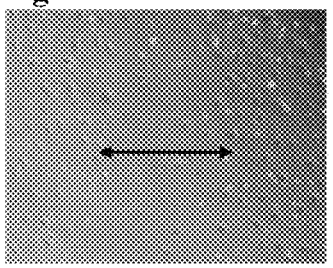
Figure 14F:
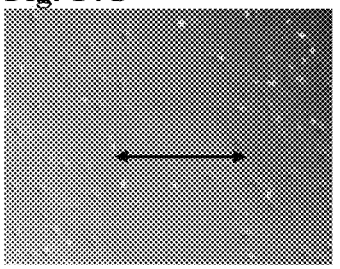
Figure 14G:
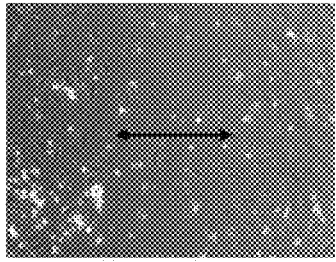
Figure 14H:
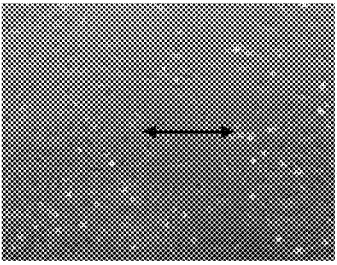
Figure 14I:
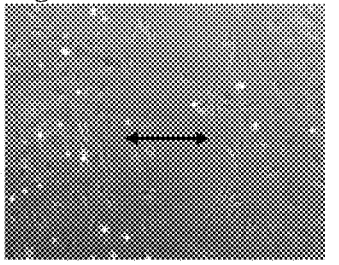
Figure 14J:
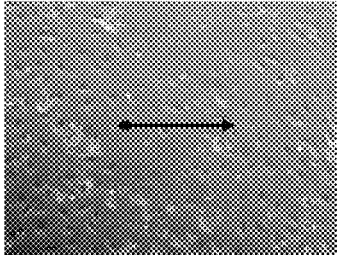
Figure 14K:
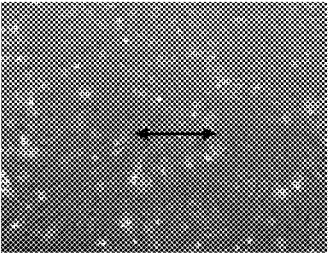
Figure 14L:
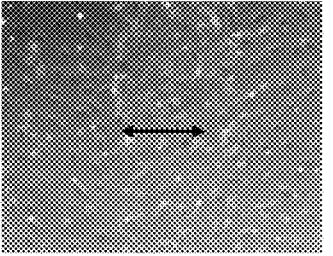
Figure 14M:
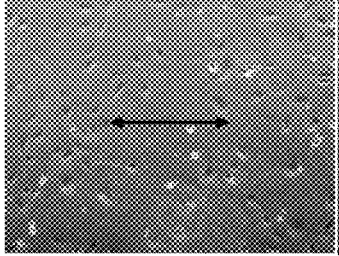
Figure 14N:
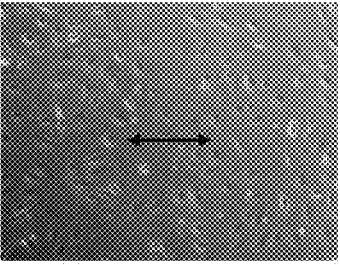
Figure 14O:
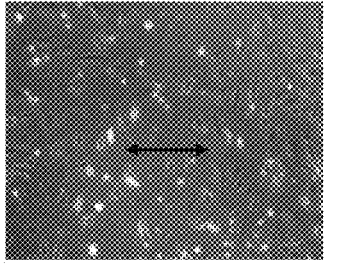

Untreated fibroblast cells possess diamond-like shapes (FIG. 13A). Addition of LYO IV (B) to 3T3-Swiss albino fibroblasts promoted morphological changes of the cells from diamond-like cells to spindle-like shapes, a characteristic of motile fibroblasts. These observed morphological changes were stronger than the changes observed following treatment with pooled WAP IV (C) and the positive control (MM; D).

As indicated above, the spindle-like shapes of 3T3 fibroblast cells are an attribute of the motility potential. In the following experiment the actual motility of the cells was evaluated following treatment with LYO IV by using the wound-scratch migration assay (Liang et al. In vitro scratch assay: a convenient and inexpensive method for analysis of cell migration in vitro. Nat. Protoc. 2007; 2(2):329-33). 3T3-Swiss albino cells were plated at a concentration of $1 \times 10^5$ cells/ml (50,000 cells/well) in tissue culture treated Costar 24-wells plates (Corning Life Science, MA USA) in 0.5 ml full growth medium (as above). Prior to seeding, the well was coated with one of the following:

1. Collagen coating—12.5 µg/cm² from a collagen solution (Collagen I, Bovine, 5 mg/ml, Invitrogen, CA, USA, Cat. Number A10644-01, prepared according to the manufacturer's protocol for thin coating procedures a dilution of 50 µg/ml in 10 mM Acetic Acid was used). The coating was applied according to the manufacturer's protocol.
2. Fibrinogen coating—250 µg/cm² from the fibrinogen component of EVICEL™ fibrin sealant (Omrix Biopharmaceuticals Ltd.) diluted with DMEM medium to 1 mg/ml fibrinogen. After 1 hour incubation at room temperature, the solution was aspirated and the wells were washed with fresh DMEM.

Uncoated wells were used as control. 6 hours after cell seeding, the full growth medium was discarded, the wells were washed twice with 0.5 ml starvation medium and 0.5 ml fresh starvation medium was added into each well (as above). After over-night starvation the cell monolayer was wounded in the middle of the well with a p200 plastic pipette tip, the detached cells were washed out together with the starvation medium and 0.5 ml fresh starvation medium was added. Migration of the cells (i.e. motility) was evaluated following addition of either pooled WAP IV, reconstituted LYO IV (in 2 ml of sterile water), or PRP-R (PRP-releasate) [prepared as follows: 60 ml of single-donor PRP (prepared by and obtained from MDA, Blood Bank, Israel) were activated with 3 ml of 1000 IU/ml Thrombin (from EVICEL™) and 2 ml of 2M CaCl$_2$, and then centrifuged at 3000 g for 10 min at 4° C. resulting in 27 ml supernatant which was used for the experiment]. All treatment solutions were diluted 1:10 into the well (50 µl). Each treatment was carried out in duplicates.

Concentrations of several growth factors in both WAP IV and LYO IV were as follows: TGF-β—920 and 8000 ng/ml; bFGF—400 and 680 pg/ml; VEGF—5 and 32.4 ng/ml; PDGF-AB—228 and 108 ng/ml; and Thrombospondin-1—240 and 1320 ng/ml in the wells (respectively for WAP IV and LYO IV).

The wounded width was captured using phase-contrast microscope (×100 magnification) at three different locations in each well (6 pictures per each treatment) at time point 0 and after 24 hours. In each picture, the wounded width was measured 5 times (15 times per well) and the wound closure (a narrower wound width) was calculated as a percentage of wound left 24 hours after initiation of the treatment in the same location.

Figure 15:
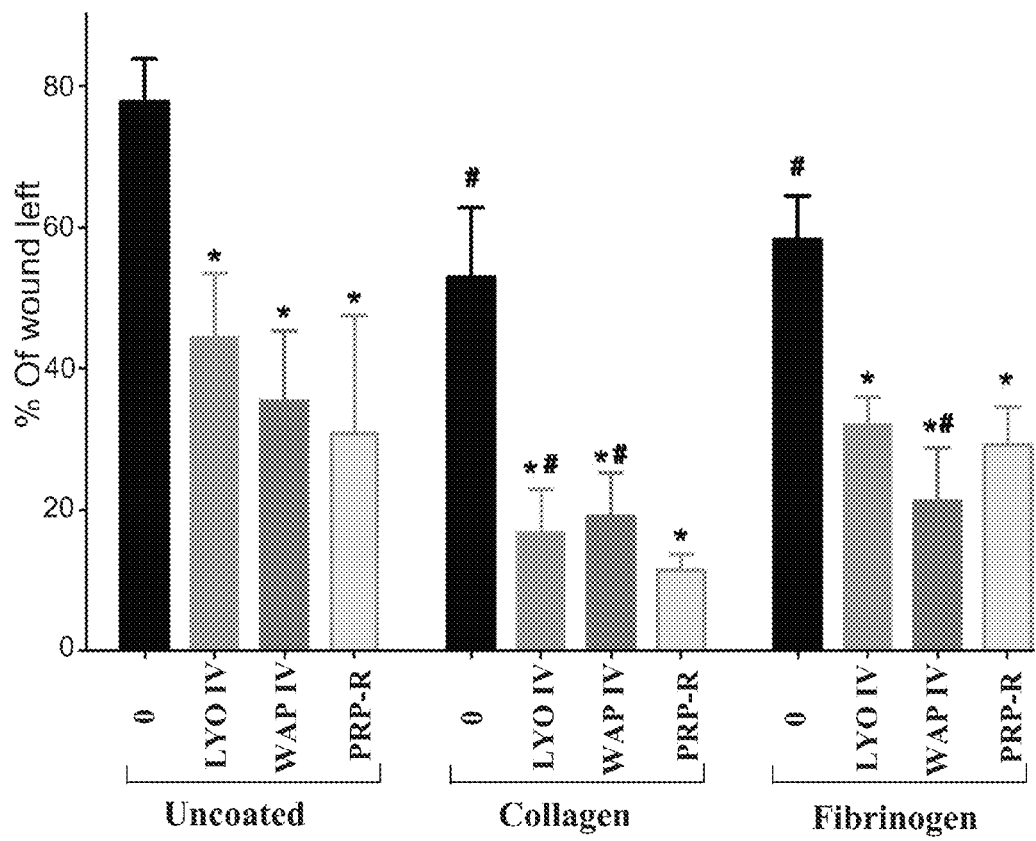
FIG. 15 shows a quantitative evaluation of the wound closure as a percentage left 24 hours after initiation of the treatment in the different treatment groups. The cells were plated on different surfaces (uncoated, collagen or fibrinogen coated wells) and treated with LYO IV, pooled WAP IV, or PRP-R after scratching the monolayer with a p200 pipette tip. The % of wound left was calculated as a ratio of the distance left after 24 h to the starting distance in each location. Results are presented as mean of 6 replicates ±S.D. T-test analysis was performed, statistical significance was determined as p<0.05. *compared with wells without treatment (0) per each surface); # compared to the related treatment on the uncoated surfaces.

Representative phase-contrast pictures of the wounded width in the different treatments at the different time points are shown in FIG. 14. Quantitative evaluation of the wound closure as a percentage left 24 hours after initiation of the treatment in the different treatment groups are shown in FIG. 15. Results are presented as mean of 6 replicates ±S.D.

The results show that on all surfaces (coated or uncoated wells) LYO IV promoted fibroblasts motility and closure of the scratch in the monolayer (the wound is narrower than the control reference treatment) in a similar manner as pooled WAP IV and PRP-R (which has been reported as efficient in wound healing in in-vivo settings Lacci K M, Dardik A, 2010).

Collagen coated wells showed a slightly higher motility promoting effect as compared to the fibrinogen coated wells.

Tube-formation assay was carried out to assess the ability of LYO IV to induce morphological changes of HUVEC. These morphological changes are associated with angiogenesis. For this purpose, HUVEC were plated at a concentration of $1 \times 10^5$ cells/ml (10000 cells/well) in tissue culture treated Costar 96-wells plates in 100 µl starvation medium (as above, excluding 2% FCS). In order to simulate extracellular matrix environment, the wells were coated with BME (50 µl/well according the manufacturer protocol) prior to cell seeding.

During seeding, 10 µl of either pooled WAP IV or LYO IV (reconstituted in 2 ml sterile water, concentrated 8-fold relatively to pooled WAP IV volume) were added to the designated wells. The concentration of TGF-β, bFGF, VEGF, PDGF-AB, and Thrombospondin-1 in the wells were as in the migration assay above. Untreated HUVEC seeded on BME coating were used as reference. After 24 h the cells were stained with 5 uM Calcein-AM for 30 min at 37° C. and representative pictures were taken using Axiovert 200 microscope with 60-fold magnification and fluorescence filter for 530 nm (Zeiss). The results are shown in FIG. 16.

Figures 16A, 16B:
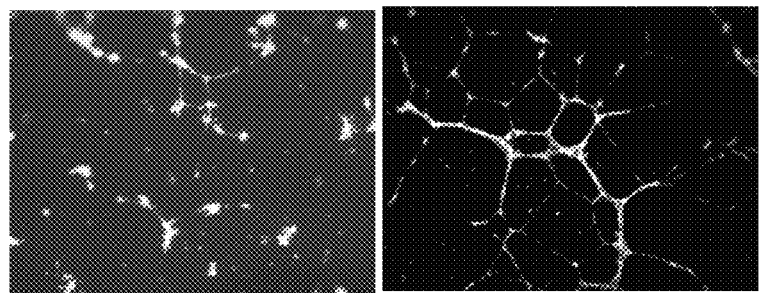
FIG. 16 shows the morphological appearance of HUVEC seeded on BME coated wells and treated with LYO IV (B) or pooled WAP IV (C). (A) Untreated HUVEC seeded on BME coating. The pictures were taken at 60-fold magnification using fluorescence filter for 530 nm.
Figure 16C:
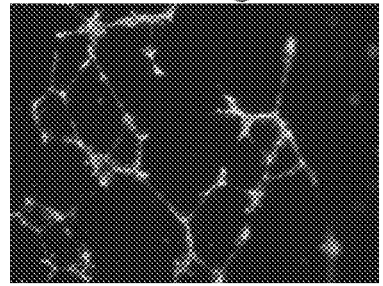

As observed in FIG. 16, LYO IV (B) had the strongest tubologenic potency compared to WAP IV (C) or untreated cells (A) (treatment with LYO IV resulted in vessel-like structure formation).

Example 11: Evaluating the Use of Nanofiltration as a Second Viral Inactivation Step A pool of WAP material was prepared from 10 donors (2000 ml) as elaborated in Example 1. Then, 200 ml acetate-glycine buffer and 1% HSA v/v were added into the pooled WAP. A sample of 50 ml was removed, treated with S/D as elaborated below and stored in −80° C. until assayed. Upon analysis the sample was thawed at room temperature and then filtered (to remove any particulate matter) through 0.45 µm syringe filter (Millex-HV by Millipore; Cat. Number SLHV033RS). Only about 25 ml (out of 50 ml) were filtered before the filter was clogged, therefore a fresh filter was used for the remainder of the sample. Extracts were obtained by freezing and thawing and by carrying out an S/D treatment.

After thawing, an S/D removal step was carried out using HR 10×10 liquid chromatography column (Amersham Pharmacia Biotech) packed with 8 ml of SDR HyperD solvent-detergent removal chromatography resin (Pall Corp.) in conjunction with a peristaltic pump and a UA-6 UV/VIS detector+Type 11 recorder (ISCO, NE, USA). The flow parameters used during the process were: 1 ml/min with a maximum pressure limit of 1.0 bar.

The column was prepared with 32 ml of purified water, followed by 24 ml of acetate glycine buffer including 1% HSA v/v. The column was loaded with 40 ml of the extract sample. After loading the extract sample, the column was washed first with 14 ml of acetate-glycine buffer including 1% HSA v/v. A second washing step was carried out using 22 ml of acetate-glycine buffer including 10% ethanol/1M NaCl/0.2% HSA. The latter washing step was found in our experiments to increase the recovery of some growth factors, e.g. PDGF-AB and PDGF-BB (See Example 12). The column was then washed with 16 ml purified water. The total volume of the collected flow through was 80 ml. To facilitate the precipitation of aggregates at an early stage, precipitation with $CaCl_2$ was carried out as described in Example 9. Clarification filtration of the extract sample after the $CaCl_2$ treatment was carried out using 5 µm capsule filter (mdi Advanced Microdevices), followed by 0.45 µm syringe filter (Millex-HV by Millipore; Cat. Number SLHV033RS).

To remove smaller aggregates, a pre-filtration step was carried out prior to the nanofiltration step by passing the material through 0.2 and 0.1 µm filters. In order to filter the entire 80 ml of extract sample, two 0.2 µm vacuum filters (Nalgene Supor Mach V 50 mm) and four 0.1 µm syringe filters (Millex VV by Millipore; Cat. Number SLVV033RS) were used. The filtered material was then subjected to a nanofiltration step. The nanofiltration system was assembled in-line as follows: Pressured nitrogen gas tank—pressure regulator—filter housing SEALKLEEN (Pall Corp.) with 2.5 bar pressure gauge (PG1)—valve—0.2 µm filter (Minisart by Sartorius; Cat. Number 16534)—0.1 µm filter (Millipore; Cat. Number VVLP02500)—1.0 bar pressure gauge (PG2)—PLANOVA 75N filter (Asahi Kasei; Cat. Number 75NZ-001)—1.0 bar pressure gauge (PG3)—PLANOVA 35N filter (Asahi Kasei; Cat. Number 35NZ-001)—1.0 bar pressure gauge (PG4)—PLANOVA 20N filter (Asahi Kasei; Cat. Number 20NZ-001).

The nanofiltration procedure was carried out as follows:

Prior to loading the extract sample, the performance of the system was tested by filling the filter housing with 40 ml purified water (PuW), and elevating the pressure by increasing the nitrogen gas flow into the system. Under normal conditions, the solution is expected to flow through the system with only small drops in pressure after passing through each PLANOVA filter. As shown in Table 3 below, 40 ml of PuW were passed through the system without a major drop in the pressure.

After verifying the performance of the system, the filter housing was filled with acetate glycine buffer (20 mM sodium acetate, 10 mM glycine; at pH 6.8-7.4) containing 1% HSA (the same buffer that is present in the extract sample). The results in the Table below show that the pressure level and the flow rates enabled the buffer to pass through the entire system. However, when the extract sample was loaded, it failed to pass throughout the system. As shown in the Table below, the pressure reading before the PLANOVA 75N (PG2) was 0.9 bar, whereas the pressure after the PLANOVA 75N and before to the PLANOVA 35N filter (PG3) was only 0.2 bar, indicating that the sample could not easily pass through the PLANOVA 75N filter.

TABLE 3

Pressure level and flow rates obtained when subjecting DDW, buffer and the platelet extract to nanofiltration.

|  | Passed volume (ml) | PG1 (bar) | PG2 (bar) | PG3 (bar) | PG4 (bar) | Time (min) | Flow (ml/min) |
|---|---|---|---|---|---|---|---|
| DDW | 40 | 1.0 | 1.0 | 0.9 | 0.8 | N/A | N/A |
| Buffer | 0-5 | 1.0 | 1.0 | 0.65 | 0.45 | 12 | 0.4 |
|  | 5-10 | 0.9 | 1.0 | 0.7 | 0.4 | 18 | 0.27 |

TABLE 3-continued

Pressure level and flow rates obtained when subjecting DDW, buffer and the platelet extract to nanofiltration.

|  | Passed volume (ml) | PG1 (bar) | PG2 (bar) | PG3 (bar) | PG4 (bar) | Time (min) | Flow (ml/min) |
|---|---|---|---|---|---|---|---|
|  | 10-15 | 0.8 | 0.9 | 0.7 | 0.4 | 21 | 0.24 |
|  | 15-20 | 1.0 | 1.0 | 0.75 | 0.42 | 24 | 0.21 |
| Extract sample |  | 0.9 | 0.9 | 0.2 | 0.0 | 0.0 | 0.0 |

These results show that it is not feasible to utilize nanofiltration as a second viral inactivation step using the conditions elaborated above.

Example 12: Lyophilized Platelet Extract Prepared from Pooled Washed Aphaeresis Platelets Leukocyte Reduced (WAP), Treated with S/D, S/D Removed Using SDR HyperD Chromatography Using Elution Conditions, Pasteurized and Concentrated In this experiment a lyophilized platelet extract was prepared as follows: Ten WAP bags were individually weighed wiped with 70% ethanol, cut open and the frozen material was placed in a large beaker that was immersed in a water bath adjusted to 25° C. The empty bag was weighed and the weight difference between the empty bags and the full bags was used to calculate the net WAP. Total net weight of pooled WAP was 1947 gr. The pooled material was mixed slowly at 25° C. until completely thawed (same stirring condition as in Example 9). The osmolarity of the pooled WAP was 265 mOs. 213 ml acetate-glycine buffer (to a final concentration of 20 mM sodium acetate, 10 mM glycine; at pH 6.8-7.4) and 1% v/v (from the final volume solution) Human serum albumin (HSA, Talecris USA) were added into the pooled WAP. In order to keep the osmolarity level as constant as possible throughout the process, the buffer osmolarity was adjusted to that of the WAP starting material using NaCl (Sigma-Aldrich, St. Louis, Mo., USA). S/D treatment was carried out as described previously by slowly adding 1% Triton X-100 and 0.3% TnBP (v/v) into the pooled sample while mixing at 50 RPM. In order to avoid sub-optimal viral inactivation due to the possible presence of particulate matter, during the S/D treatment the sample was filtered. Briefly, after S/D addition the sample was continuously stirred for 30 minutes and then filtered through 20, 3 and 1.2 µm Sartopure PP2 filters and 0.45 µm Sartopore 2 (Sartorius Stedim Biotech S.A., Aubagne, France). Then, the filtered material was returned to a beaker immersed in a water bath adjusted to 25° C. and mixed at 50 RPM for two additional hours for continuing the viral inactivation process.

S/D removal was carried out using XK50 liquid chromatography column packed with 295 ml SDR HyperD solvent-detergent removal chromatography resin (Pall Corp) in conjunction with a peristaltic pump and a UA-6 UV/VIS detector+Type 11 recorder (ISCO, NE, USA). 1800 ml of S/D-treated platelet extract (which contained 1620 ml of platelet material) were loaded onto the column followed by washing with 600 ml acetate glycine buffer+1% HSA. This was followed by elution with 900 ml of acetate glycine buffer containing 10% ethanol, 1M NaCl and 0.2% HSA. The column was finally washed with 600 ml of purified water. The unbound and the eluted material were collected. A total volume of 3600 ml was collected from the column.

To facilitate the precipitation of aggregates, $CaCl_2$ (40 mM final concentration) was slowly added to the extract following S/D removal procedure, as previously described, and the extract was incubated for 30 minutes at 25° C. while mixing at 50 RPM. The product was filtered using 20 and 3 µm Sartopure PP2 filters and 0.45 µm Sartopore 2 (Sartorius Stedim Biotech S.A., Aubagne, France). In the next step, the extract was subjected to stabilization and pasteurization as in Example 4. Removal of the stabilizers was carried out by diafiltration against acetate-glycine buffer (as above). The dialyzed solution was then concentrated to a volume of 530 ml (which is approximately 29% of the starting volume).

For stabilization, Mannitol was added into the solution at a final concentration of 2% w/w. In order to remove aggregated material, the sample was filtered through 3 µm Sartopure PP2 filter and 0.45 µm Sartopore 2 filter. Sterile filtration was carried out under aseptic conditions using a 0.2 µm Sartopore 2 filter. The obtained product (a volume of 452 ml) was then aliquot into 4 ml portions under aseptic conditions and lyophilized as elaborated above. The lyophilized material was sealed in nitrogen atmosphere in partial vacuum (0.6 Bar). The lyophilized platelet extract prepared above is referred herein as "LYO V".

The viral purification step of LYO V included S/D treatment which included a filtration sub step within the SD treatment. Filtration at this step was carried out through 20, 3, 1.2 and 0.45 µm filters. The SDR step included washing the column using non-isocratic solutions. The non-isocratic solution was acetate glycine buffer containing 10% ethanol, 1M NaCl and 0.2% HSA. In addition, a pasteurization step was carried out, and a final sterile filtration. During the dialysis step the volume of the dialyzed solution was concentrated about 3.5 times as compared to the starting volume.

The PDGF-AB content was measured in the material before loading the sample onto the SDR chromatography resin and after collecting the sample from the SDR resin (following solvent and detergent removal) in the production process of LYO II-LYO V. The percentage of recovery of the PDGF-AB in the different production processes (LYO II-LYO V) is shown in Table 4. PDGF-AB and bFGF content were measured using a specific commercial ELISA kit (Quantikine human PDGF-AB immunoassay; Manufacturer: R&D systems; cat. DHD00B, and Quantikine HS human bFGF cat. HSFB00D immunoassays; Manufacturer: R&D systems, respectively).

TABLE 4

Recovery of PDGF-AB and bFGF from SDR column in LYO II-V.

| LYO Number | Step | PDGF-AB content (ng) | PDGF-AB recovery (%) | bFGF content (ng) | bFGF recovery (%) |
|---|---|---|---|---|---|
| II | pre-SDR | 24941 | | 52 | |
| | post-SDR | 3942 | 16 | 18 | 35 |
| III | pre-SDR | 101313 | | 160 | |
| | post-SDR | 10807 | 11 | 40 | 25 |
| IV | pre-SDR | 70609 | | 218 | |
| | post-SDR | 9103 | 13 | 65 | 30 |
| V | pre-SDR | 86983 | | 274 | |
| | post-SDR | 38884 | 45 | 102 | 37 |

As shown in Table 4, the addition of the elution step with non isocratic solution in the S/D removal step as described above during processing of LYO V results in higher recovery of PDGF-AB. The recovery of PDGF-AB was 45% with the elution step as compared to 11-16% recovery in the absence of this step—about 3-fold recovery increase. The concentrations of PDGF-AB and bFGF were also measured in the final lyophilized material following reconstitution with 4 ml double distilled water (DDW). The concentration of PDGF-AB was 15,028 pg/ml which corresponds to $2.26 \times 10^{-6}$ pg PDGF-AB per platelet used as the starting material. The concentration of bFGF was 36 pg/ml which corresponds to $5.4 \times 10^{-9}$ pg bFGF per platelet used as the starting material.

Example 13: The Effect of LYO V on Cell Proliferation in Fibroblast Cells

The effect of LYO V on cell proliferation was carried out as elaborated in Example 5 using 3T3-Swiss albino cells.

LYO V, which was lyophilized from a 4 ml solution and that was concentrated 4-fold compared to the starting WAP volume, was reconstituted in 0.5 ml of sterile purified water—8-times concentrated (32-fold concentrated compared to the starting concentration of pooled WAP V). Following reconstitution, pooled WAP V or reconstituted LYO V were serially diluted 5-fold in the appropriate starvation medium and 10 µl of each dilution was added into a well containing 100 µl starvation medium. The starting concentration of pooled WAP V was designated as 1 and the serial dilutions were calculated accordingly. The starting concentration of LYO V was designated as 32 and the serial dilutions were calculated accordingly. As a standard control, a recombinant human PDGF-AB (R&D Systems; Cat. Number 222-AB-010) was used. The PDGF-AB was also serially diluted 5-fold in starvation medium and added into the wells (10 µl). Concentrations of several growth factors in both WAP V and LYO V were detected by ELISA (same kits as above) and the actual concentrations present in the well (in the highest concentration) during the proliferation assay are as follows: TGF-β—159.4 and 169.8 ng/ml; bFGF 0.1 ng/ml and 0.029 ng/ml; VEGF—0.89 and 1.05 ng/ml; PDGF-AB—56.86 and 12 ng/ml in wells treated with WAP V and LYO V, respectively.

Figure 17:
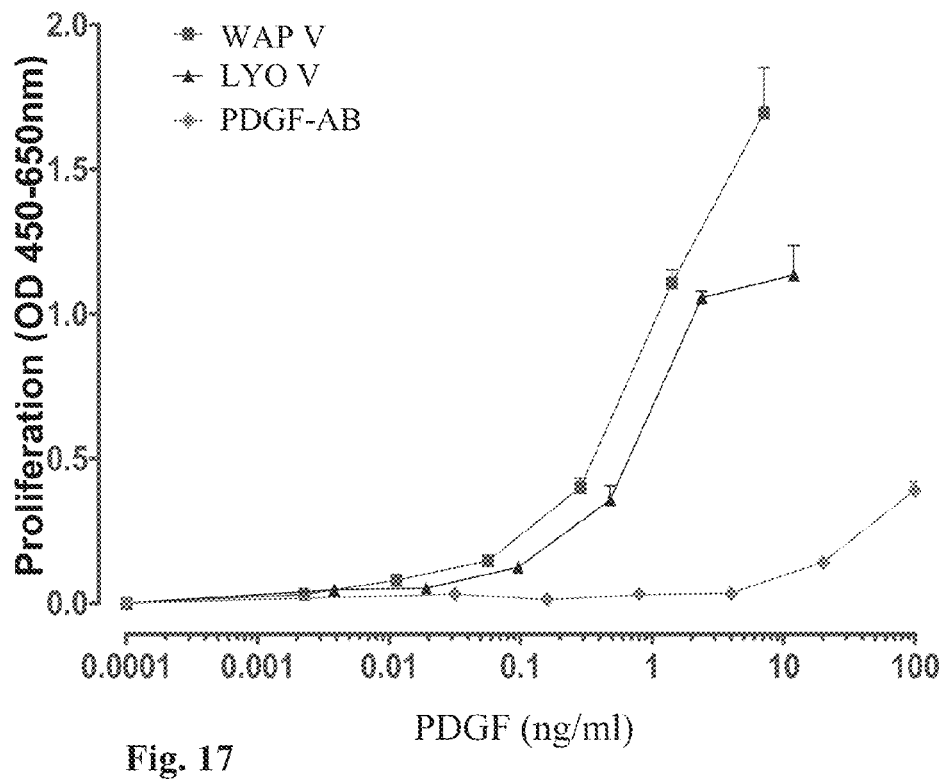
FIG. 17 shows the proliferative effect of LYO V or pooled WAP V on 3T3-Swiss albino fibroblasts. Recombinant human PDGF-AB was used as a control.

The proliferation was evaluated 72 hours after treatment initiation by using the WST-1 Cell Proliferation Reagent (cells without any additives were used as a background and subtracted from OD values). At the end of the incubation period (4 hours), the plates were shaken for 1 min and the absorbance of the samples was measured as indicated above. The tests were carried out in triplicates. The OD results obtained by the WST-1 Cell Proliferation Reagent were plotted against the calculated PDGF-AB concentration values. The results are shown in FIG. 17.

The results show that increasing concentrations of LYO V or pooled WAP V affected the proliferation level of 3T3-Swiss albino fibroblast cells with the effect of LYO V being slightly less pronounced. This apparent reduction was due to the normalization of the results to only one growth factor (PDGF-AB) that is present in the LYO mixture and the recovery of which was increased significantly comparing to the previous examples. Notably, the effect of both treatments (LYO V and WAP V) was more pronounced than the recombinant PDGF-AB alone, indicating that other platelets' extracted components may synergistically enhance fibroblasts proliferation.

Example 14: Comparison of the Manufacturing Steps Carried Out in LYO 1-LYO IV Prepared in the Above Examples Table 5 summarizes the major manufacturing steps carried out in each LYO preparations.

TABLE 5

Major manufacturing steps carried out in each LYO preparations.

| Major manufacture process step | LYO I | LYO II | LYO III | LYO IV | LYO V |
|---|---|---|---|---|---|
| Solvent-detergent treatment | + | + | + | + | + |
| Pasteurization (heat viral inactivation) |  | + | + | + | + |
| Concentration |  |  | + | + | + |
| Additional aggregate removal |  |  |  | + | + |
| Elution step added to SDR column* |  |  |  |  | + |

*Elution was carried out with a non isocratic solution: acetate glycine buffer (20 mM sodium acetate and 10 mM glycine at pH 6.8-7.4) containing 10% ethanol, 1M NaCl and 0.2% HSA.

Example 15: The Level of Aggregate Content in the Platelet Extract Prepared According to the Invention Aggregation is undesirable in protein pharmaceuticals because it can not only compromise biological activity but also increases the chance of undesirable side effects e.g. immunogenecity. The aggregation may also decrease protein stability. In the following example the aggregate content was determined in the platelet extracts prepared according to the invention.

For this purpose, the aggregation level (turbidity) was determined by measuring the optical density at 320 nm ($OD_{320}$) (which is typically indicative of the presence of aggregates as described in Ultraviolet absorption Spectroscopy, Mach H. et al., in Protein stability and folding, Ed. Shirley B. A. pp 91-114, 1995, Humana Press, New Jersey) and by subtracting the $OD_{320}$ reading of human serum albumin (HSA) which is present at high concentrations in the platelet extract and was considered to be a background reading. The normalized turbidity (aggregation) was obtained by dividing the turbidity (absorbance at 320 nm for an undiluted solution) by the protein concentration [determined by Pierce BCA Protein Assay (Thermo Fisher Scientific Inc., Rockford, Ill., USA; Cat. number 23235)] prior to the subtraction.

The aggregate level was calculated according to the following equation:

$$\frac{OD320 \text{ platelets extract}}{\text{mg protein/ml}} - \frac{OD320 \text{ human serum albumin}}{\text{mg protein/ml}} = OD320 \text{ platelet extract per mg protein}$$

An obtained calculated $OD_{320}$ level which was lower than ≤0.03 per mg protein was considered as a low aggregate content.

Different lyophilized platelet extracts prepared according to the above examples (LYO II-V) were reconstituted in DDW (to the same volume as before the lyophilization step). In the next step, a sample of 1 ml was transferred into acryl-cuvettes (Sarstedt, Cat. Number 67.740) and the OD was measured at 320 nm using Ultrospec 2100 pro spectrophotometer (Amersham Pharmacia Biotech). In parallel, the OD level of HSA was measured at 320 nm (in the same parameters as the tested extracts) and the aggregate level was calculated according to the above equation (different HSA concentrations were used and the reading was divided by the total protein of the solution as shown in the equation).

It was found that the calculated $OD_{320}$ level of all tested platelet extracts was <0.03 per mg protein. Therefore, the platelet extracts prepared according to the invention had low aggregate level.

Example 16: Lyophilized Platelet Extract Prepared from Pooled Washed Aphaeresis Platelets Leukocyte Reduced (WAP), Treated with S/D, SDR Elution Using Two Steps of Non-Isocratic Solutions, Pasteurized and Concentrated In this experiment a lyophilized platelet extract was prepared as follows: Ten WAP bags were individually weighed wiped with 70% ethanol, cut open and the frozen material was placed in a large beaker that was immersed in a water bath adjusted to 25° C. The empty bag was weighed and the weight difference between the empty bags and the full bags was used to calculate the net WAP weight. The total net weight of pooled WAP was 1906 gr. The pooled material was mixed slowly at 25° C. until completely thawed (same stirring condition as in Example 9). The osmolarity of the pooled WAP was 267 mOs. 209 ml acetate-glycine buffer (to a final concentration of 20 mM sodium acetate, 10 mM glycine; at pH 6.8-7.4) and 0.2% v/v (from the final volume solution) Human serum albumin (HSA, Talecris USA) were added into the pooled WAP. In order to keep the osmolarity level as constant as possible throughout the process, buffer osmolarity was adjusted to that of the WAP starting material using NaCl (Sigma-Aldrich, St. Louis, Mo., USA). S/D treatment was carried out as described previously by slowly adding 1% Triton X-100 and 0.3% TnBP (v/v) into the pooled sample while mixing at 50 RPM. In order to avoid sub-optimal viral inactivation due to the possible presence of particulate matter the sample was filtered during the S/D treatment. First, the sample was continuously stirred for 30 minutes and then filtered through 20 and 3 μm Sartopure PP2 filters and 0.45 μm Sartopore 2 (Sartorius Stedim Biotech S.A., Aubagne, France). Then, the filtered material was returned to a beaker immersed in a water bath adjusted to 25° C. and mixed at 50 RPM for additional 2 hours for continuing the viral inactivation process. S/D removal was carried out using XK50 liquid chromatography column packed with 295 ml SDR HyperD solvent-detergent removal chromatography resin (Pall Corp) in conjunction with a peristaltic pump and a UA-6 UV/VIS detector+Type 11 recorder (ISCO, NE, USA). 1800 ml of S/D-treated platelet extract (which contained 1620 ml of platelet material) were loaded onto the column followed by washing with 600 ml acetate glycine buffer+0.2% HSA. Heparin is known to bind certain growth factors. The effect of heparin in the recovery of growth factors in the elution step was explored. Thus, in this experiment elution was carried out with 600 ml of acetate glycine buffer containing 12.5% ethanol, 0.5M NaCl, 5 IU/ml Heparin (Heparin Sodium-Fresenium 5000 IU/ml, Bodene (PTY) Ltd, South Africa) and 0.2% HSA. This elution step was followed by a second elution step carried out with 600 ml of acetate glycine buffer containing 10% ethanol, 1M NaCl and 0.2% HSA. The column was finally washed with 300 ml of purified water. The unbound and eluted material were collected and polled. A total volume of 3700 ml was collected from the column. The collected material was filtered using 3 and 1.2 µm Sartopure PP2 filters and 0.45 µm Sartopore 2 (Sartorius Stedim Biotech S.A., Aubagne, France). In the next step, the extract was subjected to stabilization and pasteurization as in Example 4. Removal of the stabilizers was carried out by diafiltration against acetate-glycine buffer (as above). The dialyzed solution was then concentrated to a volume of 450 ml (which is approximately 25% of the starting volume).

For stabilization, Mannitol was added into the solution at a final concentration of 2% w/w. In order to remove aggregated material, the sample was filtered through 3 µm Sartopure PP2 filter and 0.45 µm Sartopore 2 filter. Sterile filtration was carried out under aseptic conditions using a 0.2 µm Sartopore 2 filter. The obtained sample was then aliquoted into 4 ml portions under aseptic conditions and lyophilized as elaborated above. The lyophilized material was sealed in nitrogen atmosphere in partial vacuum (0.6 Bar). The lyophilized platelet extract prepared above is referred herein as "LYO VI".

The viral purification step of LYO VI included S/D treatment which included a filtration sub step within the SD treatment. Filtration at this step was carried out through 20, 3, and 0.45 µm filters. The SDR step included several elution steps using non-isocratic solutions, one of them comprised 51 U/ml Heparin. In addition, a pasteurization step was carried out, and a final sterile filtration. During the dialysis step the volume of the dialyzed solution was concentrated 4 times as compared to the starting volume.

PDGF-AB and bFGF content was measured in the material before loading the sample onto the SDR chromatography resin and after collecting the sample from the SDR resin (following solvent and detergent removal) in the production process of LYO II-LYO IV and in LYO VI. The percentage of PDGF-AB and bFGF recovery after the SDR column in the different processes is shown in Table 6. PDGF-AB and bFGF content were measured using the specific commercial ELISA kit described above.

TABLE 6

Recovery of PDGF-AB and bFGF from SDR column in LYO II- VI.

| LYO | Step | PDGF-AB content (ng) | PDGF-AB recovery (%) | bFGF content (ng) | bFGF recovery (%) |
|---|---|---|---|---|---|
| II | pre-SDR | 24941 | | 52 | |
| | post-SDR | 3942 | 16 | 18 | 35 |
| III | pre-SDR | 101313 | | 160 | |
| | post-SDR | 10807 | 11 | 40 | 25 |
| IV | pre-SDR | 70609 | | 218 | |
| | post-SDR | 9103 | 13 | 65 | 30 |
| V | pre-SDR | 86983 | | 274 | |
| | post-SDR | 38884 | 45 | 102 | 37 |
| VI | pre-SDR | 103811 | | 196 | |
| | post-SDR | 42898 | 41 | 110 | 56 |

As shown in Table 6, addition of an elution step which comprises heparin significantly improved not only the recovery of PDGF-AB, but also the recovery of bFGF. The recovery of bFGF was 56% compared to 37% recovery in the absence of heparin in the non isocratic solution (LYO V)—about 1.5 fold increase in recovery. When comparing the recovery of bFGF in LYO VI to the Recovery in LYO II-IV, an increase of about 2 fold was observed.

The concentration of PDGF-AB and bFGF were also measured in the final LYO VI material following reconstitution with 4 ml double distilled water (DDW). The concentration of PDGF-AB and bFGF were 4,578 and 127 pg/ml, respectively, which corresponds to $7 \times 10^{-7}$ pg PDGF-AB per platelet and $1.95 \times 10^{-8}$ pg bFGF per platelet used as the starting material.

Example 17: The Effect of LYO VI on Cell Proliferation in Fibroblast Cells

The effect of LYO VI on cell proliferation was carried out as elaborated in Example 5 using 3T3-Swiss albino cells.

LYO VI, which was lyophilized from a 4 ml solution and that was concentrated 4-fold compared to the starting WAP volume, was reconstituted in 0.5 ml of sterile purified water—8-times concentrated as compared to the platelet extract before lyophilization (in all, it was 32-fold concentrated compared to starting volume of pooled WAP VI). Following reconstitution, pooled WAP VI or reconstituted LYO VI were serially diluted 5-fold in the appropriate starvation medium and 10 µl of each dilution was loaded into a well containing 100 µl starvation medium. The starting concentration of pooled WAP VI was designated as 2.5 (as it represents 2.5 µl of the platelet extract before lyophilization—10 µl of WAP which is 4 times diluted as compared to the platelet extract before lyophilization were used) and the serial dilutions were calculated accordingly.

The starting concentration of LYO VI tested was designated as 80 (as it represents 80 µl of the platelet extract before lyophilization—10 µl of an 8-times concentrated material following reconstitution of the lyophilized powder) and the serial dilutions were calculated accordingly. Concentrations of several growth factors in both WAP VI and LYO VI were measured by ELISA (same kits as above). The actual concentrations added to the well (in the highest concentration) during the proliferation assay are as follows: TGF-β—180 and 2000 ng/ml; bFGF—120 and 1000 pg/ml; VEGF—1.1 and 11.7 ng/ml; PDGF-AB—84.4 and 36.6 ng/ml; and EGF—3.6 and 24.4 ng/ml, in wells treated with WAP VI and LYO VI, respectively.

As a positive control, PRP-R was used. PRP-R was prepared from 10 donor pooled PRP. Briefly, 10 bags of whole blood, 400 ml/bag (obtained from MDA, Blood Bank, Israel) were each centrifuged at 850×g for 10 minutes at room temperature. 80 ml of the supernatant obtained of each bag were then separately centrifuged at 850×g for an additional 10 minutes at room temperature. 30 ml (obtained from each bag) of the PRP supernatant were collected and stored overnight at 2-8° C. The PRP was activated on the next day with 1.5 ml of 1000 IU/ml Thrombin and 1 ml of 2M $CaCl_2$ for 1 hour at room temperature, and then centrifuged at 3000 g for 10 minutes at 4° C. The supernatant of all 10 donors was finally pooled and mixed together for about 10 minutes by rolling movement. This pooled PRP-R stock (total volume of 170 ml) was used as the starting PRP-R material for this experiment. The concentrations of TGF-13, bFGF, VEGF, PDGF-AB, and EGF in the PRP-R were as follows: —15 ng/ml; —2 pg/ml; —90 pg/ml; —9 ng/ml; and—80 pg/ml. The prepared PRP-R was serially diluted 5 fold in the appropriate starvation medium, and 10 µl of the starting PRP-R and of each dilution was added into the wells. The starting concentration of the PRP-R was designated as 10 (as it is equivalent to the platelet extract before lyophilization).

Figure 18:
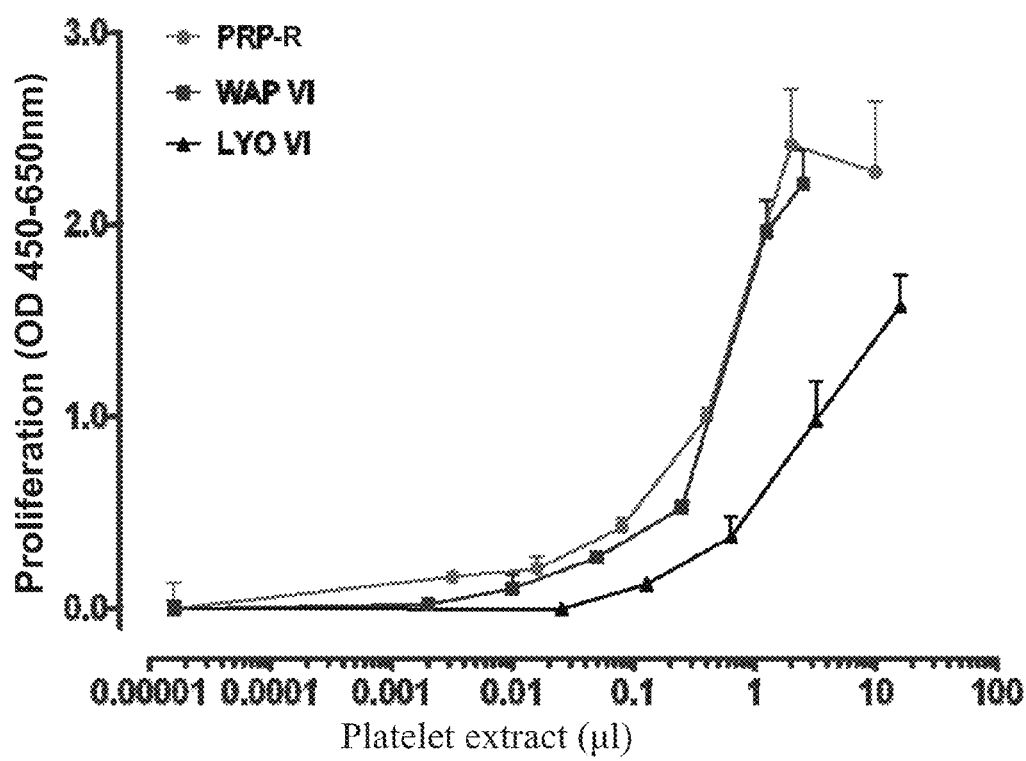
FIG. 18 shows the proliferative effect of LYO VI or pooled WAP VI on 3T3-Swiss albino fibroblasts. Pooled PRP releasate was used as a control.

The proliferation was evaluated 48 hours after treatment initiation by incubation with the WST-1 Cell Proliferation Reagent (cells without any additives were used as a background and subtracted from OD values). At the end of the incubation period (4 hours), the plates were shaken for 1 min and the absorbance of the samples was measured as indicated above. The tests were carried out in triplicates. The OD results obtained by the WST-1 Cell Proliferation Reagent were plotted against the platelet extract concentration values that were actually added to the cells (as explained above). The results are shown in FIG. 18. The results show that increasing concentrations of LYO VI, pooled WAP VI and PRP-R increased the proliferation level of 3T3-Swiss albino fibroblast cells with the effect of LYO VI being less pronounced.

Example 18: Lyophilized Platelet Extract Prepared from Pooled Washed Aphaeresis Platelets Leukocyte Reduced (WAP), Treated with S/D, Incubated with Dextran Sulfate, SDR Eluted with Dextran Sulfate, Pasteurized and Concentrated In this experiment a lyophilized platelet extract was prepared as follows: Ten WAP bags were individually weighed wiped with 70% ethanol, cut open and the frozen material was placed in a large beaker that was immersed in a water bath adjusted to 25° C. The empty bag was weighed and the weight difference between the empty bags and the full bags was used to calculate the net WAP. Total net weight of pooled WAP was 1916 gr. The pooled material was mixed slowly at 25° C. until completely thawed (same stirring condition as in Example 9). The osmolarity of the pooled WAP was 272 mOs. 211 ml acetate-glycine buffer (to a final concentration of 20 mM sodium acetate, 10 mM glycine; at pH 6.8-7.4) and 0.2% v/v (from the final volume solution) Human serum albumin (HSA, Talecris USA) were added into the pooled WAP. In order to keep the osmolarity level as constant as possible throughout the process, buffer osmolarity was adjusted to that of the WAP starting material using NaCl (Sigma-Aldrich, St. Louis, Mo., USA).

S/D treatment was carried out as described previously by slowly adding 1% Triton X-100 and 0.3% TnBP (v/v) into the pooled sample while mixing at 50 RPM. In order to avoid sub-optimal viral inactivation due to the possible presence of particulate matter, the S/D treatment was split into two parts. First, the sample was continuously stirred for 30 minutes and then filtered through 20 and 3 μm Sartopure PP2 filters and 0.45 μm Sartopore 2 (Sartorius Stedim Biotech S.A., Aubagne, France). Then, the filtered material was returned to a beaker immersed in a water bath adjusted to 25° C. and mixed at 50 RPM for additional 2 hours for continuing the viral inactivation process.

Dextran sulfate is known to bind certain growth factors. Thus, the effect of Dextran sulfate addition on the recovery of platelet factors was examined Dextran sulfate (Sigma-Aldrich, Canada; Cat. number D4911) was added to the sample to a final concentration of 1% (w/w) and incubated at 25° C. while stirring at 50 RPM for 20 minutes. The sample was filtered using 5 μm Sartopore PP2 filter to remove particulate matter.

Next, S/D removal was carried out using XK50 liquid chromatography column packed with 295 ml SDR HyperD solvent-detergent removal chromatography resin (Pall Corp) in conjunction with a peristaltic pump and a UA-6 UV/VIS detector+Type 11 recorder (ISCO, NE, USA). The column was equilibrated with 900 ml of acetate glycine buffer containing 1% dextran sulfate and 0.2% HSA. 1800 ml of S/D- and dextran sulfate-treated platelet extract (which contained 1620 ml of platelet material) were loaded onto the column followed by an elution step with 600 ml acetate glycine buffer with 12.5% ethanol, 0.5M NaCl, 0.1% dextran sulfate and 0.2% HSA. This was followed by washing with 600 ml of acetate glycine buffer containing 1% dextran sulfate and 0.2% HSA (consider as non isocratic compared to the solution used in the previous step). Next, the column was washed with 300 ml of purified water. A total volume of 3000 ml was collected from the column. The collected material was filtered using 3 and 1.2 μm Sartopure PP2 filters and 0.45 μm Sartopore 2 (Sartorius Stedim Biotech S.A., Aubagne, France). In the next step, the extract was subjected to stabilization and pasteurization as in Example 4. Removal of the stabilizers was carried out by diafiltration against acetate-glycine buffer (as above). The dialyzed solution was then concentrated to a volume of 480 ml (which is approximately 27% of the starting volume).

For stabilization, Mannitol was added into the solution at a final concentration of 2% w/w. In order to remove aggregated material, the sample was filtered through 3 μm Sartopure PP2 filter and 0.45 μm Sartopore 2 filter. Sterile filtration was carried out under aseptic conditions using a 0.2 μm Sartopore 2 filter. The obtained product was then aliquot into 4 ml portions under aseptic conditions and lyophilized as elaborated above. The lyophilized material was sealed in nitrogen atmosphere in partial vacuum (0.6 Bar).

The lyophilized platelet extract prepared above is referred herein as "LYO VII". The viral purification step of LYO VII included S/D treatment which included a filtration sub step within the SD treatment. Filtration at this step was carried out through 20, 3, and 0.45 μm filters. The platelet extract was treated with dextran sulfate prior to SDR removal. The SDR step included several elution steps using non-isocratic solutions in the presence of dextran sulfate. In addition, a pasteurization step was carried out, and a final sterile filtration. During the dialysis step the volume of the dialyzed solution was concentrated about 4 times as compared to the starting volume.

PDGF-AB and bFGF content was measured in the material before loading the sample onto the SDR chromatography resin and after collecting the sample from the SDR resin (following solvent and detergent removal) in the production process of LYO II-LYO IV and in LYO VII. The percentage of recovery of the PDGF-AB and bFGF in the different production processes is shown in Table 7. PDGF-AB and bFGF content was measured using the commercial ELISA kit described above.

TABLE 7

Recovery of PDGF-AB and bFGF from SDR column in LYO II-IV and in LYO VII.

| LYO | Step | PDGF-AB content (ng) | % PDGF-AB recovery | bFGF content (ng) | % bFGF recovery |
|---|---|---|---|---|---|
| II | pre-SDR | 24941 | | 52 | |
| | post-SDR | 3942 | 16 | 18 | 35 |
| III | pre-SDR | 101313 | | 160 | |
| | post-SDR | 10807 | 11 | 40 | 25 |

TABLE 7-continued

Recovery of PDGF-AB and bFGF from SDR column in LYO II-IV and in LYO VII.

| LYO | Step | PDGF-AB content (ng) | % PDGF-AB recovery | bFGF content (ng) | % bFGF recovery |
|---|---|---|---|---|---|
| IV | pre-SDR | 70609 | | 218 | |
|    | post-SDR | 9103 | 13 | 65 | 30 |
| V  | pre-SDR | 86983 | | 274 | |
|    | post-SDR | 38884 | 45 | 102 | 37 |
| VI | pre-SDR | 103811 | | 196 | |
|    | post-SDR | 42898 | 41 | 110 | 56 |
| VII| pre-SDR | 176249 | | 130 | |
|    | post-SDR | 154262 | 88 | 110 | 85 |

As shown in Table 7, addition of incubation with dextran sulfate and elution in the presence of dextran sulfate significantly improved the recovery of both, PDGF-AB and bFGF. The recovery of bFGF was 85% and the recovery of PDGF-AB was 88%.

Surprisingly, the recovery of PDGF-AB from the starting material in LYO VII was increased from 1.5% in LYO VI to 51% in LYO VII. Moreover, the recovery of VEGF from the starting material in LYO VII increased from 37% in LYO VI to 73% in LYO VII.

The concentration of PDGF-AB and bFGF were also measured in the final LYO VII material following reconstitution with 4 ml double distilled water (DDW). The concentration of PDGF-AB and bFGF were 194,353 and 64 pg/ml, respectively, which corresponds to $3.12 \times 10^{-5}$ pg PDGF-AB per platelet and $1.03 \times 10^{-8}$ pg bFGF per platelet used as the starting material.

These finding indicate that the addition of dextran sulfate to the process steps has a favorable effect on factors recovery also downstream from the SDR column.

Example 19: The Effect of LYO VII on Cell Proliferation in Fibroblast Cells

The effect of LYO VII on cell proliferation was carried out as elaborated in Example 5 using 3T3-Swiss albino cells.

LYO VII, which was lyophilized from a 4 ml solution and that was concentrated about 4-fold compared to the starting WAP volume, was reconstituted in 0.5 ml of sterile purified water—8-times concentrated (a total concentration of about 32 as compared to the starting volume of pooled WAP VII). Following reconstitution, pooled WAP VII or reconstituted LYO VII were serially diluted 5-fold in the starvation medium and 10 μl of each dilution was added into a well containing 100 μl starvation medium. As explained above, the starting concentration of pooled WAP VII was designated as 2.5 and the serial dilutions were calculated accordingly, and the starting concentration of LYO VII was designated as 80 and the serial dilutions were calculated accordingly. Concentrations of several growth factors in both WAP VII and LYO VII were measured by ELISA (same kits as above) and the actual concentrations added to the well (in the highest concentration) during the proliferation assay are as follows: TGF-β—260 and 2800 ng/ml; bFGF—190 and 510 pg/ml; VEGF—1.1 and 21 ng/ml; PDGF-AB—114 and 1550 ng/ml; PDGF-BB—21 and 150 ng/ml; and EGF—3.1 and 33.1 ng/ml, in WAP VII and LYO VII, respectively.

Additionally, WAP VI and LYO VI, prepared as in example 16 were tested in the same assay for activity comparison (10 μl of the serial dilutions described in Example 16; standardization to platelet extract units were carried out as described in Example 17).

Figure 19:
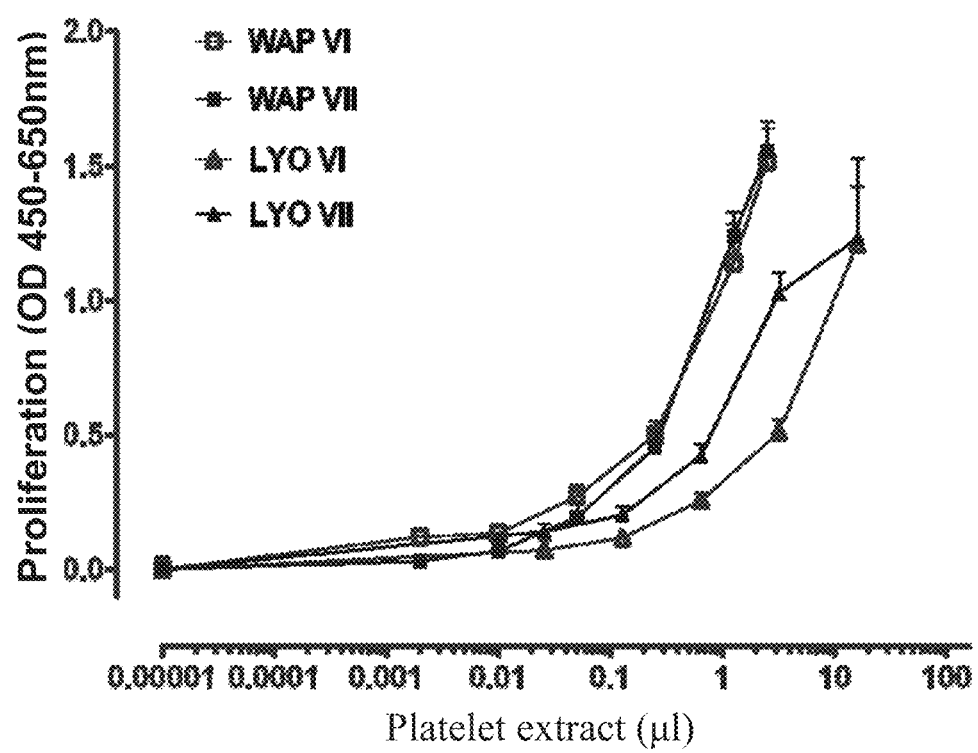
FIG. 19 shows the proliferative effect of LYO VI and pooled WAP VII; or LYO VII and pooled WAP VII on 3T3-Swiss albino fibroblasts.

The proliferation was evaluated 48 hours after treatment initiation by using the WST-1 Cell Proliferation Reagent (cells without any additives were used as a background and subtracted from OD values). At the end of the incubation period with the reagent (4 hours), the plates were shaken for 1 min and the absorbance of the samples was measured as indicated above. The tests were carried out in triplicates. The OD results obtained by the WST-1 Cell Proliferation Reagent were plotted against the platelet extract units before lyophilization that were actually added to the cells (as explained above). The sigmoidal dose response analysis was carried out using GraphPad Prism software and the EC50 values are shown on the graph. The results are shown in FIG. 19. The results clearly show that LYO VII (EC50 1.26) is more potent in induction of fibroblasts proliferation as compared to LYO VI (EC50 4.10), whereas their starting materials WAP VII and WAP VI (EC50 0.36 and 0.32, respectively), affected the proliferation level of fibroblasts to the same extent. The proliferative effect of LYO VII was more pronounced and closer to the starting WAP than that of LYO VI.

Example 20: Comparison of the Manufacturing Steps Carried Out in LYO II-VII Prepared in the Above Examples Table 8 summarizes the manufacturing steps carried out in all LYO preparations.

TABLE 8

Manufacturing steps carried out in all LYO preparations.

| Manufacture process steps | LYO I | LYO II | LYO III | LYO IV | LYO V | LYO VI | LYO VII |
|---|---|---|---|---|---|---|---|
| Solvent-detergent treatment | + | + | + | + | + | + | + |
| Pasteurization (heat viral inactivation) | | + | + | + | + | + | + |
| Concentration | | | + | + | + | + | + |
| Additional aggregate removal | | | | + | + | | |
| Additional incubation with dextran sulfate | | | | | | | + |

TABLE 8-continued

Manufacturing steps carried out in all LYO preparations.

| Manufacture process steps | LYO I | LYO II | LYO III | LYO IV | LYO V | LYO VI | LYO VII |
|---|---|---|---|---|---|---|---|
| Elution step added to SDR column using a non isocratic solution | | | | | +* | +** | +*** |

*Elution was carried out in the presence of ethanol, and NaCl.
**Elution was carried out in the presence of heparin.
***Elution was carried out in the presence of dextran sulfate.

Example 21: The Ratio Between Several Growth Factors in Platelet Extracts Prepared According to the Invention The following Example shows the ratio between several growth factors in the platelet extract prepared according to the invention; and examines whether the obtained ratio is close to the physiological ratio. The physiological ratio was calculated according to growth factor values in the serum. The values were obtained from the package inserts of the specific ELISA kit used for the growth factor measurements above.

Serum is blood plasma without fibrinogen or other clotting factors. The serum contains factors released by activated platelets.

The levels of TGF-b1, PDGF-AB and VEGF were measured in LYO VII (following its reconstitution in 4 ml DDW) using the specific commercial ELISA kit described above, and the ratios between PDGF-AB:TGFb1, and PDGF-AB:VEGF were calculated. The growth factor's level and ratios are shown in Table 9 and 10, respectively, below.

TABLE 9

Levels* of TGF-b1, PDGF-AB and VEGF in LYO VII and in the serum.

| Growth factor | Serum** | LYO VII |
|---|---|---|
| TGF-b1 | 40 | 343 |
| PDGF-AB | 20 | 194 |
| VEGF | 0.22 | 2.6 |

*Values are in ng/ml.
**Mean of detectable values in the serum obtained from the package inserts of the specific ELISA kit used for the measurements above.

TABLE 10

Calculated growth factor's ratio in LYO VII and in the serum.

| | PDGF-AB:TGF-b1 Ratio | PDGF-AB:VEGF Ratio |
|---|---|---|
| Serum | 0.5 | 90.9 |
| LYO VII | 0.56 | 74 |

The results presented in Table 10 show that LYO VII comprises a PDGF-AB:TGF-b1 ratio of 0.56 (similar to the physiological ratio in the serum-0.5); and a PDGF-AB:VEGF ratio of 74. Both ratios were found to be within the calculated ratio in the starting materials (WAPs) of the above Examples.

Example 22: The Coagulation Activity of Platelet Extract Prepared According to the Invention The following experiment was aimed to determine whether LYO VI-VII have a pro-coagulant activity. The presence of activated coagulation factors in the platelet extracts was assessed by the non-activated partial thromboplastin time measurement test (NAPTT). This test is based on the assay described in the European Pharmacopoeia 7.0; 2.6.22: Activated coagulation factors monograph (01/2008: 20622); in European Pharmacopoeia Strasburg (France), Council of Europe, 2009.

In general, the test includes addition of phospholipids (Rabbit Brain Cephalin, Pel-Freez, Cat. Number 41053-2) and calcium to human plasma to enable the initiation of the coagulation cascade. The non-active coagulation factors contained in the human standard plasma (Unicalibrator, Diagnostica Stago, cat. 0625 or Coagulation Reference, TC technoclone, ref. 5220120) undergo activation following the addition of a sample containing active coagulation factors leading to transformation of plasma prothrombin to active thrombin. As a result, the plasma fibrinogen immediately transforms to insoluble fibrin (clot formation) and the clotting time can be measured by a coagulometer (STart4 Coagulation Instrument, Diagnostica Stago, Asnières sur Seine, France). The process of factor activation in the above reference control sample usually takes 4-7 minutes. In a parallel experiment, a sample of platelet extract is added into the human standard plasma and the clotting time is measured as above. The obtained result is divided by the result of the reference control sample. The calculated ratio serves as a measure of the pro-coagulant activity of the tested platelet extract sample. A ratio of lower than 1 means that the tested sample contains activated coagulation factors and thus has a pro-coagulant activity.

The tested platelet extract was reconstituted with 4 ml purified water (PuW) prior to the measurement.

TABLE 11

Pro-coagulant activity of LYO VI-VII.

| | Ratio* sample time/control time |
|---|---|
| LYO VI | 1.2 |
| LYO VII | 1.3 |

*Average of three measurements.

The results presented in Table 11 show that the platelet extract prepared according to the invention does not have a pro-coagulant activity as assessed by the NAPTT assay.

Example 23: Determination of the Presence of Coagulation Factors in the Platelet Extract Prepared According to the Invention The following experiment was aimed to determine whether LYO VI-VII comprise coagulation factors. The presence of coagulation factors (activated and non-activated factors) in the platelet extracts was determined by the Activated Partial Thromboplastin Time (APTT) [also known as Kaolin Cephalin Clotting Time (KCCT); or Partial Thromboplastin Time with Kaolin (PTTK)].

The APTT is a general coagulation screening test of the intrinsic coagulation pathway that can assess the potential of plasma-derived samples to undergo coagulation. The APTT detects the presence of the following coagulation factors: factors XII, XI, IX, VIII, X, V, II (prothrombin), and I.

The assay involves the recalcification of plasma in the presence of a standardized amount of cephalin (i.e. phospholipids) and a factor XII activator (kaolin). The assay is designed as a limit test, in which the tested sample should show no coagulation after 999 seconds.

The assay was carried out by using KIT reagents C.K. PREST®, Diagnostica Stago, ref 00597 (containing Reagent 1 and Reagent 2) according to the manufacturer's instructions. The tested LYO was reconstituted with 4 ml purified water (PuW) prior to carrying out the APTT test.

TABLE 12

Determination of the presence of coagulation factors.

| Sample | Replicates (name) | Clotting time (sec) | Average (sec) | RSD* duplicate (%) |
|---|---|---|---|---|
| Sys Suitability Solution (Positive Control) | 1 | 30.0 | 30.4 | 1.6 |
| | 1 | 30.7 | | |
| | 2 | 30.9 | 30.9 | |
| | 2 | 30.8 | | |
| LYO VI | 1 | >999 | >999 | |
| | 1 | >999 | | |
| | 2 | >999 | | |
| | 2 | >999 | | |
| LYO VII | 1 | >999 | >999 | |
| | 1 | >999 | | |
| | 2 | >999 | | |
| | 2 | >999 | | |

*RSD—Relative Standard Deviation.

The results show that according to the APTT test, the platelet extract according to the invention is deficient in one or more of the coagulation factors XII, XI, IX, VIII, X, V, II, and I, rendering the extract non-clottable.

Example 24: The Effect of Platelet Extract Prepared According to the Invention on the Level of Angiogenesis and Overall Healing in an In Vivo Model The effect of platelet extract prepared according to the invention on angiogenesis and overall healing was examined using the Subcutaneous Implantation Model in Rats. This model is commonly used to assess tissue response, angiogenesis and overall healing in the implanted tissue [International Organization for Standardization (ISO) 10993-6, Biological Evaluation of Medical Devices—Part 6: Tests for Local Effects After Implantation (2007)].

The two parameters were evaluated 3 and 7 days following the implantation.

10 female rats were used in this experiment. Each animal had two subcutaneous pockets surgically created in the subcutaneous tissues along both sides of the back (4 pockets in total). Each pocket was filled with one of the following tested articles: fibrin sealant+1× platelet extract, fibrin sealant+0.1× platelet extract (10% of the amount of platelet extract used in 1×), fibrin sealant alone, and saline.

Preparation and Administration of the Tested Articles:

Fibrin sealant+1× platelet extract–1× platelet extract was prepared by reconstituting a lyophilized platelet extract prepared from a 4 ml platelet extract solution as in Example 16 (similar to the preparation of LYO VI) with 2 ml of fibrinogen solution (a solution as in the BAC component of EVICEL™ fibrin sealant, Omrix Biopharmaceuticals Ltd.). 100 µl from the platelet extract-fibrinogen mixture was mixed with 100 µl thrombin solution (a solution as in the thrombin component of EVICEL™ fibrin sealant, Omrix Biopharmaceuticals Ltd., but diluted to a concentration of 20 IU/ml in 40 mM calcium chloride solution; the final thrombin concentration was 10 IU/ml). The 200 µl platelet extract-fibrinogen-thrombin mixture was administered into one of the above created pockets.

Fibrin sealant+0.1× platelet extract–0.1× platelet extract was prepared by lyophilizing 400 µl platelet extract solution prepared as in Example 16, and reconstituting the lyophilizate with 2 ml fibrinogen solution. 100 µl from the ml platelet extract-fibrinogen mixture was mixed with 100 µl diluted thrombin solution (the fibrinogen and diluted thrombin solutions used are as specified above). The 200 µl platelet extract-fibrinogen-thrombin mixture was administered into a second pocket.

The amounts of several growth factors actually administered in 0.1× and 1×, respectively: TGF-b1: 5.27 and 52.7; PDGF-AB 0.1 and 1.05; bFGF 0.0024 and 0.024; and VEGF 0.023 and 0.23 ng (administered with 200 µl fibrin sealant).

Fibrin sealant—100 µl fibrinogen solution was mixed with 100 µl diluted thrombin solution (as above). The final mixture was administered into the third pocket.

Saline—200 µl saline was administered into the fourth pocket and was used as the control group.

Administration of the four tested articles was carried out adjacent to a location marker [steam sterilized high density polyethylene (HDPE) 1 mm×1 mm×5 mm in size] placed within each pocket (in order to mark the exact location of the administration for later evaluations).

Five animals were humanely sacrificed at each time point (day 3 and 7 post-implantation) and all four implant sites (from each animal at each time point) were collected and immersed in 10% neutral buffered formalin. Multiple sections were cut from each implant site and the sections were processed for microscopic evaluation. The histology sections were stained with Hematoxylin and Eosin.

Angiogenesis and overall healing in the implanted region of the different tested groups were microscopically evaluated by using the below specified subjective grading scale:

Angiogenesis Grading Scale:
  0=none; 1=poor: limited, focal or segmental with limited penetration of article, 1-3 neovascular buds and limited fibroblastic supporting structures; 2=fair: focal, multifocal, or diffuse with penetration into article and groups of capillaries evident with adequate fibroblastic support; 3=good: article completely penetrated by tissue and capillaries with fibroblastic supporting structures; and 4=excellent: better than expected for the study interval evaluated.

Overall Wound Healing Grading Scale:
  0=none; 1=poor: less than control implant site, less than expected for surgical procedure and time post-implantation; 2=fair: almost or the same as control implant sites, about what is expected for the surgical procedure and time post-implantation; 3=good: slightly better than expected for surgical procedure and time post-implantation; and 4=excellent: more than expected for time post-implantation.

The average scoring value for angiogenesis and healing of the different tested articles are shown in Table 13 below.

TABLE 13

Average scoring of angiogenesis and overall healing following implantation of the different tested articles in the different time intervals.

| Study Interval (days) | Tested Article | Angiogenesis score | Overall healing score* |
|---|---|---|---|
| 3 | Fibrin sealant + 1X platelet extract | 1.0 | NA |
|  | Fibrin sealant + 0.1X platelet extract | 1.0 | NA |
|  | Fibrin Sealant | 1.0 | NA |
|  | Saline | 0.8 | NA |
| 7 | Fibrin sealant + 1X platelet extract | 2.0 | 3-4 |
|  | Fibrin sealant + 0.1X platelet extract | 1.4 | 2-3 |
|  | Fibrin Sealant | 1.0 | 1-2 |
|  | Saline | 0.0 | 2 |

*Overall healing could not be scored appropriately 3 days following implantation due to the very short study interval (not enough time for "healing" to be microscopically apparent).

No deleterious effect was observed following treatment with the various tested articles in both intervals (as microscopically determined by the presence of low numbers of macrophages and lymphocytes in the implant site).

No significant differences or trends were observed between the different tested articles in the two tested parameters 3 days post-implantation. Thus, 3 days interval served as a baseline for the remaining study interval.

At 7 days post-implantation, the fibrin sealant+1× platelet extract was associated with more angiogenesis and better overall healing as compared to the other tested articles (see Table 13 with the average score). The 7 day angiogenesis grade for fibrin sealant+1× platelet extract was greater than that observed at 3 days post-implantation.

The fibrin sealant+0.1× platelet extract showed a trend towards more angiogenesis and better overall healing as compared to fibrin sealant alone and saline tested articles.

Example 25: The Effect of Different Non-Isocratic Conditions During an Elution Step in the S/D Removal Step In the following example the effect of different elution conditions during the HIC S/D removal step on recovery of PDGF-AB and bFGF was examined.

The experiments were carried out using two different types of hydrophobic resins: HyperD SDR (PALL), and C-18 (Waters). Both are silica based. The C-18 has a 18-carbon hydrophobic polymer moiety, whereas the HyperD has a hydrophobic polymer cross-linked to silica beads and involves a mixed-mode adsorption associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

2 ml of the resin were packed in a 1 cm diameter Bio-Rad column (small scale experiments). The maximal flow rate used was: 0.3 ml/min.

In all the experiments below S/D treated platelet lysate was prepared as follows: 10 ml of washed apheresis platelets leukocyte reduced (WAP) containing 20 mM sodium acetate, 10 mM glycine and 1% HSA v/v (from the final volume solution) were thawed at 37° C. (the pooled WAP material was frozen after addition of acetate-glycine-HSA buffer). In the next step, 1% Triton X-100 and 0.3% TnBP were added into the solution, and the solution was incubated and mixed (on a tube roller) at room temperature (22±2° C.) for 2 hours for platelet lysis and antivirus treatment. The lysate was then filtered through 10 μm and 5 μm syringe filters to remove any particulate matter.

Unless indicated otherwise, the packed column with the resins was washed prior to loading the S/D treated lysate with 10 ml Purified Water, and equilibrated with 10 ml acetate-glycine-HSA buffer (same concentrations as above; at the tested pH level). In the next step, 9 ml of the S/D-treated lysate were loaded onto the column followed by washing with 10 ml acetate glycine buffer+HSA (same concentrations as above; at the tested pH level). This washing step was followed by different elution steps with 10 ml of a supplemented Acetate-Glycine-HSA buffer (a non isocratic solution) as elaborated below. The wash and eluted material was collected and pooled.

In all the experiments, PDGF-AB and bFGF content was measured in the lysate before loading the sample to the chromatography resin and after collecting the sample from the resin (following solvent and detergent removal), and the percentage of recovery of the factor was calculated in the different elution steps. The content of both factors was measured using the specific commercial ELISA kit described above.

The first set of experiments examined the effect of NaCl content and pH level of the Acetate-Glycine-HSA buffer during S/D removal on the recovery of PDGF-AB. Acetate-Glycine-HSA buffer was supplemented with different NaCl concentrations (0.3-1.5 M), and an SDR elution step was carried out using the supplemented buffer as a non-isocratic solution.

TABLE 14

The effect of NaCl concentration and pH on PDGF-AB recovery from SDR or C-18 resin.

|   | Resin | pH | NaCl Concentration (M) | PDGF-AB Recovery (%) |
|---|---|---|---|---|
| 1 | C-18 | 5.5 | 0.3 | 19.0 |
| 2 | C-18 | 7 | 0.5 | 19.8 |
| 3 | C-18 | 7 | 0.7 | 20.6 |
| 4 | C-18 | 7 | 1 | 31.4 |
| 5 | C-18 | 5.5 | 1 | 30.5 |
| 6 | C-18 | 7 | 1.5 | 24.4 |
| 7 | SDR | 7 | 0.7 | 30.2 |
| 8 | SDR | 7 | 1.5 | 32.4 |

The results show that when using a C-18 resin, a positive correlation exists between NaCl concentration in the elution buffer and PDGF-AB recovery following HIC using a concentration ranging from 0.3 M up to 1M NaCl. Optimal results were obtained at a concentration of 1 M (about 30% PDGF-AB recovery). The tested pH did not affect the recovery.

When using SDR resin, similar recoveries were obtained in all NaCl tested concentrations (0.7 and 1.5 M). Also, it was observed that a higher PDGF-AB recovery was obtained when using SDR as a resin as compared to when using C-18 as the resin (compare PDGF-AB recovery in 3 and 7).

Another set of experiments examined the effect of addition of both NaCl and ethanol into the Acetate-Glycine-HSA buffer during S/D removal on the recovery of PDGF-AB from an SDR or C-18 column. For this purpose, Acetate- Glycine-HSA buffer was supplemented with different NaCl and ethanol concentrations and an SDR elution step was carried out using the supplemented buffer as a non-isocratic solution.

TABLE 15

Efficiency of NaCl and ethanol elution on PDGF-AB recovery from SDR or C-18 column.

|   | Resin | pH | NaCl (M) | EtOH (%) | PDGF-AB Recovery (%) |
|---|---|---|---|---|---|
| 1 | C-18 | 7 | 0.5 | 10 | 28.2 |
| 2 | C-18 | 7 | 0.5 | 20 | 32.1 |
| 3 | C-18 | 7 | 1.0 | 20 | 48.8 |
| 4 | SDR | 7 | 0.5 | 20 | 46.8 |
| 5 | SDR | 7 | 1.0 | 10 | 41.7 |
| 6 | SDR | 7 | 1.0 | 20 | 73.1 |

The results show that adding ethanol to the solution in addition to NaCl resulted in a higher recovery as compared to using NaCl alone (compare 1 and 2 from Table 15 with 2 of Table 14; and 3 of Table 15 with 4 of Table 14). It was also observed that the maximal PDGF-AB recovery was obtained with 1 M NaCl and 20% ethanol in both resin types with SDR resin having a higher recovery.

In the previous set of experiments it was shown that a maximal PDGF-AB recovery was obtained with Acetate-Glycine-HSA buffer supplemented with 1 M NaCl and 20% ethanol in both resin types. In the following set of experiments, the efficacy of S/D material (TritonX-100 and TnBP) removal under the same conditions (Acetate-Glycine-HSA buffer supplemented with 1 M NaCl and 20% ethanol) was evaluated. Of note, the acceptable limit of each one of Triton X-100 and TnBP in blood-derived products is 5 µg/ml. The concentration of Triton X-100 and TnBP in the collected fractions was measured following the S/D removal step. Triton x-100 is determined by reversed phase HPLC with a U.V. detector, and TnBP is determined by capillary gas chromatography using a Flame Ionization Detector. The level of S/D material was also evaluated in an S/D treated lysate prepared in a similar manner as LYO IV which was not subjected to elution by non isocratic conditions (large scale preparation, but the procedure was stopped following the S/D removal step). The results are shown in Table 16 below.

TABLE 16

S/D material concentration in the material collected after SDR or C-18 chromatography.

|   | Resin | pH | NaCl (M) | EtOH (%) | TritonX-100 (µg/ml) | TnBP (µg/ml) |
|---|---|---|---|---|---|---|
| 1 | C-18 | 7 | 0.5 | 10 | 0.3 | <0.2 |
| 2 | C-18 | 7 | 0.5 | 20 | 0.2 | <0.2 |
| 3 | C-18 | 7 | 1.0 | 20 | 0.6 | <0.2 |
| 4 | SDR | 7 | 0.5 | 20 | 0.3 | <0.2 |
| 5 | SDR | 7 | 1.0 | 20 | 5.7 | 2.5 |
| similar to LYO IV | SDR | 7 | 1.0 | 10 | <0.2 | NA* |

*NA—not available.

The results show that carrying out an elution step with 1 M NaCl and 20% ethanol (determined as efficient for PDGF-AB recovery in the previous experiments) resulted in the presence of relatively high amounts of S/D material (e.g. a Triton X-100 concentration of 5.7 or 0.6 µg/ml) in the platelet solution. However, when lower concentrations of NaCl and/or ethanol were used, lower concentrations of both TritonX-100 and TnBP were detected in the platelet solution following the S/D material removal step.

Also, the results show that under the same experimental conditions, lower S/D material was detected when using C-18 resin as compared to using SDR resin (compare 2 with 4; and 3 with 5).

In the next step, the recovery of b-FGF was examined by carrying out an elution step during the SDR step with a combination of NaCl and ethanol. Different ionic strengths and different ethanol concentrations were examined. In this experiment SDR resin was used.

TABLE 17

The effect of NaCl and ethanol added to the Acetate-Glycine-HSA buffer on bFGF recovery from SDR column.

|   | PH | NaCl (M) | EtOH (%) | b-FGF Recovery (%) |
|---|---|---|---|---|
| 1 | 8 | 0 | 0 | 9.6 |
| 2 | 7 | 0.5 | 20 | 15.4 |
| 3 | 8 | 0.5 | 20 | 24.3 |
| 4 | 7 | 1 | 10 | 18.5 |
| 5 | 8 | 1 | 10 | 21.5 |

The results showed that the tested non-isocratic conditions which were shown to effectively improve PDGF-AB recovery had a smaller effect on the recovery of b-FGF (compare 1 with 2-5).

In order to attempt to increase the recovery of b-FGF and further increase the recovery of PDGF-AB during the elution step, the effect of Heparin addition to the non-isocratic solution was examined Heparin was tested since it is known to bind some growth factors. In this experiment an SDR resin was used. The results of b-FGF recovery under the different elution conditions are shown in Table 18 below.

TABLE 18

The effect of Heparin combined with NaCl/ethanol during an elution step on b-FGF recovery from SDR column.

|   | pH | Heparin (IU/ml) | NaCl (M) | EtOH (%) | b-FGF Recovery (%) |
|---|---|---|---|---|---|
| 1 | 7 | 10 | 0 | 0 | 16.4 |
| 2 | 7 | 100 | 0 | 0 | 17.5 |
| 3 | 7 | 2 | 0.5 | 12.5 | 44.3 |
| 4 | 7 | 5 | 0.5 | 12.5 | 44.8 |
| 5 | 7.5 | 5 | 0.5 | 15 | 44.2 |
| 6 | 7 | 30 | 0.5 | 15 | 55 |
| 7 | 7.3 | 5 | 1.0 | 10 | 22.1 |

The results showed that heparin alone at concentrations of 10 and 100 IU/ml had a low positive effect (compare 1 and 2 from Table 18 with 1 from Table 17). However, combination of heparin at a concentration range of 2-30 IU/ml with NaCl at a concentration of 0.5 M and ethanol at a concentration range of 12.5-15% resulted in a synergistic increased recovery of b-FGF as compared to using heparin alone (compare 3-6 with 1-2). An increase in the NaCl concentration from 0.5 M to 1 M along with reduction of ethanol concentration to 10% resulted in a recovery decrease to about 22%.

The results also showed that under the tested conditions, addition of heparin during the elution step did not affect the recovery of PDGF-AB (data not shown).

In order to try to further increase the recovery of PDGF-AB and b-FGF from the SDR column, in the following experiment the lysate was incubated with dextran sulfate prior to S/D removal step and/or was added in the elution steps. Like heparin, dextran sulfate is a sulfated polysaccharide capable of binding various growth factors and stabilizing b-FGF, and VEGF [Kajio, Kawahara & Kato (1992) FEBS v306 p 243-6; Huang et al., (2007) Biomacromolecules v8 p 1607-14]. The washings and the elutions were carried out in the order elaborated in Table 19.

Dextran sulfate (0.1% or 1%) was tested alone or in combination with NaCl and EtOH. Incubation of the lysate with dextran sulfate (condition I-L) was carried out for 15 min at room temperature.

TABLE 19

PDGF-AB and b-FGF recovery at the different conditions.

| Con. | Incubation prior to S/D removal | Eq. buffer | Elution 1 buffer | | | Elution 2 buffer | | | PDGF-AB (%) | b-FGF (%) |
|---|---|---|---|---|---|---|---|---|---|---|
| | | | NaCl (M) | EtOH (%) | D.S. (%) | NaCl (M) | EtOH (%) | D.S. (%) | | |
| A* | none | AGH | 0.5 | 12.5 | 5 IU/ml Heparin | 1 | 10 | — | 27 | 49 |
| B* | none | AGH | 1 | 10 | — | 0.5 | 12.5 | 5 IU/ml Heparin | 29 | 26 |
| C* | none | AGH | — | — | 1 | 1 | 10 | 1 | 38 | 22 |
| D* | none | AGH | 1 | 10 | 1 | — | — | 1 | 36 | 28 |
| E* | none | AGH | — | — | 1 | 0.5 | 12.5 | 0.1 | 38 | 32 |
| F* | none | AGH | 0.5 | 12.5 | 0.1 | — | — | 1 | 38 | 40 |
| G* | none | AGH | 0.5 | 12.5 | 0.1 | 1 | 10 | 1 | 44 | 33 |
| H* | none | AGH | 1 | 10 | 1 | 0.5 | 12.5 | 0.1 | 47 | 33 |
| I** | 1% D.S. | AGH + D.S. 1% | 0.5 | 12.5 | 0.1 | — | — | 1 | 53 | 40 |
| J** | 1% D.S. | AGH + D.S. 1% | 1 | 10 | 1 | 0.5 | 12.5 | 0.1 | 60 | 46 |
| K | 1% D.S. | AGH + D.S. 1% | 0.5 | 12.5 | 0.1 | — | — | 1 | 62 | 51 |
| L | 1% D.S. | AGH + D.S. 1% | 1 | 10 | 1 | 0.5 | 12.5 | 0.1 | 55 | 40 |

*Conditions included a washing step with Ac-Gly-HSA prior to elution 1.
**Conditions included an additional elution step with Acetate-Glycine-HSA buffer prior to elution 1 and 2.
"Conditions" - is abbreviated to Con.;
"Equilibration" - is abbreviated to Eq.;
"Acetate-Glycine-HSA" - is abbreviated to AGH;
"Dextran sulfate" - is abbreviated to D.S.

As seen in Table 19, the sequence of elution solutions plays a role in the recovery level of PDGF-AB and b-FGF. For example, compare the recovery of condition A with B or E and F, wherein the elution order was reversed and the recovery of the growth factors was affected.

Also, buffer composition affects the recovery of the tested growth factors, with condition K being the most favorable for PDGF-AB and b-FGF recovery (62% and 51%, respectively).

The invention claimed is:

1. A non-clottable viral-safe platelet extract derived from multiple donors, comprising PDGF-AB, VEGF and TGF-β1 and made by the steps comprising:
   (a) contacting a platelet-enriched fraction with solvent detergent (S/D) as a first viral inactivation treatment; contacting the fraction with a molecule capable of binding platelet-derived factors selected from the group consisting of dextran sulphate, wherein the S/D is removed from a resultant platelet lysate by hydrophobic interaction chromatography (HIC), the HIC comprising the steps of:
      (i) equilibrating the HIC column with a composition comprising a molecule capable of binding platelet-derived factors selected from the group consisting of dextran sulphate;
      (ii) loading the platelet lysate to the equilibrated HIC of step (i);
      (iii) Optionally, washing the loaded HIC of step (ii) with an isocratic solution and collecting the unbound material;
      (iv) washing HIC with a non isocratic solution; and collecting the eluted material;
   and wherein washing and collected steps comprise a molecule capable of binding platelet-derived factors selected from the group consisting of dextran sulphate; and
   (b) conducting a second orthogonal viral inactivation treatment,
   wherein the ratio of PDGF-AB:VEGF in the viral safe platelet extract made by steps (a)-(b) is at least 45, and wherein the PDGF-AB content is at least 51% of the total PDGF-AB content of the extract as compared to a PDGF-AB content in the extract that was not rendered viral-safe by steps (a)-(b) above.

2. The extract according to claim 1, comprising PDGF-AB, VEGF and TGFb1, wherein the ratio for PDGF-AB:TGF-b1 is at least 0.2.

3. The extract according to claim 1, enriched at least 3-fold with PDGF-AB compared to an extract subjected to S/D and S/D removal by HIC in the absence of a wash with a non isocratic solution.

4. The extract according to claim 1, further comprising with bFGF.

5. The extract according to claim 1, having a low aggregate content.

6. The extract according to claim 1, wherein the extract is in solid form.

7. The extract according to 1, provided with a delivery agent.

8. The extract according to claim 7, wherein the delivery agent is made of natural and/or synthetic material selected from the group consisting of polymers, hydrogels, polyvinyl alcohol, polyethylene glycol, hyaluronic acid, chondroitin sulphate, gelatin, alginate, collagen matrices, carboxymethylcellulose, dextran, poly(2-hydroxyethylmethacrylate), agar, oxidize regenerated cellulose, self assembled peptides, poly(glycolic) acid, poly(lactic) acid, fibrin and combinations thereof.

9. A kit comprising a recipient containing an extract according to claim 1.

10. The kit according to claim 9, further comprising a delivery agent.

11. The kit according to claim 10, wherein the delivery agent is made of natural and/or synthetic material selected from the group consisting of polymers, hydrogels, polyvinyl alcohol, polyethylene glycol, hyaluronic acid, chondroitin sulphate, gelatin, alginate, collagen matrices, carboxymethylcellulose, dextran, poly(2-hydroxyethylmethacrylate), agar, oxidize regenerated cellulose, self assembled peptides, poly(glycolic) acid, poly(lactic) acid, fibrin and combinations thereof.

* * * * *